United States Patent
Gold et al.

(10) Patent No.: US 11,880,888 B1
(45) Date of Patent: Jan. 23, 2024

(54) COMPUTER-BASED SYSTEMS OF SPECIALIZED MICROSERVICES AND METHODS OF USE THEREOF

(71) Applicant: THE FEINSTEIN INSTITUTES FOR MEDICAL RESEARCH, INC., Manhasset, NY (US)

(72) Inventors: Howard B. Gold, Miami, FL (US); Konstanine Costalas, Merrick, NY (US); John Charles Cheeseborough, Yaphank, NY (US); Lawrence David Robertson, Astoria, NY (US)

(73) Assignee: THE FEINSTEIN INSTITUTES FOR MEDICAL RESEARCH, INC., Manhasset, NY (US)

( * ) Notice: Subject to any disclaimer, the term of this patent is extended or adjusted under 35 U.S.C. 154(b) by 0 days.

(21) Appl. No.: 18/063,179

(22) Filed: Dec. 8, 2022

Related U.S. Application Data

(60) Provisional application No. 63/288,349, filed on Dec. 10, 2021.

(51) Int. Cl.
*G06Q 40/08* (2012.01)
*G06F 9/54* (2006.01)
(Continued)

(52) U.S. Cl.
CPC ............ *G06Q 40/08* (2013.01); *G06F 9/547* (2013.01); *G06Q 10/00* (2013.01); *G06Q 50/22* (2013.01);
(Continued)

(58) Field of Classification Search
CPC ......... G06Q 50/22; G06Q 10/00; G06Q 40/00
See application file for complete search history.

(56) References Cited

U.S. PATENT DOCUMENTS

| | | | |
|---|---|---|---|
| 2007/0038480 A1* | 2/2007 | Kay | G16H 10/60 706/45 |
| 2020/0294667 A1* | 9/2020 | Campbell | G16H 50/20 |

FOREIGN PATENT DOCUMENTS

WO     WO-2019005214 A1 *   1/2019      G06F 19/328

OTHER PUBLICATIONS

Thesmar, D., Sraer, D., Pinheiro, L., Dadson, N., Veliche, R., & Greenberg, P. (2019). Combining the power of artificial intelligence with the richness of healthcare claims data: Opportunities and challenges. PharmacoEconomics, 37(6), 745-752. doi:http://dx.doi.org/10.1007/s40273-019-00777-6 (Year: 2019).*

* cited by examiner

*Primary Examiner* — Jason S Tiedeman
*Assistant Examiner* — Emily Huynh
(74) *Attorney, Agent, or Firm* — Greenberg Traurig, LLP

(57) ABSTRACT

A method performed by a first microservice processor includes receiving a first user indication from a first computing device from a plurality of computing devices of a second user that indicates that a first user requested a service of the second user. A first user-specific data container object is generated that includes first user-specific data elements associated with the service provided to the first user. First user-specific service-necessity information data objects are obtained from electronic resources. The first user-specific data elements and the first user-specific service-necessity information data objects are inputted into a machine learning engine to obtain ranked reference-claim data objects. A chosen reference-claim data object from the ranked reference-claim data objects is chosen by the second user to justify providing the service to the first user. A first user-specific service-specific-claim data object is built, stored in
(Continued)

the first user-specific data container object, and submitted to a second microservice.

24 Claims, 62 Drawing Sheets

(51) Int. Cl.
  *G16H 10/60* (2018.01)
  *G06Q 50/22* (2018.01)
  *G06Q 10/00* (2023.01)
  *G16H 40/20* (2018.01)
  *G16H 50/70* (2018.01)
(52) U.S. Cl.
  CPC ............ *G16H 10/60* (2018.01); *G16H 40/20* (2018.01); *G16H 50/70* (2018.01)

FIG. 11

| Category | Classification | Description |
|---|---|---|
| Case Data | | |
| | Medical History | a component expressing information generally related to the patient's medical history |
| | Family History | a component containing information regarding the patient's family medical history |
| | Pre-Condition | a component containing information about a relevant pre-existing medical condition |
| | Present Condition | a component containing information describing the reason for the clinical episode |
| | Pre-Diagnostic | a component containing previously performed laboratory tests or imaging |
| | Pre-Medication | a component describing medications prescribed or administered previous to the current episode |
| | Pre-Treatment | a component describing treatments prescribed or performed previous to the current episode |
| | Pre-Therapy | a component describing therapies prescribed or performed previous to the current episode |
| | Presenting Conditions | The attending physician's observations of the patient's presenting conditions. |
| | Clinical Circumstance | a component describing operational conditions or circumstances occurring in the clinical environment that may affect the current episode (i.e.: equipment availability, staffing issues, occupancy, etc.) |
| Physician Action | | |
| | Patient Diagnosis | a component describing the attending physician's diagnosis of the patient's condition |
| | Prescribed Medication | a component describing medications prescribed or administered during the current episode |
| | Prescribed Treatment | a component describing treatments prescribed or performed during the current episode |
| | Prescribed Therapy | a component describing therapies prescribed or performed during the current episode |

800

COMPUTER-BASED SYSTEMS OF SPECIALIZED MICROSERVICES AND METHODS OF USE THEREOF

FIELD OF TECHNOLOGY

The present disclosure generally relates to microservice orchestration, and more specifically to computer-based systems of specialized microservices and methods of use thereof.

BACKGROUND OF TECHNOLOGY

The present disclosure generally relates to improved computer-based platforms/systems, improved computing devices/components and/or improved computing objects configured for one or more novel technological applications of providing capabilities related to microservice orchestration based on bounded contexts and methods of use thereof, such as, but not limited to, complex and multi-faceted systems.

SUMMARY OF DESCRIBED SUBJECT MATTER

In some embodiments, the present disclosure provides an exemplary technically improved computer-based method may be performed by at least one processor that may include receiving a first user indication from at least first one computing device from a plurality of computing devices associated with a second user. The first user indication may indicate that a first user requested at least one service associated with the second user. A first user-specific data container object may be generated in response to the first user indication. The first user-specific data container object may include a plurality of user-specific data elements associated with the at least one service provided to the first user. A plurality of first user-specific service-necessity information data objects may be obtained over a communication network from at least one database stored on a plurality of electronic resources, via at least one application programming interface (API) call of at least one API from the plurality of APIs in an API layer. The plurality of first user-specific data elements of the first user-specific data container object and the plurality of first user-specific service-necessity information data objects may be inputted into a machine learning engine to obtain a ranked plurality of reference-claim data objects. The machine learning engine may include a trained machine learning model that has been trained to predict the ranked plurality of reference-claim data objects. At least one second computing device from the plurality of computing devices may be instructed to display on a graphic user interface (GUI), to the second user, the ranked plurality of reference-claim data objects. At least one chosen reference-claim data object from the ranked plurality of reference-claim data objects chosen by the second user through the GUI to justify providing the at least one service to the first user may be received. A first user-specific service-specific-claim data object may be built based at least in part on (i) the at least one chosen reference-claim data object, and (ii) the plurality of first user-specific data elements of the first user-specific data container object. The first user-specific service-specific-claim data object may be stored in the first user-specific data container object. The first user-specific data container object may be submitted to a second microservice.

In some embodiments, the present disclosure provides an exemplary technically improved computer-based method that may be performed by at least one processor and may include receiving a first user-specific data container object associated with a first user having received at least one service from a second user. The first user-specific data container object may include (i) a first user-specific service-specific-claim data object, and (ii) a plurality of first user-specific data elements associated with the at least one service provided to the first user. A plurality of first user-specific service-necessity information data objects may be obtained over a communication network from at least one database stored on a plurality of electronic resources, via at least one application programming interface (API) call of at least one API from the plurality of APIs in an API layer. The plurality of first user-specific service-necessity information data objects may lack any first user-specific necessity information associated with a necessity justification by the second user for providing the at least one service to the first user. The plurality of first user-specific data elements of the first user-specific data container object and the plurality of first user-specific service-necessity information data objects may be inputted into a machine learning engine to obtain a ranked plurality of reference-claim data objects. The machine learning engine may include a trained machine learning model that has been trained to predict the ranked plurality of reference-claim data objects. A service-necessity score may be assigned based on a comparison between the first user-specific service-specific-claim data object and the ranked plurality of reference-claim data objects. The method may determine one of (i) the first user-specific service-specific-claim data object fails an authorization when the service-necessity score is lower than a predefined necessity threshold score, or (ii) the first user-specific service-specific-claim data object meets the authorization when the service-necessity score is greater than the predefined necessity threshold score. When the first user-specific service-specific-claim data object meets the authorization, an authorization request may be sent to a transactor to execute a pre-determined action associated with the second user so that the second user is recognized for the at least one service based at least in part on the service-necessity score. The ranked plurality of reference-claim data objects, a data object that may include the service-necessity score, and a data object that may include the determining that the first user-specific service-specific-claim data object fails or meets the authorization may be stored in the first user-specific data container object. The first user-specific data container object may be stored in a blockchain database.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

FIG. 11 is a table of component classification of a patient consult in accordance with one or more embodiments of the present disclosure;

DETAILED DESCRIPTION

Figure 1:
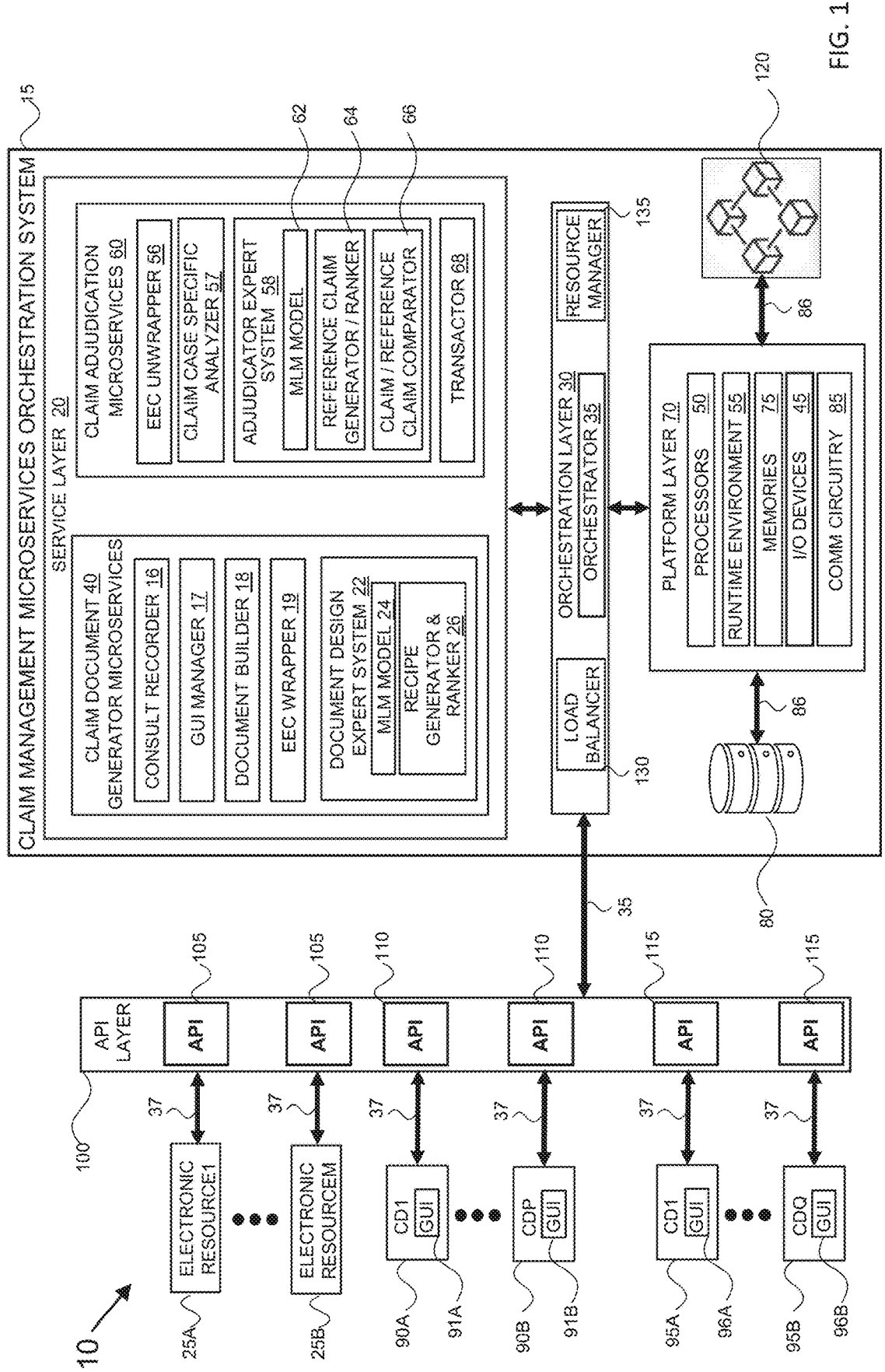
FIG. 1 is a block diagram of a claim management and adjudication (CMA) platform in accordance with one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

At least some embodiments of the systems and methods disclosed herein address a new approach to health care reform by removing inequities in access, inadequacies in funding, and gross variations in outcome in health care. Many of these reform initiatives have taken the form of managed care, in which a patient's medical treatment may be determined by a primary care physician, may be coordinated by a care manager, and channeled through a curated, high-value network of providers in order to optimize care and reduce costs. However, these approaches to care delivery may be predicated on the belief that it may be possible to control costs by providing physicians with information about performance and creating incentives that discourage overutilization while encouraging efficient, effective care.

At least some embodiments of the systems and methods disclosed herein solve an inherent flaw in managed care, where at the point of care, for example, such as in an emergency department, a physician makes a treatment decision about the patient: treat and discharge, admit for observation or in-patient care, or transfer to a more specialized hospital. The physician may need to be reimbursed for that care. However, prior to reimbursement, the payer, whether an insurer, government agency, or employer, may need to first assess if the treatment was medically necessary and clinically appropriate. Typically, the payer may have an institutional suspicion that a physician may have a variety of incentives for overutilization, such as a fear of malpractice claims, a drive to increase revenue, and/or a need to satisfy a health system's desire for increased relative value units (RVU).

Furthermore, payers have created a massive infrastructure to seek proof that a physician did not make an unnecessary medical decision. The payer, in fact, may place the physician on the defensive by creating an expectation that the provider must prove the value of their medical decision. Some payers may have devised a variety of utilization review mechanisms that are frequently complex and intrusive and fail to be based on a medical science knowledge base. As a result, there may be no way to know whether a given utilization review methodology is based on sound and reliable evidence. Thus, the current health care system may produce friction, antagonism, and distrust between the payer and provider. Furthermore, the current methods of utilization review may drive up the cost of care, as health systems negotiate higher prices for services to make up for losses caused by capricious and/or tactical challenges and denials, and as payers may look to offset the tremendous administrative costs by their process, as well as the expense of appeals, lawsuits, and settlements that frequently follow those denials of payment.

Thus, at least some embodiments of the systems and methods disclosed herein provide for an automated, evidence-based platform that may provide a dynamic medical knowledge base available to all stakeholders in the healthcare system, where the platform may be a single source of truth, replacing the current system of utilization review that may cause much acrimony between physicians, hospitals, and payers.

Embodiments of the present disclosure herein provide methods and systems for automated claim management and adjudication that may allow consumers, providers and payers to operate within an ecosystem that is transparent, administratively simple, and trusted. The systems for automated claim management and adjudication may utilize a modular, emergent utilization management platform that enables the automated determination of medical claims based upon, published, community-reviewed, medical science and clinical best practices, in a fully transparent format that may be available to all parties over a trust-based blockchain knowledge database. For example, the automated claim management and adjudication system may apply algorithms that link the patient presenting conditions with medical evidence to automate the medical necessity determination for the patient receiving a particular prescription by the health care provider. The claim management and adjudication system may use smart contracts stored in a blockchain that are agreed upon by the parties, which may automatically trigger payments to providers at the contracted rate or fee, or conversely may automatically deny claims if the real-time analytics may identify overuse, underuse, and misuse on the part of the provider.

In some embodiments, the claim management and adjudication platform may include a built-in automation platform, leveraging artificial intelligence and high-performance computing, to provide a superior customer experience for consumers.

In some embodiments, the claim management and adjudication platform may be self-optimizing and may use algorithms to learn from its interactions and outcomes. The claim management and adjudication platform may provide an orchestrated ecosystem of Expert Systems (ES) that employ artificial intelligence (AI) algorithms that may be driven by a community-reviewed, transparent, immutable blockchain knowledge database of medical science and clinical best practices that is accepted by a consensus of the stakeholders in the healthcare community. The platform may provide documentation assistance during healthcare delivery and claims preparation for the automated determination of medical necessity in claims adjudication.

In some embodiments, an Expert System (ES) may be a software module that may use a database of expert knowledge (e.g., a knowledge database described hereinbelow) and an inference (reasoning) procedure to solve problems that otherwise may need human competence or expertise. The inference procedure within as ES may be an algorithm that may be implemented as a heuristic structure of rules that express human judgement. This algorithm may be an inference engine that may be based upon "if-then" logic and is not self-adaptive.

In some embodiments, an ES may use other adaptive technologies within artificial intelligence (AI), such as machine learning (ML), to drive the inference, resulting in an adaptive system. ES technology may also embody human judgement in an automated decision-making process, meaning that the structure and function of the inference engine may be decided by a consensus of its stakeholders. As a result, the ES system as used herein may be an automated platform for negotiation where the system's decision-making process is the result of consensus. Furthermore, the Expert Systems may be potentially auditable, in that they can be designed to produce an audit trail of the automated decision-making process documenting how the system arrived at a particular conclusion regarding claim management and adjudication for any given patient case. This audit trail may be documented and stored for future review.

In some embodiments, the claim management and adjudication platform may include a built-in automation platform that incorporates algorithmically driven platforms for self-optimization, so as to acquire knowledge from the global body of medical science and clinical best practices as well as to learn from its own experience.

FIG. 1 is a block diagram of a claim management and adjudication (CMA) platform 10 in accordance with one or more embodiments of the present disclosure. The CMA platform 10 may include a claim management microservices orchestration system 15, a plurality of N electronic resources denoted ELECTRONIC RESOURCE 1 25A . . . ELECTRONIC RESOURCE N 25B, where N is an integer, a plurality of P computing devices CD1 90A . . . CDP 90B associated with a provider, where P is an integer, and a plurality of Q computing devices CD1 95A . . . CDQ 95B associated with a payer, where Q is an integer. The plurality of N electronic resources 25A . . . 25B, the plurality of P computing devices 90A . . . 90B associated with the provider, and the plurality of Q computing devices 95A . . . 95B associated with a payer communicate 37 with a plurality of APIs in an API layer 100. The API layer 100 may include APIs for implementing various API gateways. The API layer 100 may include, for example, at least one electronic resource API 105, at least one provider API 110, at least one payer API 115, or any combination thereof. The plurality of APIs in the API layer 100 may communicate 35 with the claim management microservices orchestration system 15.

The plurality of P computing devices 90A ... 90B associated with the provider (e.g., the plurality of provider computing devices) and the plurality of Q computing devices 95A ... 95B associated with a payer (e.g., the plurality of provider computing devices) may be referred to herein as the computing devices. Computing devices associated with the provider may be used by any person associated with the provider such as hospitals, laboratories, physicians, etc. for managing patient data, such as data generated from patient-physician interactions, laboratory and/or diagnostic equipment, and/or prescriptions, for example, as described herein. Similarly, computing devices associated with the payer may provide the payer with transparency to be able view via a graphic user interface monitoring dashboard, for example, any adjudication processes occurring within the claim management microservices orchestration system 15. Additionally, the monitoring dashboard may also be provided for viewing to the provider computing devices.

In some embodiments, a plurality of frontend computing devices for the CMA platform 10 may include the plurality of provider computing devices, the plurality of payer computing devices, and the plurality of electronic resources.

In some embodiments, the platform 10 may not differentiate between the plurality of P provider computing devices and the plurality of Q payer computing devices, which is shown here merely for conceptual clarity and not by way of limitation of the embodiments disclosed herein. Any of the computing devices may be either associated with the payer or provider and communicating with the claim management microservices orchestration system 15 via the API layer 100, for example.

In some embodiments, the CMA platform 10 may be based on a microservices architecture as shown in FIG. 1 where all of the functionalities may be provided by small software routines or microservices operating in the claim management microservices orchestration system 15. The claim management microservices orchestration system 15 may include a service layer 20, an orchestration layer 30, a platform layer 70, at least one storage device 80, and at least one blockchain ledger 120.

In some embodiments, the platform layer 70 may be implemented using a plurality of backend computing devices and/or servers and/or machines that may include at least one claim management processor 50 operating on at least one claim management microservices orchestration computer or machine, non-transient computing memories 75 in the claim management microservices orchestration computers, input/output (I/O) devices 45, communication circuitry 85 for communicating 35 over a communication network with all of the elements in CMA platform 10, and a runtime environment 55, which may provide the operating system environment for the claim management microservices orchestration computers.

In some embodiments, a plurality of backend computing devices for implementing the platform layer 70 may include the plurality of processors 50, the non-transient computing memories 75, the I/O devices 45, and the communication circuitries 85 and executing the runtime environment 55.

In some embodiments, the plurality of N electronic resources denoted ELECTRONIC RESOURCE 1 25A ... ELECTRONIC RESOURCE N 25B may include a processor and/or a controller (not shown) for receiving commands the at least one claim management processor 50 over the communication network via an API call from the at least one electronic resource API 105, for example. The API call may include a search query request data for specific data stored within the plurality of N electronic resources such that the API call may be configured to program controllers of the electronic resources so as to search in the stored databases and/or to identify any data files stored within the plurality of N electronic resources having data stored therein in accordance with the query request and to transmit the identified data in a plurality of patient-specific medical-necessity information data objects back to the at least one claim management processor 50.

In some embodiments, the platform layer 70 may communicate 86 to store and/or read data from the at least one storage device 80, the at least one blockchain ledger 120, or any combination thereof.

In some embodiments, data relayed from any of the computing devices to the claim management microservices orchestration system 15 may trigger the orchestration layer 30 to execute the steps of any of the microservices. Stated differently, an orchestrator 35 may route the data to a specific microservice to perform a specific microservice in the service layer 20. The service layer may include a claim document generator microservice 40 and a claim adjudication microservice 60. Each of the microservices may be software modules to perform functions of the CMA platform 10 as described herein. The claim document generator microservice 40 may include a consult recorder 16, a graphic user interface (GUI) manager 17, a document builder 18, an emergent episode container (EEC) wrapper 19, a document design expert system module 22 (e.g., a first machine learning engine) that may further include a first machine learning model 24, and a recipe generator and ranker module 26. The description of these microservices (e.g., software modules) will be discussed later.

In some embodiments, each computing device may include a graphic user interface (GUI) denoted by GUI 91A, GUI 91B, GUI 96A and GUI 96B that may be controlled by the GUI manager 17 microservice.

In some embodiments, the plurality of backend devices that when the processors 70 execute computer code stored in the non-transient computing memories 75 programs the processors to execute the claim document generator microservice 40 and claim adjudication microservice 60.

In some embodiments, claim adjudication microservices 60 may execute microservices that may be software modules to perform functions of the CMA platform 10 as described herein. The claim adjudication microservices 60 may include an emergent episode container (EEC) unwrapper module 56, a claim case specific analyzer module 57, a transactor module 68, and a claim adjudicator expert system module 58 (e.g., a second machine learning engine) that may further include a second machine learning model 62, a reference claim generator and ranker module 64, and a claim/reference claim comparator module 66. The description of these software modules will be discussed later.

The architecture of the claim management microservices orchestration system 15 may include services of both claim management and adjudication under one umbrella so as to provide these services to providers and payers in a neutral manner. Furthermore, the architecture may be scalable for maintaining good quality of service to all sides. That is, when too many users and/or processes may load the system, more machines may be added or removed to manage the load and resources in the claim management microservices orchestration system 15. The dynamic addition or removal of more machines may be performed by a load balancer 130 module and a resource manager 135 module in the orchestration layer 30 that are implemented by hardware, software, or both for balancing the computational efficiency and/or for managing resources.

In some embodiments, the resource manager 135 may use with high-performance computing and hardware acceleration technologies for load and resource management. For example, create hardware accelerators may be implemented using FPGA technology to facilitate some of the functions of the CMA platform 10.

Figure 2B:
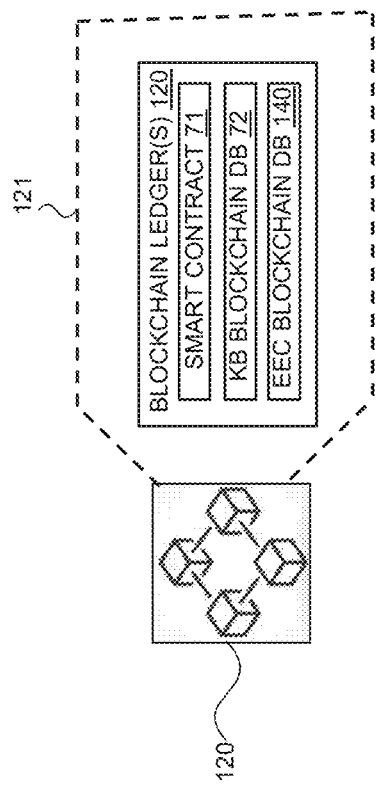
FIG. 2B is a block diagram of at least one blockchain ledger in a claim management microservices orchestration system in accordance with one or more embodiments of the present disclosure.
Figure 2A:
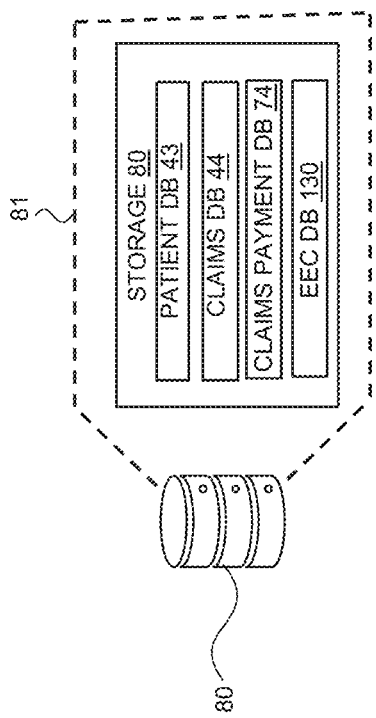
FIG. 2A is a block diagram of storage device of a claim management microservices orchestration system in accordance with one or more embodiments of the present disclosure.

FIG. 2A is a block diagram of the at least one storage device 80 of the claim management microservices orchestration system 15 in accordance with one or more embodiments of the present disclosure. The at least one storage device 80 may store a patient database (DB) 43 a claims database (DB) 44, a claims payment database (DB) 74, and an emergent episode container (EEC) database 130. The patient data, claim documents, claim payment data, and/or EEC data (described later) as generated by in the platform 10 may be stored in the at least one storage device 80 of the claim management microservices orchestration system 15.

FIG. 2B is a block diagram of the at least one blockchain ledger 120 in the claim management microservices orchestration system 15 in accordance with one or more embodiments of the present disclosure. Similarly, the at least one blockchain ledger 120 may be used to immutably store data in a smart contract database 71, a knowledge base blockchain database 72, and an EEC blockchain database 140. In some embodiments, these different blockchains may be stored at different locations.

In some embodiments, smart contracts stored in the smart contract database 71 may describe rules for claim management and adjudication between payers and providers for many payer—provider pairs.

In some embodiments, the knowledge base blockchain database 72 with medical data and resources may be used to determine a medical necessity for a provider providing medical services and/or treatments to a patient. The knowledge base blockchain database 72 may also be referred to herein as a Knowledge Base of Medical Science (KB-MS) or a medical-knowledge database. The EEC blockchain database 140 may be used for immutably storing data records in data containers for each patient that may store, in part, patient-provider records for determining medical necessity and payer claim payments to a provider based on the determined medical necessity that provided medical services and/or treatments to the patient.

In some embodiments, the plurality of N electronic resources denoted ELECTRONIC RESOURCE 1 25A . . . ELECTRONIC RESOURCE N 25B may be any website, full-text journals, newspapers, company information, e-books, dictionaries, encyclopedias, digital images, industry profiles, market research, for example, that are information sources for professional organizations and research institutions from around the world, ranging from the American Hospital Association to the European medical journal, for example. These medical and clinical information sources may be used to update the KB blockchain database 72 with published, community reviewed medical science and clinical best practices.

Trust is a fundamental issue undermining the healthcare ecosystem. Each stakeholder may implement processes that are closed and opaque to other stakeholders, and the systems are generally opaque to patients. This may foster distrust among the stakeholders, including consumers. In the embodiments disclosed herein, the CMA platform 10 provide a trust-based system leveraging a microservices orchestration architecture to allow both the providers and payers to use the same medical knowledge base (e.g., the KB Blockchain DB 72) and smart contracts (e.g., the smart contract 41 71) that leverage blockchain technology using the at least one blockchain ledger 120.

The blockchain is a digital ledger data structure that is shared at nodes in a network of computers associated with independent parties such as the provider and payer. Distributed ledger technology (DLT) implemented on the closed systems as described herein, strictly control membership and user roles. Blockchain technology enables the creation of historical records that are functionally immutable, transparent and completely auditable by any party having access to the blockchain. Actions may be taken at the nodes on any part of the blockchain, by any participant, and may be recorded in the blockchain. Therefore, data objects, and/or data containers recorded and stored on the blockchain may be traceable.

Once data is recorded in a blockchain, it is extremely difficult to modify or remove the recorded data since the transaction must be validated by a consensus of all the nodes in the blockchain network. As the network grows in size, so does the strength of the consensus. For a network of significant size, any unauthorized changes to a blockchain becomes nearly impossible with existing technologies, and thus blockchains are considered to be functionally immutable.

Blockchain technology may be used to implement a Smart Contract, which enforces agreements between the provider and payer, such that when an agreed set of conditions are met, an agreed upon action is automatically triggered within the blockchain, which may further enforce a level of trust between the payer and provider in the automated claim management and adjudication platforms described herein.

Figure 3:
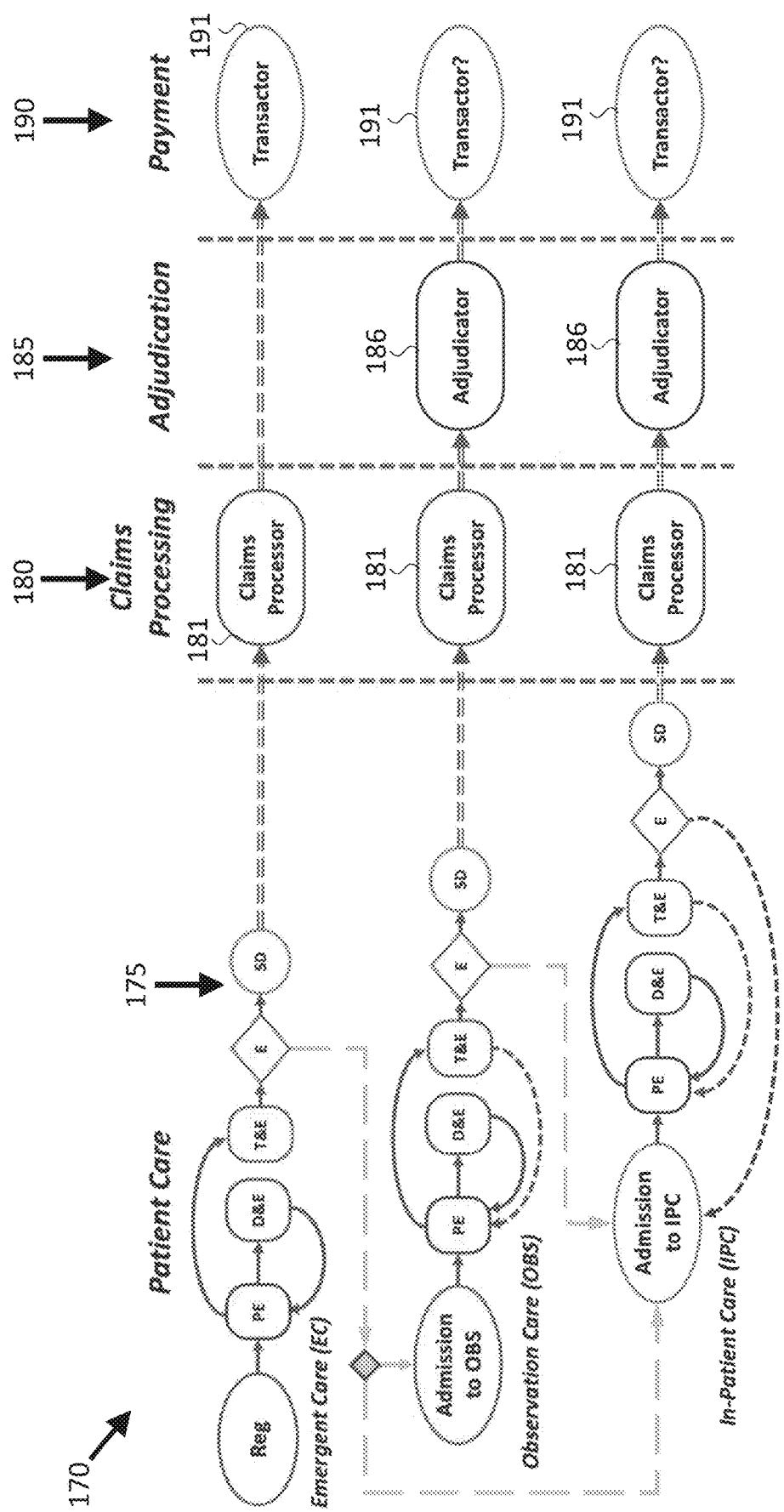
FIG. 3 is a flow diagram illustrating an emergent utilization flow implemented in four phases in accordance with one or more embodiments of the present disclosure.

FIG. 3 is a flow diagram 170 illustrating an emergent utilization flow implemented in four phases in accordance with one or more embodiments of the present disclosure. The claim management and adjudication platform 10 shown in FIG. 1 may be designed around an operating model that views Emergent Utilization as a series of four phases: a Patient Care phase 175, a Claims Processing phase 180, a Claims Adjudication phase 185, and a Payment Processing phase 190.

Figure 4:
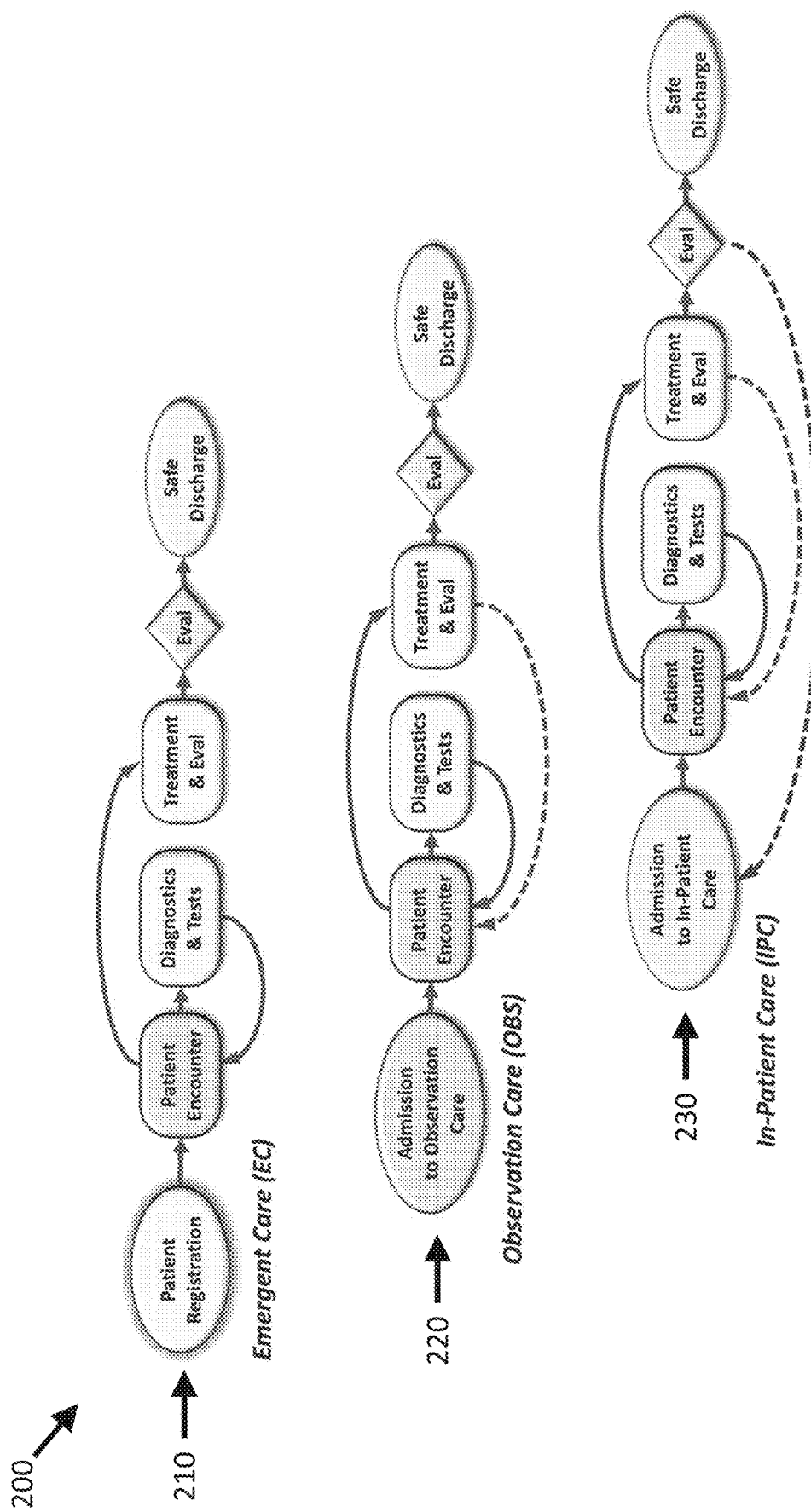
FIG. 4 is a flow diagram illustrating three patient care flows in a patient care phase in accordance with one or more embodiments of the present disclosure.

FIG. 4 is a flow diagram 200 illustrating three patient care flows in the patient care phase 175 in accordance with one or more embodiments of the present disclosure. The Patient Care phase 175 is the first phase represented in the CMA platform 10, which may include three flows that may or may not occur in sequence as shown in FIG. 4. An Emergent Care flow 210 may be where the patient is treated and released from the emergency department. An Observation Care flow 210 may be where the patient is held for observation within the emergency department. An In-Patient Care flow 230 may be where the patient is admitted into the hospital as an in-patient.

In some embodiments, the models of the three flows that are shown in FIG. 4 functionally describe each operation. However, for simplicity and clarity, it may be assumed that these flows may occur sequentially. However, a non-sequential execution of these flows may still apply to the same data model.

In some embodiments, the Patient Care phase 175 may start when a patient arrives in the emergency department of the hospital, for example, and may initiate a patient registration process. Registration may be the first step in the process of admission into the Emergent Care 210 flow as shown in FIG. 4 which may be modeled as three processes:

(1) The Patient Encounter may be a consultation between the patient and physician. It may be a discussion between the provider and the patient regarding anything related to the clinical incident. The patient encounter meeting may include a review of laboratory and/or diagnostic test results and any evaluations of the patient's status.

(2) Diagnostics & Tests may be ordered by the physician to be performed on the patient. These may include any laboratory tests, medical imaging, biopsies, and/or other procedures that assist in the determination of the patient's status.

(3) Treatment may be the prescription formulated by the physician and administered to the patient. Treatment may include the prescription of drugs, therapies, procedures, and the like.

In some embodiments, the operating model for Emergent Care may be centered around the Patient Encounter, as there normally may be a patient-physician consultation upon patient arrival and after any diagnostics may have been performed. Emergent Care may be a single pass process that may include an embedded cycle which may accompany any physician-ordered diagnostic tests. The Emergent care flow 210 then continues with treatment and evaluation.

In some embodiments, at the end of the emergent care flow 210, an evaluation of the patient's discharge status may be made by the physician. If discharge is determined to be safe and appropriate, the patient may be discharged. The Emergent Care flow 210 and the Patient Care phase of emergent utilization may be completed. If discharge is determined not to be safe or appropriate, the physician may order the patient to be admitted into an observation care flow 220 in the Patient Care phase.

In some embodiments, the Observation Care (OBS) flow 220 may be modeled as a process with the same embedded core cycle as that of Emergent Care (e.g., patient encounter, diagnostics and tests, etc.) However, the difference may be that the core cycle and treatment may be repeated multiple times during the OBS flow 220. At the end of each cycle, the patient may be evaluated, and either discharged, or the patient may be placed in another iteration of the OBS flow 220.

In some embodiments, the OBS flow 220 may have a procedural time limit, such as for example, a time limit of "Two-Midnights", where if it may be determined by the physician that it is not safe or appropriate to discharge the patient after this time limit, the patient may be admitted into the hospital as an in-patient. This may initiate the final process of the Patient Care phase, the In-Patient Care flow 230.

In some embodiments, the In-Patient Care (IPC) flow 230 may be modeled as having the entire OBS stage as its embedded core cycle. However, the entire IPC flow 230 including admission, may be repeated multiple times as the patient may need to be discharged and re-admitted to different departments within a healthcare facility, or may even be transferred between facilities. But ultimately, the patient's care is completed, and safely discharged from In-Patient care, completing the Patient Care Phase of Emergent Utilization. However, any time within the Patient Care Phase, the physician's evaluation of the patient may have presented conditions that justify a patient being admitted directly into IPC.

In some embodiments, in each of the three patient care flows shown in flow diagram 200 of FIG. 4, a physician, laboratory technician, a hospital administrator, laboratory equipment, for example, using any of the P computing devices CD1 90A . . . CDP 90B associated with the provider enterprise may generate data elements for storage in a unique data container associated with each patient. The data elements may include transcripts of the patient-physician interactions, lab results, physician notes, and the like for example, in arriving to the step of a safe discharge for the patient as shown in each of the three patient care flows shown in flow diagram 200.

When the patient care phase 175 is complete and the patient is discharged, the claim processing phase 180 begins, or the process of the provider building the claim for submission to the payer for payment. In the claim processing phase 180, the data and information recorded throughout the Patient Care Phase 175 may be assembled with the medical coding assignments made by the physician and billing specialist into a medical claim, according to a submission format specified by the payer. After review of the assembled claim, it is formally submitted to the payer, for review and payment.

When the medical claim is received by the payer, the Claims Adjudication phase 180 begins, whereby the payer evaluates the claim using a review of the medical necessity of the services provided to determine if payment of the claim is appropriate. If the payer determines that the care delivered to the patient was not appropriate, based upon medical necessity, payment of the claim is denied. If it is determined that the care delivered was appropriate, the claim is designated for payment, and the Payment Processing phase 190 may be implemented. Note that the Patient Care Phase 175 of the emergent care flow 210 may not use adjudication and the emergent utilization flow may directly implement the Payment Processing phase 190.

When the claim adjudication phase 185 determines that the claim is designated for payment, the Payment Processing phase 190 whereby the transfer of funds to pay the provider for services rendered may be executed.

In the embodiments of the present disclosure, the claim emergent utilization flow shown FIG. 3 may be a fully computer-implemented automated process that is implemented by the microservices implemented in the service layer 20 of the claim management microservices orchestration system 15. The claim document generator microservices 40 may receive data elements documenting the patient-provider interaction from admission to discharge that may be used for generating the claim document using the document builder software module 18 based on the received patient-provider data elements and a medical knowledge database that is stored in a blockchain.

In some embodiments, once the claim document data file is generated, the claim management microservices orchestration system 15 may create an emergent episode container (EEC) using the EEC wrapper software module 19 that stores the data elements documenting the patient-provider interaction from admission to discharge, and the generated claim document in the data container for a particular patient, for example.

Figure 5:
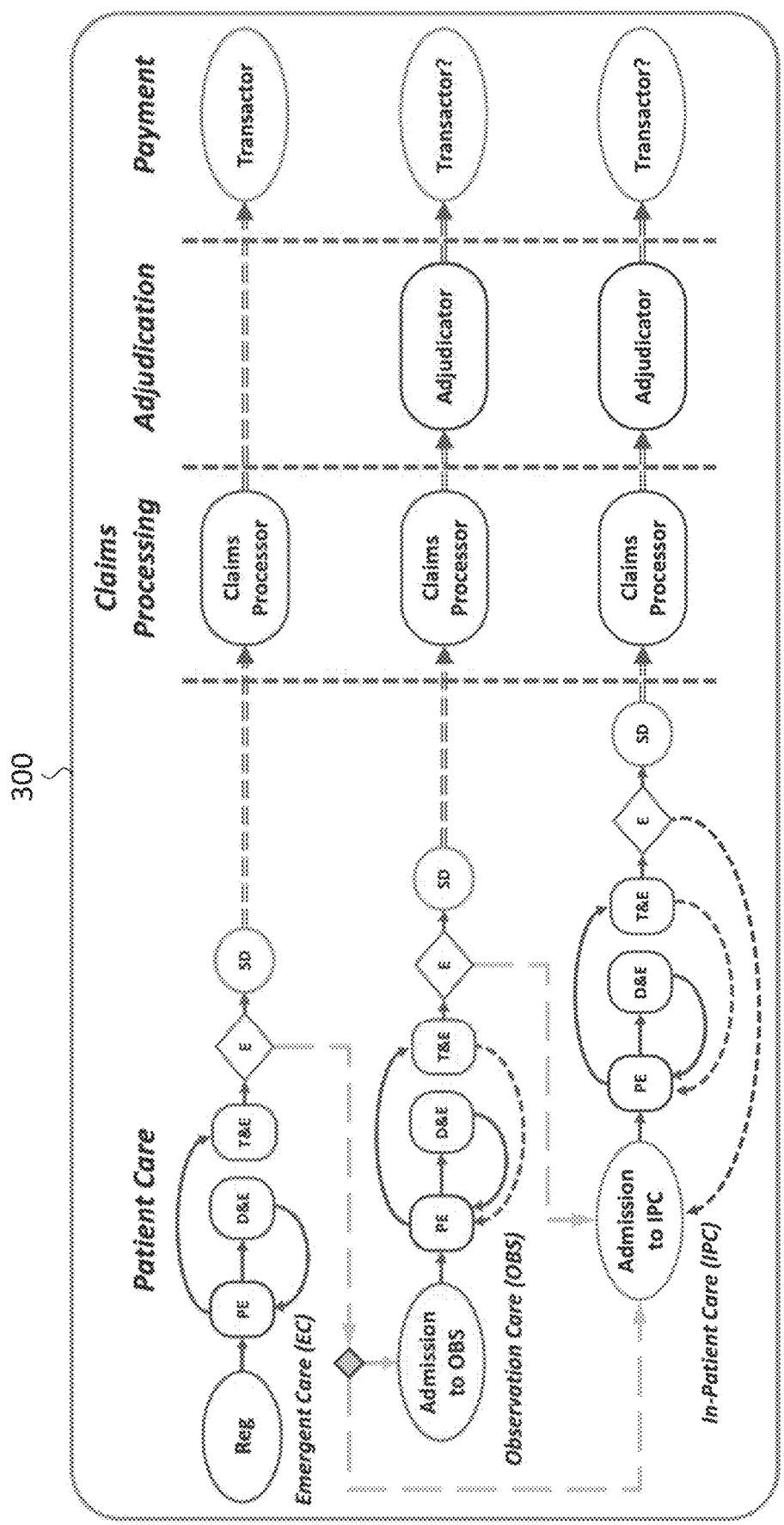
FIG. 5 illustrates an emergent episode container (EEC) in accordance with one or more embodiments of the present disclosure.

FIG. 5 illustrates an emergent episode container (EEC) 300 in accordance with one or more embodiments of the present disclosure. Operationally, the claim management microservices orchestration system 15 may be described as a computer-implemented agent that observes and performs actions on a data object. The data object may be the operating model of Emergent Utilization (EU) flow described in FIG. 3.

In some embodiments, the Emergent Episode Container (EEC) 300 may be a data construct that encapsulates and wraps the emergent utilization model as shown in FIG. 3.

The EEC 300 may be formatted to hold all of the data and information that occurred during each phase of the emergent utilization flow as shown in FIG. 3. Stated differently, the data wrapped in the completed EEC 300 may include data elements from every phase in the Emergent Utilization flow of FIG. 3, from the time that the patient was admitted in the emergency department, to the time that payment for the services rendered is either paid or written off by the provider. The EEC 300 may be further described as the data unit that may document the operational results of the entire emergent utilization flow for a given patient, for example.

In some embodiments, the claim management and adjudication (CMA) platform 10 may include a complex system of Expert Systems driven by a knowledge base called Knowledge Base of Medical Science (KB-MS), which may be also referred to herein as KB BLOCKCHAIN DB 72. The KB-MS may include published, community-reviewed, medical science and clinical best practices, and may be sourced from professional organizations and research institutions from around the world, ranging from the American Hospital Association to the European Medical Journal, and stored in the plurality of N electronic resources denoted ELECTRONIC RESOURCE1 25A . . . ELECTRONIC RESOURCEN 25B as shown in in FIGS. 1 and 2.

In some embodiments, KB-MS may be stored in a high-performance blockchain infrastructure to ensure the integrity and transparency of its contents, to provide the responsiveness required of a consumer application, and to promote trust among stakeholder community that are part of the claim management and adjudication (CMA) platform 10 (e.g., at least one of the providers and/or at least one of the payers). In other embodiments, the KB-MS may use the plurality of N electronic resources for implementing the high-performance blockchain infrastructure.

In some embodiments, KB-MS may be structured in accordance with the ICD-10-CM/PCS coding standard from the World Health Organization (WHO) and the conformant MS-DRG coding standard from the US Social Security Act, Section 1886(b), used by the Centers for Medicare and Medicaid Services (CMS).

In some embodiments, the implementation of the KB-MS may include the intelligent agent that may affect operations in Emergent Utilization in the claim management and adjudication (CMA) platform 10. Thus, the KB-MS in the claim management and adjudication (CMA) platform 10 may employ a built-in automation platform and real-time data analytics in precise orchestration to achieve the functionality and service that the claim management and adjudication (CMA) platform 10 is intended to provide.

In some embodiments, the Automated Knowledge Acquisition System (AKAS) may use a built-in automation platform that uses bots (software robots) to seek out and retrieve new materials that can be accessed over the internet, including subscribed information sources such as journals of medical science. The bots may use keywords, phrases, natural language processing (NLP), optical character recognition (OCR), and the like. Each provider-controller bot may be designed to acquire a specific type of information from a specific source. So, there may be a plurality of bots active within the system at any given time.

Figures 6, 7:
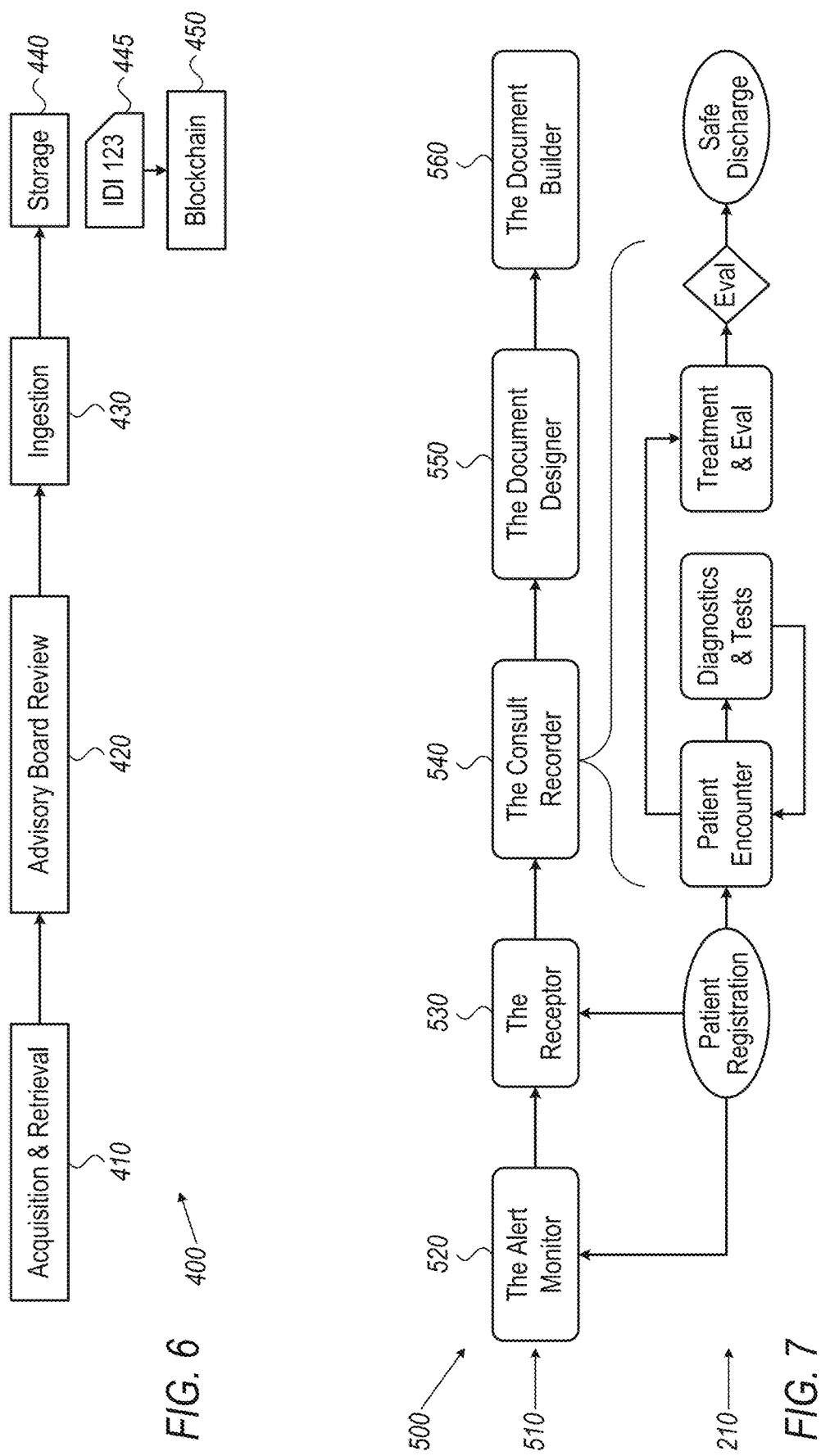
FIG. 6 illustrates a flow diagram of an automated knowledge acquisition process in accordance with one or more embodiments of the present disclosure.
FIG. 7 illustrates a flow diagram of an Automated Documentation Assistance flow in accordance with one or more embodiments of the present disclosure.

FIG. 6 illustrates a flow diagram of an automated knowledge acquisition process 400 in accordance with one or more embodiments of the present disclosure. The automated knowledge acquisition process 400 may include an acquisition and retrieval operation 410, an advisory board review 420, an automated ingestion module 430, and a storage step 440 of recording a data record or publication container 445 into the blockchain of a Knowledge Base of Medical Science (KB-MS) 450 (e.g., the same as KB-MS 630 shown hereinbelow).

In some embodiments, the knowledge acquisition and retrieval operation 410 may be initiated with the deployment of a plurality of provider-controlled bots that may access the remote publication source (e.g., the plurality of N electronic resources denoted ELECTRONIC RESOURCE 1 25A . . . ELECTRONIC RESOURCE N 25B as shown in in FIG. 1). The plurality of provider-controlled bots may then search the remote publication source and return a list of the new publications that was found in the KB-MS.

In some embodiments, the list of new publications may then undergo the advisory board review 420. On approval by the advisory board, the list of new publications may be passed on to the automated ingestion module 430. The automated ingestion module 430 may extract the key features from the publication and place a dictionary of those features into the publication container 445 along with the publication. The publication container may then be stored in the appropriate ledger in the KB-MS blockchain storage infrastructure.

In some embodiments, the steps in the knowledge acquisition and retrieval operation 410 may be performed by the at least one processor 50. However, as the claim management and adjudication (CMA) platform 10 may evolve and become more intelligent, there may be less of a need for human review of the incoming materials in the advisory review board step 420, but periodic human audits of the materials to be stored in the knowledge base may be procedurally required when this step may be fully automated.

FIG. 7 illustrates a flow diagram 500 of an Automated Documentation Assistance flow 510 in accordance with one or more embodiments of the present disclosure. The previous description of the emergent care flow 210 was a high-level description describing the interactions between patient and provider using any of the P computing devices (CD1 . . . CDP) associated with the provider that communicate 37 with the claim management microservices orchestration system 15 via the API layer 100. However, behind each of the steps in the emergent care flow 210, there may be a parallel technical flow 510 to collect and/or transform and/or manage the data collected from any of the P computing devices (CD1 . . . CDP). The automated Documentation Assistance flow 510 may be technically implemented by the microservices (e.g., software modules) such as an alert monitor 520, a receptor 530, a consult recorder 540 (same as the consult recorder 16 of FIG. 1), a document designer 550, and a document builder 560.

In some embodiments, patient registration may initiate the emergent episode when the Alert Monitor software 520 executed by any of the P computing devices (CD1 . . . CDP) may detect the initiation of a patient registration process. The alert monitor 520 may send an alert to the orchestrator 35 to assign the Receptor 530 to handle the new patient event.

In some embodiments, the assignment of the Receptor 530 may be implemented by the EEC wrapper module 19, for example, where an orchestrated system of bots may assist administrative staff during patient registration, by retrieving patient records, verifying benefits, recording referrals, and acquiring pre-approvals from the patient's insurance plan. These bots may provide the assistance to the administrative staff via the GUI manager 17 to any of the P computing devices associated with the provider enterprise and displayed on any of the P GUI denoted GUI 96A . . . GUI 96B.

In some embodiments, the Receptor 530 in the EEC wrapper module 19 may generate the Emergent Episode Container (EEC) 300 for the new patient that may store the incident data and/or information throughout the emergent utilization process and/or the registration information in the EEC 300 data container.

In some embodiments, the Clinical Documentation System may include the consult recorder 540, the document designer 550 and the document builder 560 software modules, which may provide automated assistance for the clinician through any of the P graphic user interfaces (e.g., GUI 91A . . . GUI 91B) in the documentation of events occurring during the patient care phase of EU. There may be an operational cycle, centered around the patient encounter, that may be replicated in each process within the patient care phase 175. The patient encounter may be where the patient and physician discuss the patient's condition and status. It may be where the results of diagnostics, treatment plans, therapies and prescriptions are presented to the patient and discussed. The clinical documentation system may be activated by the patient encounter whenever it occurs during healthcare delivery.

In some embodiments, the first subsystem of the clinical documentation system may be the Consult recorder 540, which may be activated when the patient encounter begins. It may record the conversation between the physician, patient, and may include the physician's notes. It may compile and store a transcript of the encounter as patient-specific data elements via any of the P computing devices in the patient database 43, for example.

Figure 8:
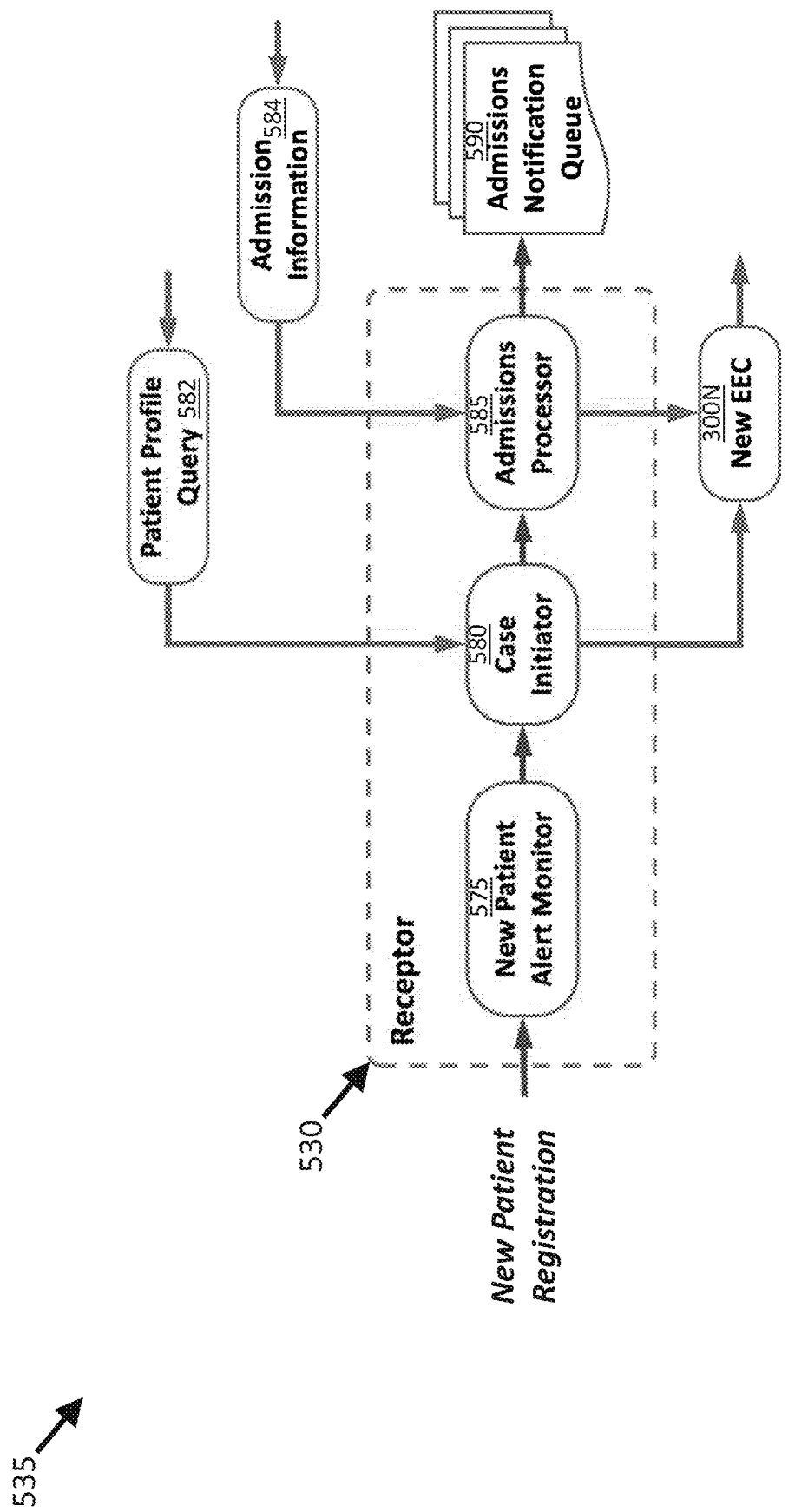
FIG. 8 is a flow diagram of a receptor in accordance with one or more embodiments of the present disclosure.

FIG. 8 is a flow diagram 535 of the receptor 530 in accordance with one or more embodiments of the present disclosure. Patient registration may initiate the Emergent Utilization process as shown in FIG. 3. Patient Registration may be facilitated by the Receptor subsystem 530 of the CMA Platform 10. The Receptor 520 may be configured to operate in three processes: the Alert Monitor 575, the Case Initiator 580, and the Admissions Processor 585.

In some embodiments, when the registration process begins, the Alert Monitor 575 may be activated by the reception of a "new case request" initiated by a member of the clinical staff. In other embodiments, the Alert Monitor 575 may autonomously interact with the hospital's patient registration systems to detect a new patient registration. Once activated, the receptor 530 may assign the Case Initiator 580 to process the event. The Alert Monitor 575 may then return to monitoring or waiting for new patient arrivals.

In some embodiments, the Case Initiator 580 may create a profile for a new patient or may query the patient profile 582 for an existing patient. The Case Initiator 580 may generate a new EEC 300N (Emergent Episode Container) for the case and may initialize the EEC 300N with the patient profile and relevant admission information 584. The Case Initiator 580 may relay the EEC 300N to the Admissions Processor 585.

In some embodiments, the Admissions Processor 585 may access the case information in the EEC 300 and may continue the registration process by recording any available referrals, verifying the patient's information, insurance benefits, for example. The Admissions Processor 585 may store the information in the case EEC and may post a completion notification in the platform Admissions Notification Queue 530. Thus, the flow diagram 535 may illustrate the Receptor function and the automated assistance for patient registration.

In some embodiments, the Clinical Documentation System of the CMA Platform 10 may provide automated assistance for the clinician in the documentation of events occurring during the patient care phase of Emergent Utilization. As described in the operating model, there may be an operational cycle, centered around the patient encounter, that may be replicated in each process within the patient care phase. The patient encounter may be where the patient and physician may discuss the patient's condition and status. During the patient encounter, the results of diagnostics, treatment plans, therapies and prescriptions may be presented to the patient and discussed. Automated documentation assistance may be implemented by the Consult Recorder 540.

Figure 9:
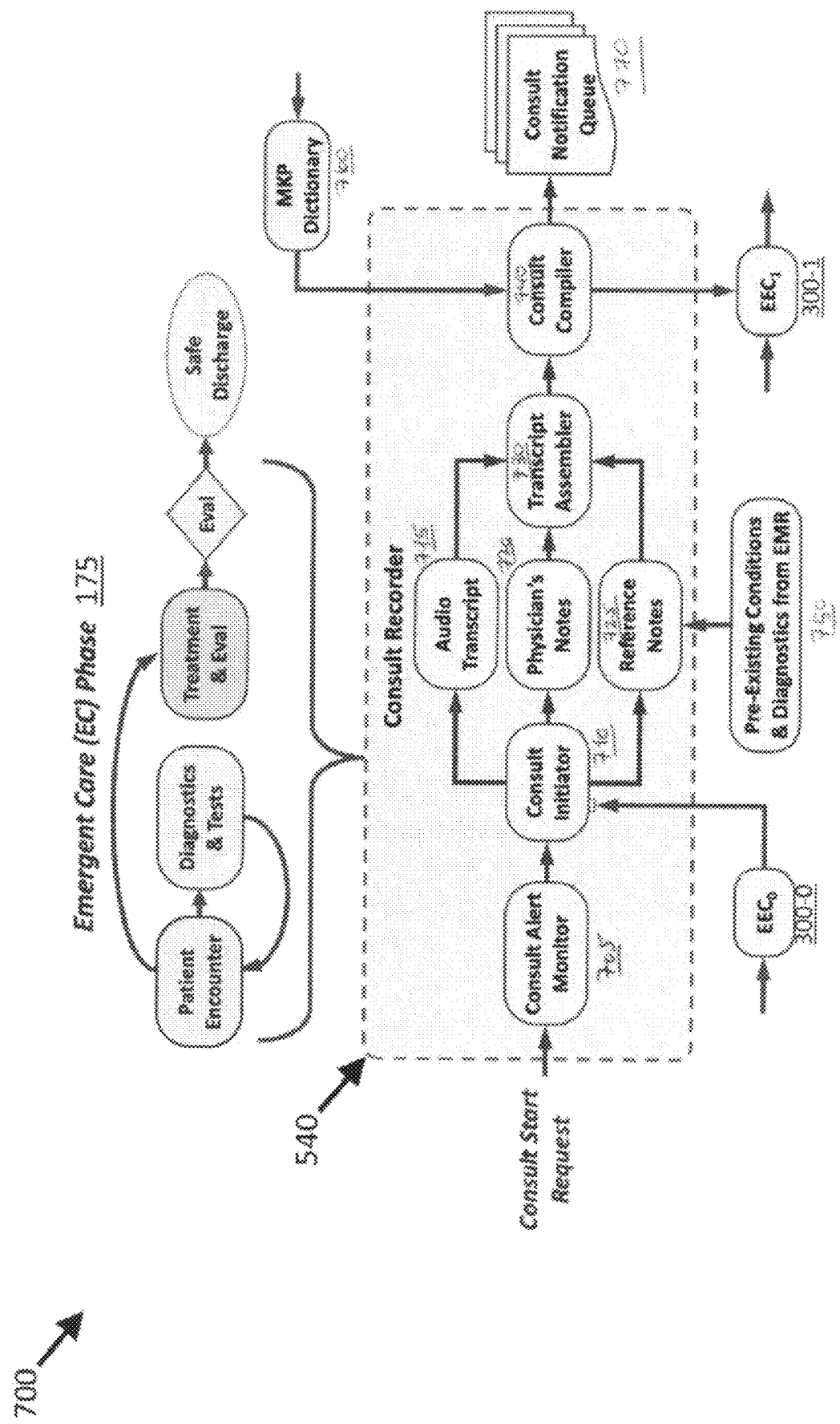
FIG. 9 is a flow diagram of a consult recorder in accordance with one or more embodiments of the present disclosure.

FIG. 9 is a flow diagram 700 of the consult recorder 540 in accordance with one or more embodiments of the present disclosure. The Consult Recorder 540 may be activated by the receipt of a request to start a consultation. A Consult Alert Monitor 705 may receive the request to start the consultation. The Consult Alert monitor 705 may assign a Consult Initiator 710 to process the event. The Consult Alert monitor 705 may then await for a next request to start a consultation.

In some embodiments, the Consult Initiator 710 may access the EEC 300-0 to acquire the consult data and to initiate consult recording. The consult recording may begin with the acquisition of information relevant to the consultation, such as the patient's pre-existing conditions and/or diagnostics from the electronic medical records (EMR) 750, and the results of diagnostic tests, prescriptions, and/or observations, for example. This information may be attached to consult recording in a Reference Notes 725 section. The recording session may continue with the recording of the Physician's Notes 720 and the optional Audio Transcript 715.

In some embodiments, when the consult ends, the notes may be passed to the Transcript Assembler 730 which may assemble the notes as a package and may relay them on to the Consult Compiler 740. Note that the CMA Platform 10 may use Speech-to-Text processing technology for the conversion of an included audio transcript 715 into a text manuscript.

In some embodiments, the Consult Complier 740 may initialize a Consult Package 610 shown later in FIG. 12. The Consult Complier 740 may accept the assembled consult transcript that may be inserted into the consult package 610. The Consult Complier 740 may access a Medical Key-Phrase Dictionary (MKPD) 760 in a Knowledge Base of Medical Coding (KB-MC). The MKPD dictionary 760 may include a collection of key-phrases that may be associated with ICD-10-PCS and ICD-10-CM codes. The Consult Complier 740 may use Natural Language Processing (NLP) and the MKPD 760 to search the assembled transcript for key-phrases from the Consult Key-Phrase Dictionary which may be populated into the Consult Package 610. Finally, the Consult Complier 740 may store the Consult Package 610 in the EEC 300 and may posts a notification in the \Consults Notification Queue 770. Note that multiple patient consultations may occur during the Patient Care Phase of Emergent Utilization generating n multiple Consult Packages 610-0, 610-1 . . . 610-$n$ (FIG. 12) that may be stored in the EEC 300 for the case, where n is an integer.

Figure 10:
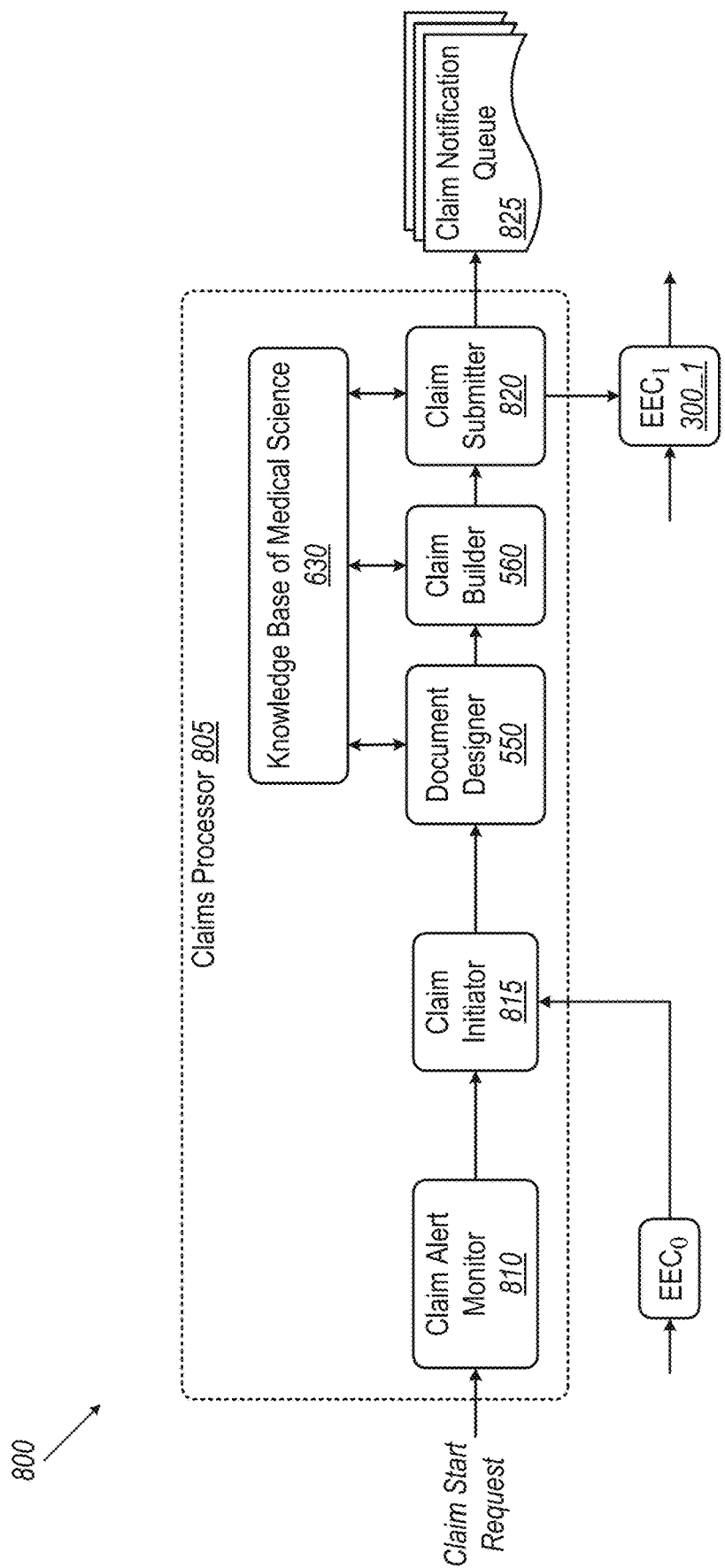
FIG. 10 is a flow diagram of a claims processor in accordance with one or more embodiments of the present disclosure.

FIG. 10 is a flow diagram 800 of a claims processor 805 in accordance with one or more embodiments of the present disclosure. The claims processor 805 may include a claim alert monitor 810, a claim initiator 815, the document designer 550, the claim builder 560, and a claim submitter 820. The claim initiator 815 may receive input data from $EEC_0$ 300_0. The claim submitter 820 may output data to be stored in $EEC_1$ 300_1. The document designer 550, the claim builder 560, and/or the claim submitter 820 may bidirectionally communicate data with a Knowledge Base of Medical Science (KB-MS) 630.

FIG. 11 is a table 800 of component classification of a patient consult in accordance with one or more embodiments of the present disclosure. The table 800 may provide classification of the patient-specific data in the plurality of patient-specific data elements that may be stored in the EEC 300. The plurality of patient-specific data elements may also include data of the physician's actions when providing the at least one medical service to the patient.

Figure 12:
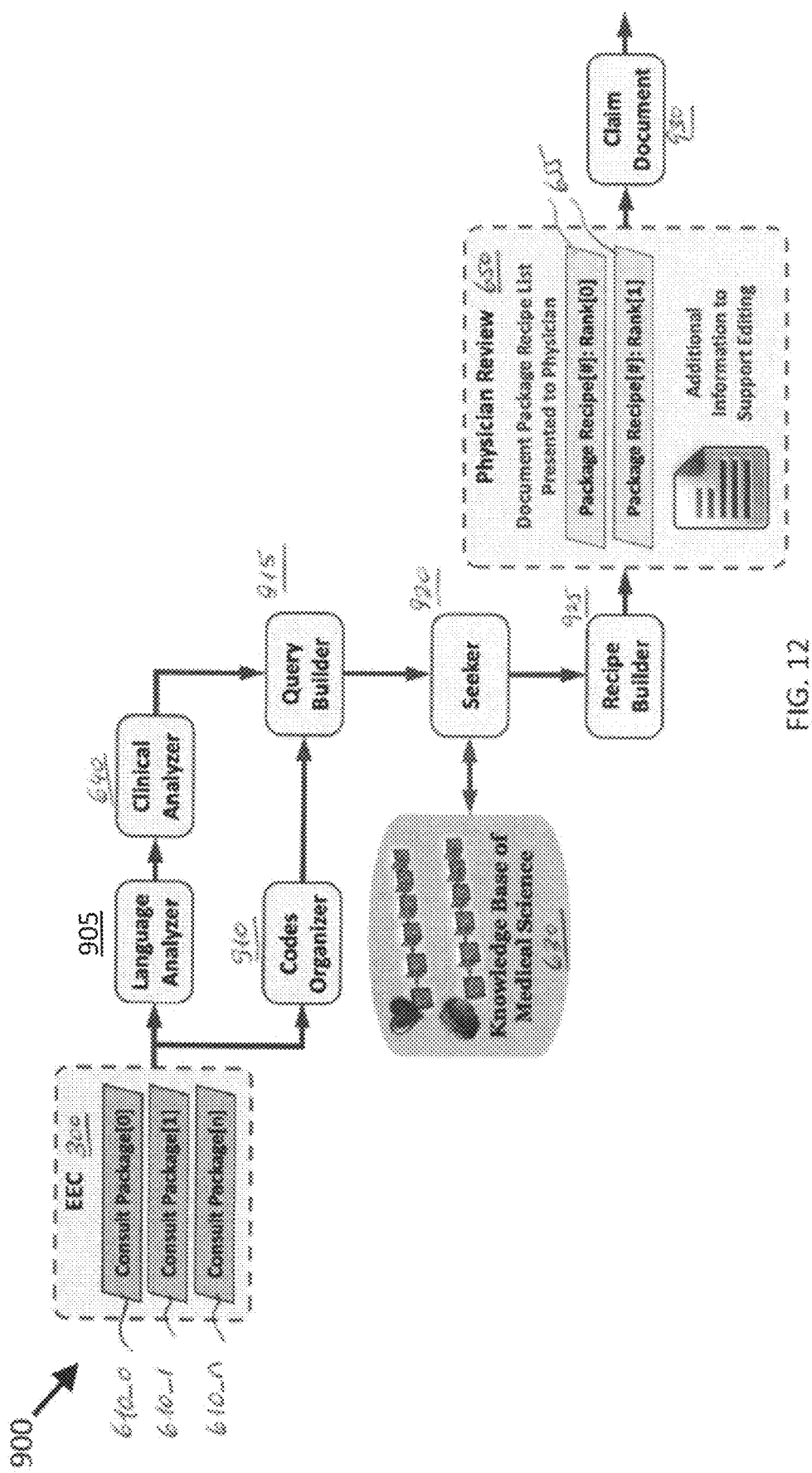
FIG. 12 is a flow diagram of a document designer in accordance with one or more embodiments of the present disclosure.

FIG. 12 is a flow diagram of the document designer 550 in accordance with one or more embodiments of the present disclosure. The document designer 550 may include software modules such as, for example, a language analyzer 905, the clinical analyzer 640, a codes organizer 910, a query builder 915, a seeker 920, and a recipe builder 925. The language analyzer 905 and the codes analyzer 910 may receive data stored in the EEC 300 such as any or all of the n consult packages 610-0, 610-1, ... 610-n. The seeker 920 may communicate with the KB-MS 630.

In some embodiments, when the Patient Care Phase of Emergent Utilization may be completed, the Claims Processing Phase may begin. Claims processing may be implemented in the Claims Processor 805 subsystem as shown in FIG. 10. The Claims Processor 805 may be an automated AI system, driven by the KB-MS 630 that may use the clinical consult transcript package 610 stored in the case EEC 300 by the Consult Recorder 540 to compile and format the insurance claim. The Claims Processor 805 may automatically submit the claim to the payer.

In some embodiments, claims processing may begin with the reception of a Claim Start Request which may be relayed to a Claim Alert Monitor 810. The Claim Alert Monitor 810 may alert the CMA platform 10 to assign a Claim Initiator 580 to process the event. The Claim Alert Monitor 810 may then return to waiting for a reception of a next claim start request. The Claim Initiator 580 may access the case EEC 300-0 and initializes the claims process. The Claim Initiator 580 transfer control to the document design processor, the Document Designer 550.

In some embodiments, the Document Designer 550 may be configured to organize the ICD-10 medical codes designated within any or all of then consult packages 610-0, 610-1, ... 610-n acquired from the EEC 300. The Document Designer 550 may use the Language Analyzer 905 applying Natural Language Processing (NLP) to extract and/or to structure the language components from any or all of the n consult packages 610-0, 610-1, ... 610-n and/or to compile the language components into a summary report. The Document Designer 550 may use the Clinical Analyzer 640 to apply domain knowledge (Expert Systems) to extract and/or to develop an understanding of the care delivery components recorded in any or all of the n consult packages 610-0, 610-1, ... 610-n. One of the operations of the Clinical Analyzer 640 may be to categorize the relevant components of the patient consults. These classifications may include, but are not limited to those described in the table 800 as shown in FIG. 11.

In some embodiments, the results from the Codes Organizer 910 and the Clinical Analyzer 640 may be transmitted to the Query Builder 915 which may be configured to synthesize the information into a set of queries for the KB-MS 920. The query set may be transmitted to the Seeker 920 which may initiate an application programming interface (API) call to program the databases of the KB-MS 630 to seek medical necessity care delivery data in the databases so as to support the medical necessity of the care delivery based on the information in the query set and to transmitted the medical necessity care delivery data back to the Seeker 920.

In some embodiments, the Recipe Builder 925 may use the results acquired by the Seeker 920 (e.g., retrieved medical necessity care delivery data) to assemble a ranked list of recipes 655 that describe documentation packages that may be used to formulate claims that support the medical necessity of the care delivery. The recipes may have different levels of granularity ranging from portions of a claim to an entire medical claim to justify administering the medical service to the patient by the provider. These recipes may be displayed for the physician to review in the ranked list. The Recipe Builder 925, using the Recipe Generator and Ranker Module 26 and the machine learning model 24, may rank the recipes according to their correlation to the data retrieved in the KB-MS 630 queries, the strength of their argument and/or frequency of use. The ranked recipes may be also referred to herein as a ranked plurality of reference-claim objects.

In some embodiments, the machine learning model 24 may be trained to assign a medical necessity score (MNS) between 0 and 100, with 100 being the highest level of justifiable medical necessity, for each medical service provided to the patient based on the patient history, symptoms and complaints as recorded in the encounter transcripts which prompted the patient to seek medical care.

In some embodiments, the machine learning model 24 may further be configured to rank the medical necessity scores that may be determined from the knowledge base of medical science 630.

In some embodiments, in a non-limiting example, used merely for a visual and conceptual clarity, and not by way of limitation of the embodiments disclosed herein, suppose a patient comes into a health care provider facility complaining of very severe abdominal pain. The attending physician may order a very costly colonoscopy in addition to a bank of other diagnostic tests. However, severe abdominal pains may be generally caused, for example, by a variety of factors such as severe constipation, irritable bowel syndrome, food poisoning, appendicitis, gastroesophageal reflux and/or cancer to name a few. Thus, if the reason for the physician to order the colonoscopy is only on the basis of the patient experiencing severe abdominal pains, the medical necessity score (MNS) may have a low MNS=30. Thus, there may be a low likelihood that the claim to pay for the colonoscopy may be approved for payment by the payer.

In some embodiments, however, if the patient not only tells the physician of experiencing severe abdominal pains but also of a change in bowel habits, weight loss, a family history of colon cancer, and blood in the patient's stool and these items may be recorded in the encounter transcript, the machine learning model 24 may assign respective medical necessity scores to ordering a colonoscopy based on each of these items recorded in the encounter transcripts such as for example, severe abdominal pains (MNS=30), a change in bowel habits (MNS=40), weight loss (MNS=60), a family history of colon cancer (MNS=70), and blood in the patient's stool (MNS=90). If the physician, during the colonoscopy procedures, finds polyps for removal, the medical necessity score may be MNS=90 and if the polyps are cancerous (MNS=99). Thus, in this latter scenario, the physician may have a much higher justification level of medical necessity based on the multiple items having multiple MNS values in the encounter transcript for ordering the colonoscopy as opposed to the physician order a colonoscopy based on the patient experiencing severe abdominal pains only.

In some embodiments, an overall or total MNS for providing the medical services to the patient may be based on the highest MNS value for the MNS of each item in the patient information encounter transcripts. In other embodiments, the total MNS may be a weighted average of the MNS value for each item in the patient information encounter transcripts.

In some embodiments, the level of medical necessity may be determined by the machine learning engine (e.g., MLM 24) using the patient-specific medical-necessity information data objects received from the KB-MS 630 to justify the medical service provided to the patient by the provider in order to generate the recipes and to rank them according to a level of medical necessity. The machine learning engine of the document designer 550 may be trained with training datasets that may have input data vectors that include in part the consult packages 610_0, 610_1 . . . 610_n (e.g., any patient-specific data elements from data from the categories shown in the table 800 of FIG. 11) and output data vectors having a set of package recipes that are ranked according to medical necessity. The medical necessity may be defined using the MNS values (similarly as shown in the exemplary colonoscopy scenario described hereinabove) that may be taken from the KB-MS 630.

In some embodiments, the Document Designer 550 may be an automated expert system such as the document design expert system 22 in FIG. 1 that may be executed by the at least one claim management processor 50 to generate queries via API calls to the KB-MS 630 (e.g., KB BLOCK-CHAIN DB 42 in FIG. 1).

In some embodiments, the Document Designer 550 may search the patient case specifics stored in the EEC 300 such as the encounter transcript, medical history, emergency room (ER) circumstances and/or any other related patient case specific. The patient case specifics may include a plurality of patient-specific data with data records of a patient-physician interaction, a patient diagnostic test result, a patient treatment, and/or a patient evaluation, for example.

In some embodiments, the Document Designer 550 may use algorithms to discern the content and intent of the patient-physician conversation (or transcripts thereof). These algorithms may leverage natural language processing (NLP) in the Language Analyzer 905, optical character recognition (OCR), or both to determine the content and intent within the transcript. Once this is done, the Document Designer 550 may generate queries to program the KB-MS 630 to identify relevant medical necessity care delivery data in data files and/or documentation stored in the KB-MS 630 and to transmit the identified medical necessity care delivery data in the KB-MS 630 back to the Document Designer 550 (e.g., the Seeker 920). If successful, the recipe builder 925 may assemble a ranked list 655 of recipes to support the medical necessity of the physician's prescription.

In some embodiments, the list of recipes (also known as a first ranked plurality of reference-claim document objects) may then be presented for a Physician Review 650 to the physician for review, selection, and modification as shown in FIG. 12. The Document Package Recipe List 655 may then be displayed to the physician for review and selection via any of the P graphic user interfaces (e.g., GUI 91A . . . GUI 91B).

In some embodiments, displaying the list of recipes may include providing feedback to the physician as to whether the chosen medical service provided by the physician to the patient had sufficient medical necessity to justify providing the chosen medical service for the patient.

In some embodiments, when the physician selects the document package recipe 650 from the ranked list (e.g., the chosen reference-claim document object from the first ranked plurality of reference-claim document objects) via any of the P graphic user interfaces (e.g., GUI 91A . . . GUI 91B), the selection triggers the at least one claim management processor 50 to relay the selection to the Claim Builder 560 in FIG. 10.

In some embodiments, the document package recipe 650 may include the MS-DRG or ICD-10-PCS code specified in the physician's prescription.

In some embodiments, the Claim Builder 560 may assemble the document package needed for generating the claim according to any formatting requirements or other constraints specified by the insurance plan. EEC Wrapper module 19 may store the document package in the EEC 300 which may be relayed to a Claim Submitter 820 as shown in FIG. 10. The Claim Submitter 820 may transmit the completed claim to the payer and may receive a confirmation of the reception of the claim by the payer. The at least one claim management processor 50 via the Claim Submitter 820 may then notifies the CMA platform 10 via a claim notification queue 825 that the Claims Processing phase has been completed. The EEC 300 may be submitted to the claim adjudication microservices 60.

Figure 13:
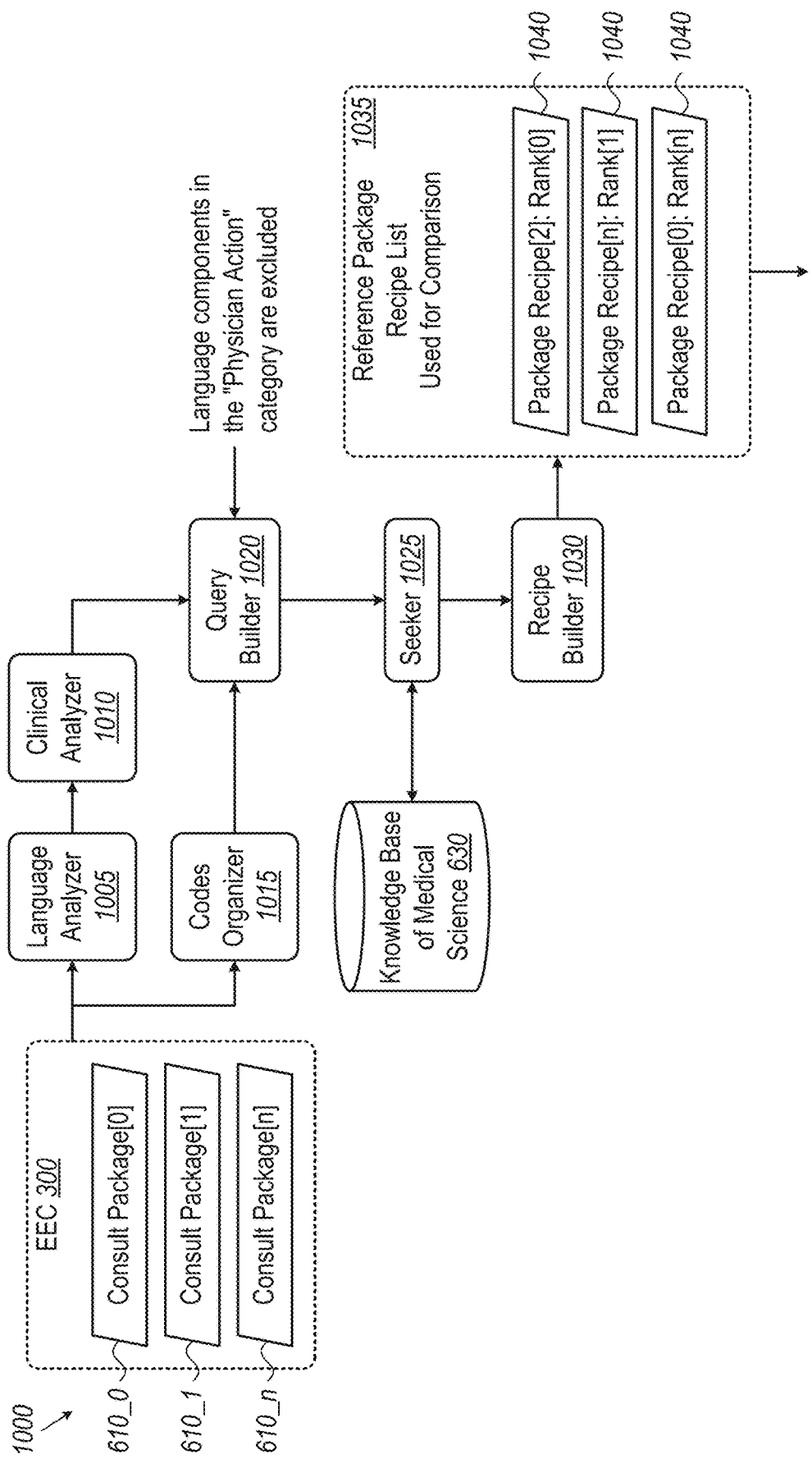
FIG. 13 is a flow diagram of an adjudication document designer in accordance with one or more embodiments of the present disclosure.

FIG. 13 is a flow diagram of an adjudication document designer 1000 in accordance with one or more embodiments of the present disclosure. The adjudication document designer 1000 may include software modules such as, for example, a language analyzer 1005, a clinical analyzer 1010, a codes organizer 1015, a query builder 1020, a seeker 1025, and a recipe builder 1030. The language analyzer 905 and the codes analyzer 910 may receive data stored in the EEC 300 such as any or all of the n consult packages 610-0, 610-1, . . . 610-n. The seeker 1025 may communicate with the KB-MS 630. The software modules shown in FIG. 13 for the adjudication document designer 1000 are equivalent to the software modules shown in FIG. 12.

In some embodiments, the claim case specific analyzer 57 may analyze case specifics in the EEC 300 that may include the plurality of patient-specific data with data records including a patient-physician interaction, a patient diagnostic test result, a patient treatment, and/or a patient evaluation, for example.

Figure 14:
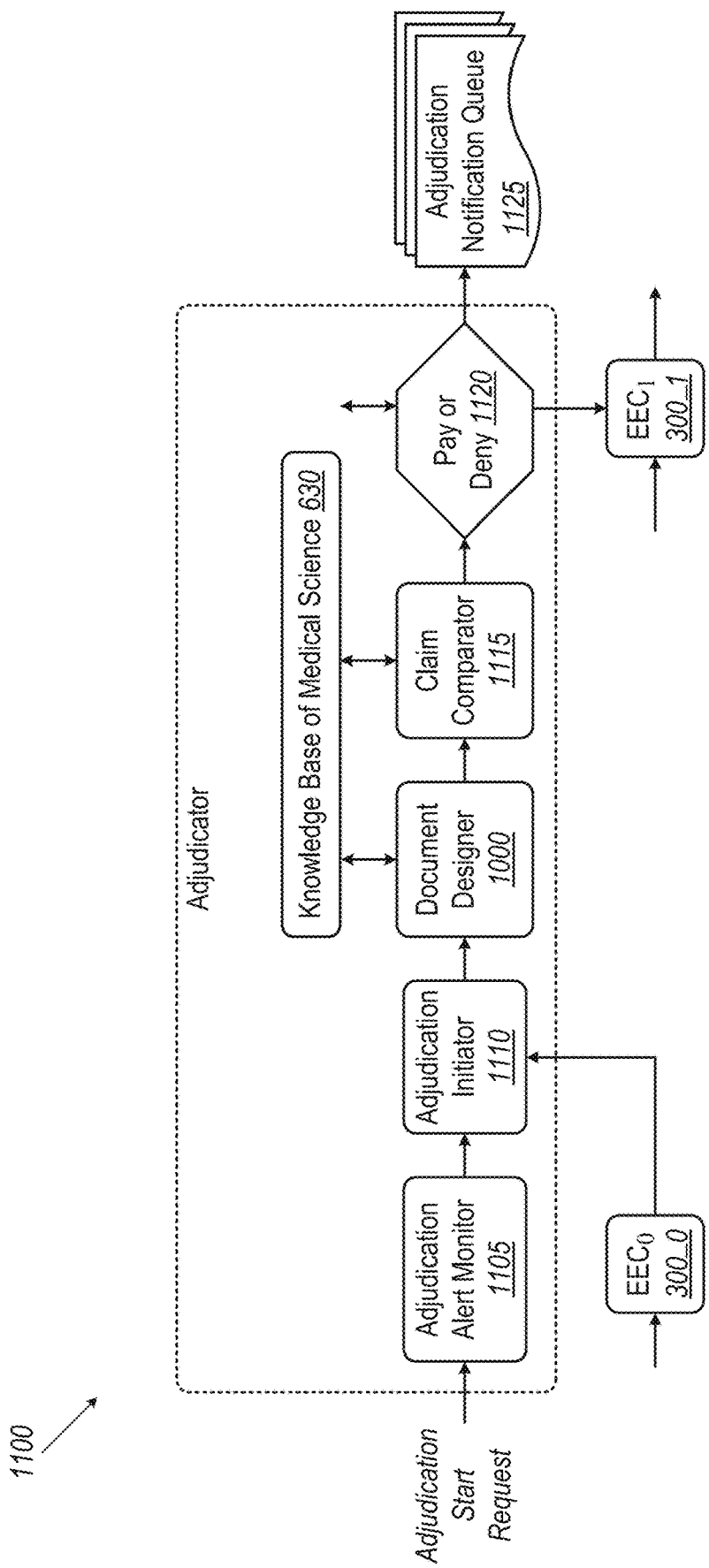
FIG. 14 is a flow diagram of an automated claim adjudicator in accordance with one or more embodiments of the present disclosure.

FIG. 14 is a flow diagram of an automated claim adjudicator 1100 in accordance with one or more embodiments of the present disclosure. The automated claim adjudicator 1100 may be implemented by the software modules executed by claim adjudication microservices 60 of FIG. 1 that may include an adjudication alert monitor 1105, an adjudication initiator 1110, the adjudication document designer 1000, a claim comparator 1115, and a pay or deny module 1120. The adjudication initiator 1110 may receive input data from the $EEC_0$ 300_0. The pay or deny module 1120 may output data to be stored in the $EEC_1$ 300_1. The adjudication document designer 1000, the claim comparator 1115, and the pay or deny module 1120 may bidirectionally communicate data with a Knowledge Base of Medical Science (KB-MS) 630.

In some embodiments, Claims Adjudication may be the process by which a submitted claim via the data stored in EEC 300 may be reviewed based upon medical necessity and the CMA platform 10 may decide to pay or deny the claim. This process is performed by the Claim Adjudicator 1100 subsystem in the Claim Adjudication Microservices 60 of FIG. 1. The Adjudicator Expert System 58 may use the contents of the case EEC 300 to make an independent determination of the medical necessity of the care delivered using only the knowledge from the KB-MS 630. The Adjudicator 1100 may use the adjudication document designer 1000 to synthesize a ranked list 1035 of complete and acceptable medical claims to support the claim evaluation as shown in FIG. 13.

In some embodiments, when the EEC 300 is submitted to the claim adjudication microservices 60, the at least one claim management processor 50 executing the EEC Unwrapper Module 56 may receive the EEC 300 and may unwrap the data container.

In some embodiments, adjudication processing begins with the reception of an Adjudication Start Request by the Adjudication Alert Monitor 1105. The Adjudication Alert Monitor 1105 may alert the CMA platform 10 to assign the Adjudication Initiator 1110 to process the event. The Adjudication Alert Monitor 1105 may then return to a state of waiting for a next Adjudication Start Request.

In some embodiments, the Adjudication Initiator 1110 may initialize the adjudication process by accessing the case data stored in the $EEC_0$ 300_0 to acquire the n consult packages 610-0, 610-1, . . . 610-n stored there by the Consult Recorder 540 and to load them into a process control structure. The Adjudication Initiator 1110 may relay the process control structure to the adjudication document designer 1000. The adjudication document designer 1000 used by the adjudication process may be substantially the same as the document designer 550 used in claims processing as described in FIG. 12. However, the difference between the adjudication document designer 1000 and the document designer 550 is that the components of the clinical consults, such as the language components, in the Physician Action category may be excluded by the query builder 1020 in generating the query set for the Seeker 1025.

In some embodiments, the query set with the excluded components may be relayed to the Seeker 1025 which may initiate an application programming interface (API) call to program the databases of the KB-MS 630 (e.g., KB BLOCKCHAIN DB 42 in FIG. 1) to seek medical necessity care delivery data in the databases to support the medical necessity of the care delivery based on the information in the query set and to transmit the medical necessity care delivery data back to the Seeker 1025.

Stated differently, in some embodiments, the plurality of patient-specific data elements with the physician's medical necessity justification, for example, from the physician's actions in the Table 800 of FIG. 11 in the EEC 300, may be excluded from the data inputted into the adjudicator expert system 58 (e.g., the second machine learning engine) and the (second) MLM model 62. Note that the automated claim document design steps may be substantially the same for the claim adjudicator expert system 58 (e.g., the second machine learning engine) to obtain the second ranked plurality of reference-claim document objects via the medical necessity scores (MNS). However, the physician's actions and/or justification for providing the at least one medical service to the patient may be deleted or removed by the least one processor 50 both in the query to the KB-MS 630 for obtaining the patient-specific medical-necessity information data objects and from the plurality of patient-specific data elements that are inputted into the second machine learning engine to obtain the second ranked plurality of reference-claim document objects.

In some embodiments, the Recipe Builder 1030 may use the identified medical necessity care delivery data for the query results acquired by the Seeker 1025 (e.g., retrieved medical necessity care delivery data) to assemble a ranked list of recipes 655 that describe documentation packages that may be used to support the medical necessity of the care delivery reported in the claim (e.g., the second ranked plurality of reference-claim document objects). The Recipe Builder 1030, using the Reference Claim Generator and Ranker Module 64 and the machine learning model 62, may rank the recipes into a ranked list of document packages including reference claims where the prescriptions for medication, treatment and therapy have been derived from the body of knowledge stored in the KB-MS 630. This ranked list may then be relayed to the Claim Comparator 1115.

In some embodiments, the Claim Comparator 1115 may use artificial intelligence algorithms that may be trained to evaluate correlation of the submitted claim document object with respect to the list of reference claims (e.g., the second ranked plurality of reference-claim document objects). If the pay or deny module 1129 may determine that there is sufficient correlation based on the reference claims according to an established criterion, the claim may be marked for payment. If there is not sufficient correlation, the claim may be marked as denied. The Claim Comparator 1115 results, and the supporting data, may then be stored in the case $EEC_1$ 300_1. Then, the completion of the Adjudication Process may be posted in an Adjudication Notification Queue 1125.

In some embodiments, the correlation between the submitted claim and reference claims may be based at least in part on the medical necessity scores. For example, with reference to the colonoscopy exemplary embodiment, if the physician chose to justify providing the colonoscopy on the basis of the patient having severe abdominal pains (MNS=30) only, the Claim Comparator 1115 and/or the pay or deny module 1129 may determine to reject the claim for payment. In contrast, if the physician chose to justify providing the colonoscopy on the basis of the patient having severe abdominal pains (MNS=30), a change in bowel habits (MNS=40), weight loss (MNS=60), a family history of colon cancer (MNS=70), and blood in the patient's stool (MNS=90) and then the physician removed cancerous polyps (MNS=99), the Claim Comparator 1115 and/or the pay or deny module 1129 may determine to approve the claim for payment.

Note that the colonoscopy exemplary embodiment is merely to provide conceptual and visual clarity that is not by way of limitation of the embodiments disclosed herein. The machine learning engines (e.g., the document design expert system 22 and/or the adjudicator expert system 58) may be trained, in fact, with terabytes of multivariate datasets based on, but not limited to, the plurality of diseases, signs and symptoms, abnormal findings, circumstances and external causes of diseases or injury found in the ICD-10 database, for example. These multivariate datasets may be used to train the machine learning engine to map the plurality of diseases, signs and symptoms, abnormal findings, circumstances and external causes of diseases or injury, as well as the corresponding medical necessity care delivery data and/or medical necessity scores (MNS) to a ranked set of plurality of reference-claim document objects which may be ranked based at least in part on the MNS scoring.

Figure 15:
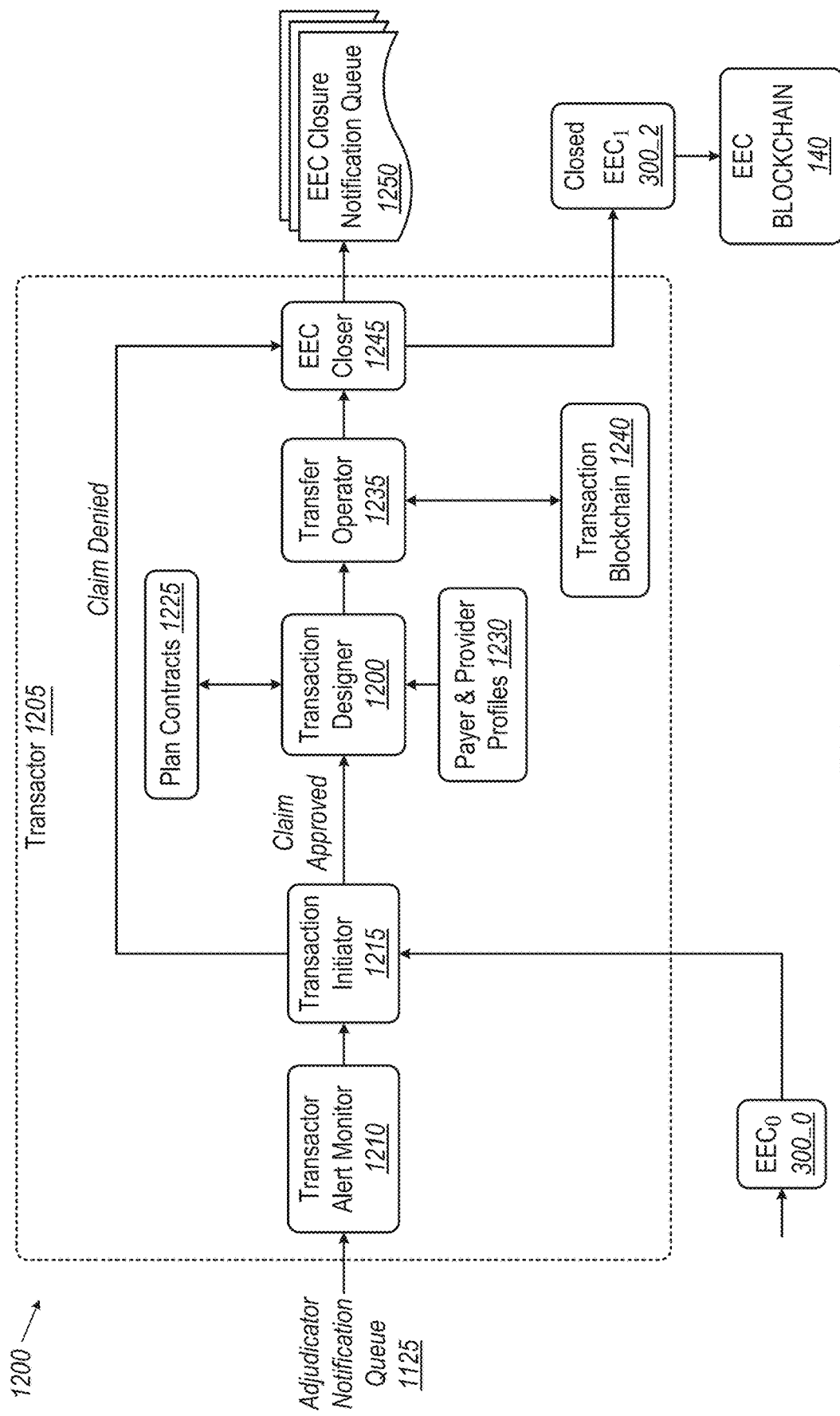
FIG. 15 is a flow diagram of a transactor in accordance with one or more embodiments of the present disclosure.

FIG. 15 is a flow diagram 1200 of a transactor 1205 in accordance with one or more embodiments of the present disclosure. The Payment Phase of Emergent Utilization is where the process of payment of an approved claim may be performed. This process may be executed by a Transactor subsystem 1205. The Transactor 1205 may be triggered by the posting of a new entry in the Adjudication Notification Queue 1125. This new entry event may be detected by a Transactor Alert Monitor 1210 that may monitor the Adjudication Notification Queue 1125 for a new entry. The Transactor Alert Monitor 1210 may alert the platform to assign a Transaction Initiator 1215 to process the new entry event. The Transactor Alert Monitor 1210 may then return to a state of monitoring the Adjudication Notification Queue 1125 for a new entry.

In some embodiments, the Transaction Initiator 1215 may first inspect the adjudication notification for the pay or deny status of the claim. If the claim is marked for denial, the Transaction Initiator 1215 may relay the processing to an EEC Closer 1245. The EEC Closer 1245 may mark the episode as complete, may store the result in a closed case $EEC_1$ 300_2, and may post an episode completion an EEC Closure Notification Queue 1250. This process may close the Emergent Episode and may conclude all case processing.

In some embodiments, if the posted claim is marked for payment, the Transaction Initiator 1215 may acquire the approved claim, and the patient's insurance plan information from the case EEC 300_0 so as to initialize the transaction process. the Transaction Initiator 1215 may relay this information and process execution to the Transaction Designer 1220.

In some embodiments, the Transaction Designer 1220 may interact with a Knowledge Base of Payer/Provider Contracts (KB-PPC) 1225 to determine the rate of payment for each of the services described in the claim, and to aggregate them into a single, itemized transaction description. The Transaction Designer 1220 may further acquire information for execution of the funds transfer from the payer and provider profiles 1230 and may combine the information with the transaction description to form a Transfer Package. Finally, the transfer package may be relayed to a Transfer Operator 1235.

In some embodiments, the Transfer Operator 1235 may use the information in the Transfer package to interact with the Utilization Management Transactions Blockchain 1240. The Transfer Operator 1235 may initiate a transfer of funds from the payer account to the provider account by interacting with the appropriate Smart Contract within the smart contract blockchain 71. When the funds transfer is complete, the completion data may be relayed to the EEC Closer 1245 which may store the completed transfer information in the closed case $EEC_1$ 300_2.

In some embodiments, in the final process of the last phase of Emergent Utilization, the EEC Closer 1245 may archive by storing the completed case EEC 300_2 in the EEC Blockchain 140. The EEC Closer 1245 may post the EEC Closure in the EEC Closure Notifications Queue 1250, thus completing the processing of the Emergent Episode in the CMA platform 10.

In some embodiments, any or all of the elements of the automated claim adjudicator 700 and/or the transactor 1205 (e.g., the transactor 68) may be implemented by the adjudicator expert system 58 in FIG. 1.

In some alternative embodiments related to FIG. 1, the adjudicator expert system 58 may include at least one inference engine, at least one machine learning model, or any combination thereof, for determining a level of the justified medical necessity for the provider having provided the medical services to the patient based on the plurality of payer-determination documentation files received from the medical knowledge base KB-MS 630 and the case specifics in the claim document file stored in the EEC 300. In other embodiments, the level of the justified medical necessity may be based on any assigned rank, score and any other suitable comparison metric outputted by the adjudicator expert system 58.

In some embodiments, the adjudicator expert system 58 may use a reference claim generator and ranker module 64 that uses the same data and information as does the Document Designer as previously described but generates, using the ranker 64, a ranked list 1035 of complete and acceptable medical claims also referred to herein as reference claim document files that may include the charge codes. The adjudicator expert system 58 may use algorithms to compare the data content of the provider-submitted claim document file to those in the ranked list of generated claims.

In some embodiments, the claim/reference claim comparator module 64 of the adjudicator expert system 58 may assign a justified medical necessity score based on the rankings to a comparison of the provider-generated claim document file and the plurality of reference claim document files. The claim/reference claim comparator module 64 may determine that the provider-generated claim document file is to be paid when the justified medical necessity score exceeds a predefined threshold;

In some embodiments, if the claim/reference claim comparator module 66 determines that the correlation is not sufficient, the claim may be denied. If there is sufficient correlation between the actual provider-submitted claim document file and the reference claim document files in the ranked list, the adjudicator expert system 58 may activate a blockchain "Smart Contract" 71, which may include the rates, fees and other agreements negotiated between the provider and payer, to determine the appropriate payment to the provider for the medical services rendered to the patient. The smart contract may generate a payment request in EEC 300.

In some embodiments, when payment to the provider is approved, the at least one processor 50 may trigger the transactor 68 (e.g., the transactor 1205). The transactor 68 may be implemented using the "Smart Contract" feature of blockchain technology. When a payment request is entered into the EEC 300, the smart contract 71 (e.g., the blockchain) may execute the electronic transfer of funds from the payer to the provider. The Transactor 68 may then notify both the provider and payer of the completed payment transaction such as via dashboards displayed on the GUIs (e.g., GUI 91A . . . 91B, and/or 96A . . . 96B) of any of the provider and payer computing devices (90A . . . 90B, and/or 95A . . . 95B).

In some embodiments, a Performance Monitor may be a third automated Expert System (ES) implemented by the at least one processor 50 that may use algorithms to perform real-time data analytics on the results of the Emergent Utilization operations in the platform 10 and stored in patient-related data containers (e.g., EEC 300). The Performance Monitor may be driven by a knowledge base for the evaluation of system performance. This knowledge base may be implemented in a blockchain infrastructure to store the completed Emergent Episode Containers 300, as well as the results of the analytic operations. The results of the Performance Monitor may be provided to KB-MS 630 for self-optimization.

The embodiments shown in FIG. 1 are merely for conceptual and visual clarity and not by way of limitation of the embodiments of the present disclosure. The claim management and adjudication platform 10 as shown herein is not limited to a patient seeking medical care in an emergency room but may also be applied to generating claims for a doctor visit, procedures performed in a surgicenter, receiving ambulatory care, and the like. For implementing the claim management and adjudication system as shown herein, the system architecture may be optimized to facilitate shared data between a medical payers and medical providers which may include network connected bio-medical instruments, consumer health devices and other systems that acquire and share data on the order of petabytes that are relayed via the API layer 100 to the claim management microservices orchestration system 15. The optimization for computation efficiency may impact how many computing machines and/or computing devices are used, and in what configuration they may be used to acquire, process, and/or store these petabytes of shared big data. These resources may be managed with the load balancer 130 and/or the resource manager 135. High-performance computing may enable the claim management and adjudication system with the capacity to store and to move large amounts data with high speed. The claim management and adjudication system may also leverage new generation of blockchain technology for reducing blockchain latency, for example. business process as a service (BPaaS).

The embodiments herein provide a technological solution to the automated management and adjudication of a plurality of medical claims involving processing petabytes of data. Trust between provider and payer may be provided (1) by the use of the microservices orchestration architecture shown in FIG. 1 and (2) by the use Blockchain technology for immutably storing the medical data, and for recording any actions performed by the providers, payers, stakeholders, or any combination thereof in the at least one blockchain ledger 120. All of the data records stored in blockchain technology may be functionally immutable, auditable and transparent as well as assessable to all stakeholders, but to no one else. In addition, the use of load balancing and resource management may further maximize the computational and load efficiencies of the computing systems associated with both the provider and payer by offloading these functionalities to the trusted claim management microservices orchestration system 15 as disclosed herein.

Figure 16:
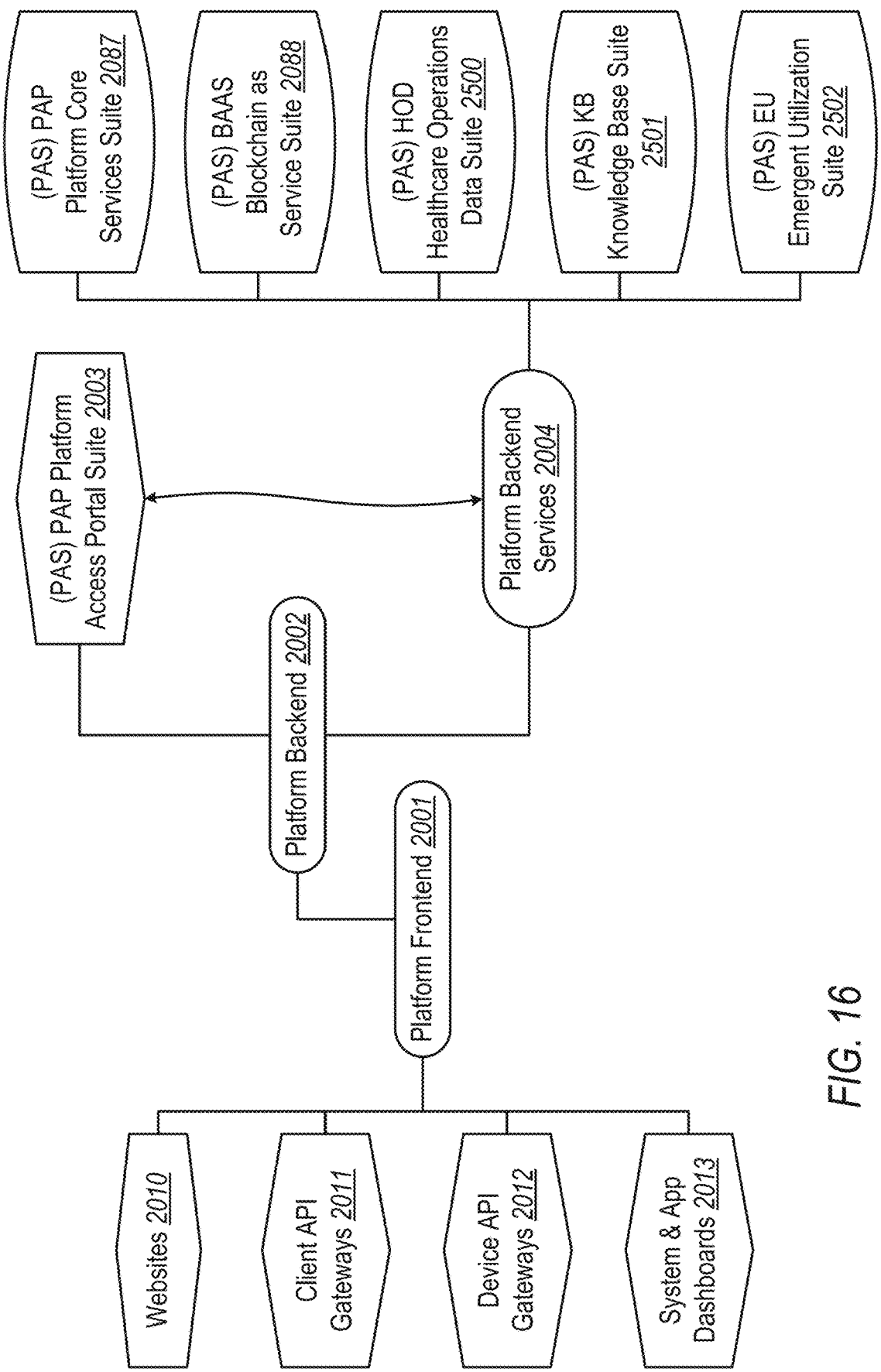
FIG. 16 is a top-level architecture diagram of a claim management and adjudication (CMA) Platform in accordance with one or more embodiments of the present disclosure.

FIG. 16 is a top-level architecture diagram of the CMA Platform 10 in accordance with one or more embodiments of the present disclosure. The CMA Platform 10 may be a cloud-native platform for the integration, digitization, and automation of healthcare operations. The CMA Platform 10 may be designed and/or implemented using advanced technologies from Google, Apple, the Linux Foundation, the Open Container Initiative, Docker, Kubernetes, and others. The CMA Platform 10 may provide the healthcare organization with the depth of control and flexibility that may be necessary to integrate, automate, and optimize its operations. The CMA Platform 10 may extensible into virtually any area of healthcare operations, and with sufficient infrastructure, may be massively scalable.

Note that the CMA Platform 10 may include a combination of hardware and software.

In some embodiments, the CMA Platform 10 may be a full stack, containerized, microservice based platform that may be partitioned into two primary functions. A Platform Frontend 2001 may include the interface devices presented to users that enable them to interact with the CMA Platform 10 and its features. A Platform Backend 2002 may include the applications that implement the platform's features.

In some embodiments, the Platform Backend 2002 may be further divided into two major blocks. A Platform Access Portal 2003 may implement the interfaces for controlled access to the CMA Platform 10 and may make those interfaces available to users through the Platform Frontend 2001, and a Platform Backend Services 2004 block which may include the applications that may implement the rest of the platform features and operations. The Platform Backend Services 2004 may be internal to the platform infrastructure and may be accessible to general users through the Platform Access Portal 2003.

In some embodiments, a key design construct of the CMA Platform 10 may be a Platform Application Suite (PAS). A PAS may include a complete microservice application that may implement a feature or operation on the platform. It may be a hierarchical structure of orchestrated services that implement the platform feature. A PAS may run natively on the CMA Platform 10 and may interact directly with other PAS blocks running on the platform. There may be multiple PAS blocks running on the CMA Platform 10 at any time.

In some embodiments, there may be specialized versions of PAS blocks. A Platform Automation Receptor (PAR) may implement an automated interface for the integration of a Third-Party Service Application into the platform. A Remote Device Receptor (RDR) may implement an automated interface for the integration of a Remote Smart Device into the CMA Platform 10.

In some embodiments, Emergent Utilization may be implemented on the CMA Platform 10 as a Platform Application Suite. The application features may be organized into three Platform Applications Suites, (1) a Knowledge Base PAS (KB) 2501, (2) an Emergent Utilization PAS (EU) 2502, and (3) a Blockchain as a Service PAS (BaaS) 2088. The Knowledge Base of Medical Science (KB-MS) 630 may be included within the Knowledge Base Platform Application Suite 2501.

In some embodiments, the Platform Frontend 2001 may implement the interfaces that may be presented to users of the platform, including system administrators, consumers, and devices, to enable them to interact with the platform applications and to use its operations. The Platform Frontend 2001 may present multiple interfaces in the form of web sites, API gateways and dashboards. These interfaces may fall into four groups that reflect the structure of the Platform Backend 2002 features that support them. These groups may be designated as Websites 2010, Client API Gateways 2011, Device API Gateways 2012, and System and Application Dashboards 2013 as shown in FIG. 16.

Figure 17:
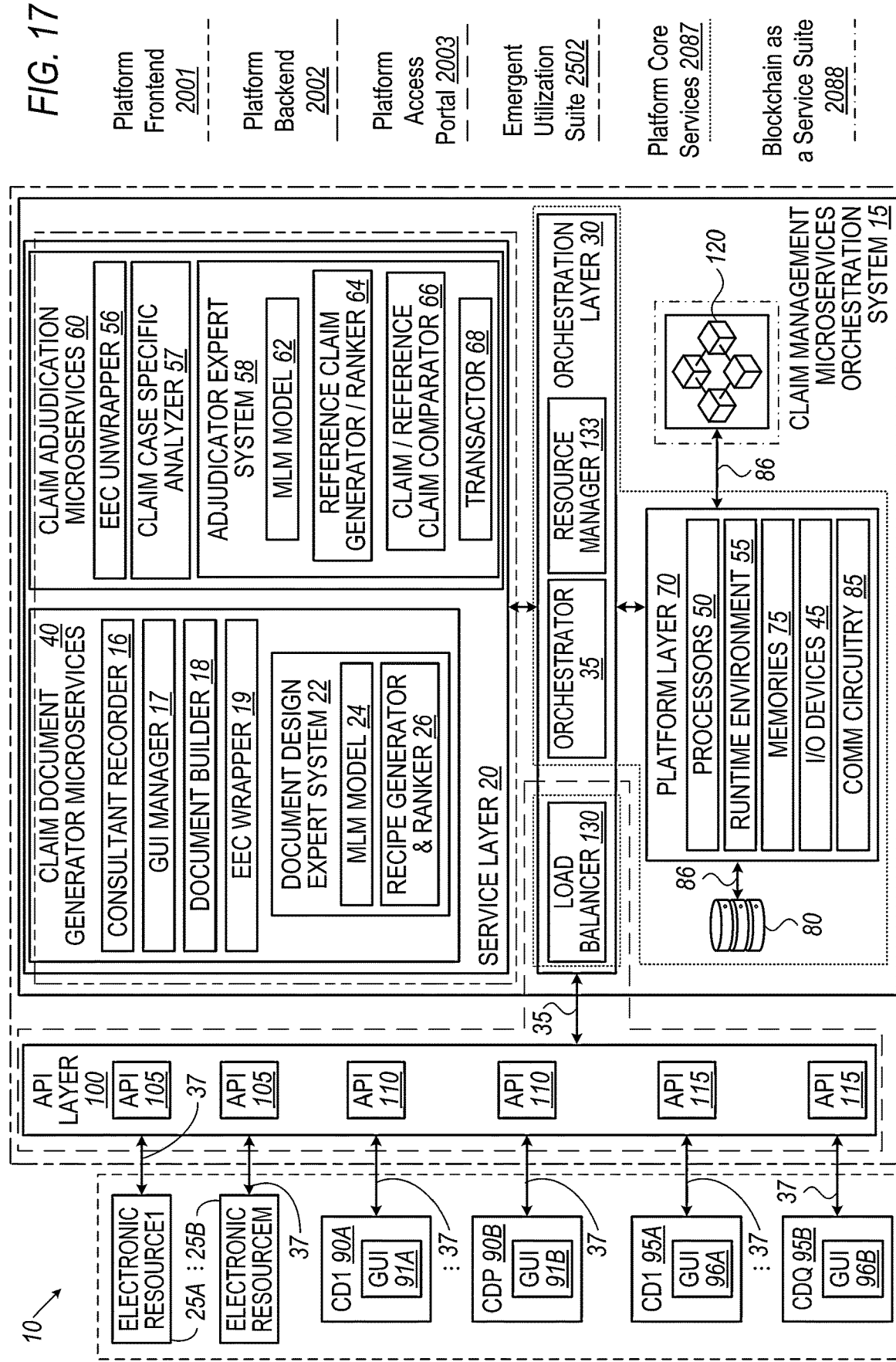
FIG. 17 is a highlighted block diagram of a CMA Platform in accordance with one or more embodiments of the present disclosure.

FIG. 17 is a highlighted block diagram of the CMA Platform 10 in accordance with one or more embodiments of the present disclosure. Note that the elements in the block diagram of CMA Platform 10 as shown in FIG. 1 are mapped into the elements and blocks shown in FIG. 16 merely for conceptual and visual clarity in linking the two representations of the CMA Platform 10 as disclosed herein. Stated differently, the dash type legend of highlight lines on the right side of FIG. 17 illustrates the portions of the FIG. 1 block diagram that are part of the platform frontend 2001, the platform backend 2002, the platform access portal 2003, the emergent utilization suite 2502, the platform core services 2087, and the blockchain as a service suite 2088 as shown in FIG. 16.

In some embodiments, in the CMA Platform 10, the plurality of backend devices in the platform layer 70 may be configured to execute the platform access portal 2003 (including the at least one electronic resource API 105, the at least one provider API 110, and/or the at least one payer API 115 in the API layer 100), the blockchain as a service suite 2088, and the emergent utilization suite 2502 including the claim document generator microservice 40 and/or the claim adjudication microservice 60.

Figure 18:
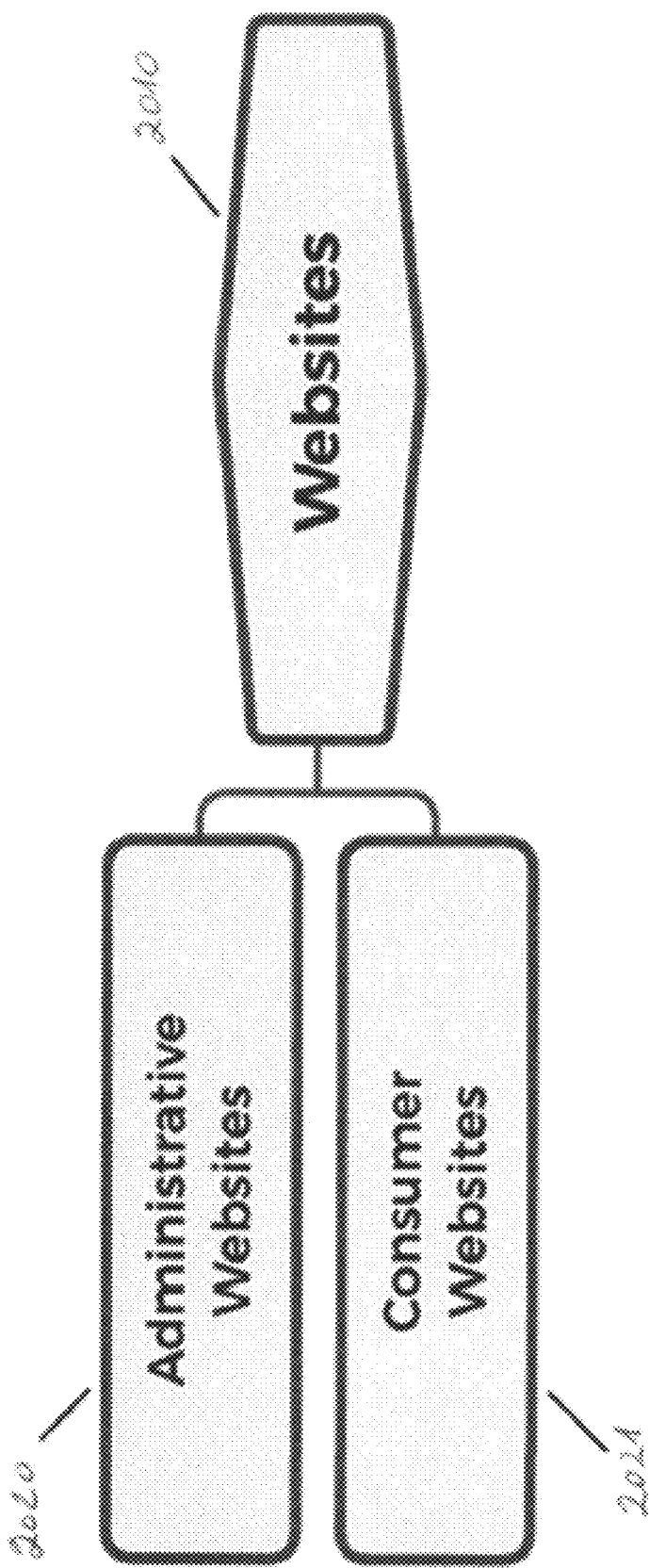
FIG. 18 is a block diagram illustrating websites in the platform frontend in accordance with one or more embodiments of the present disclosure.

FIG. 18 is a block diagram illustrating websites in the platform frontend in accordance with one or more embodiments of the present disclosure. Many of the features and operations available on the CMA Platform 10 may be made available through frontend Websites 2010, making them accessible from an internet web browser such as Safari, Microsoft Edge, Firefox, Chrome, and others. These interfaces may be implemented and may be exposed for external access by the web server applications that may be implemented in the Platform Backend 2002. The websites may include but are not limited to Administrative Websites 2020, having full access to the capabilities implemented by the Platform Backend 2002, and Consumer Websites 2021 providing restricted access.

In some embodiments, the CMA Platform 10 may implement a web server function and may be configured to initially present at least one web page, typically a home page, that identifies the application and describes its features and functions.

Figure 19:
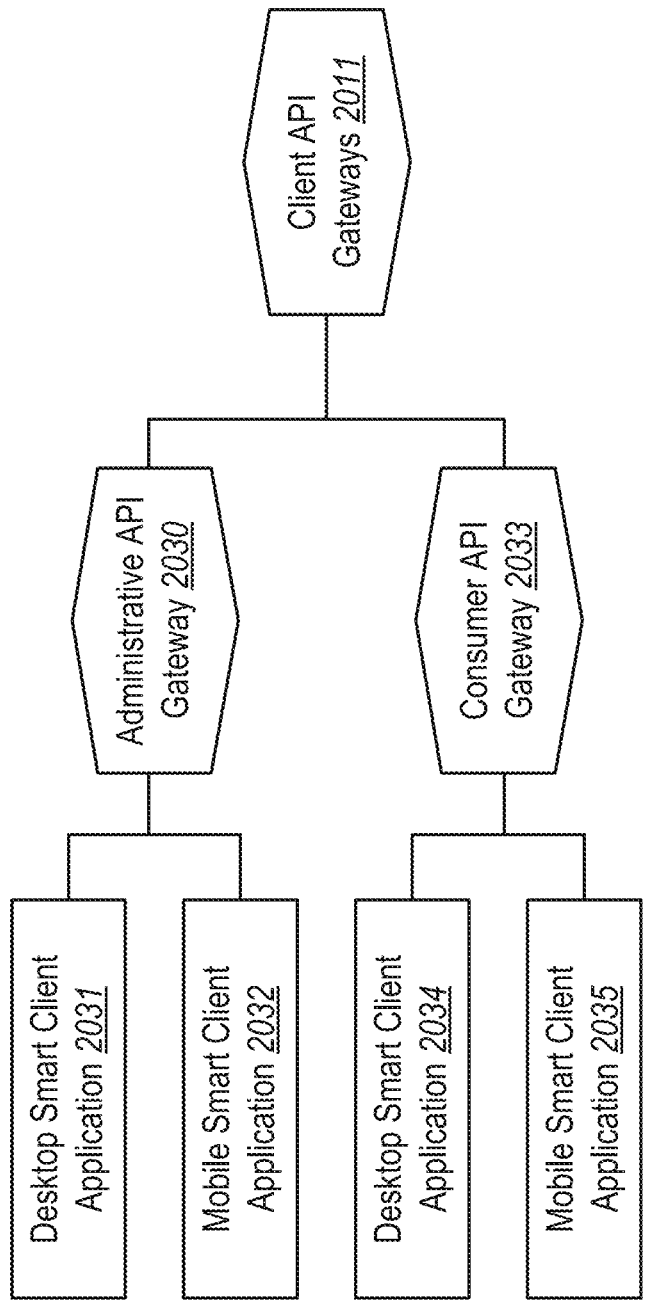
FIG. 19 is a block diagram illustrating client API gateways in the platform frontend in accordance with one or more embodiments of the present disclosure.

FIG. 19 is a block diagram illustrating client API gateways in the platform frontend in accordance with one or more embodiments of the present disclosure. More complex and demanding applications may require capabilities beyond those of a common web browser. Such applications may employ "edge-processing", for example, where some of the application's features may be implemented on the user's desktop or mobile device, so as to leverage their computational resources. At scale, these client-side resources may bare substantial portions of the application's computational load and may reduce the size and cost of the backend infrastructure, while improving the overall system performance, and presenting a better user experience. To accommodate such applications, the Platform Frontend 2001 may implement the Client API Gateways 2011. These gateways may provide a means for complex applications to implement a smart client application component to run on a user device and may absorb a portion of the application's computational load, while interacting with the main application services running on the Platform Backend 2002 through the Client API Gateway 2011.

In some embodiments, there may be two categories of the Client API Gateway 2011. The Administrative API Gateway 2030 may provide full access to application features by an administrative Desktop Smart Client Application 2031, and an administrative Mobile Smart Client Application 2032. The Consumer API Gateway 2033 may provide restricted access to application features by consumer desktop and mobile smart client applications 2034 and 2035 respectively.

Figure 20:
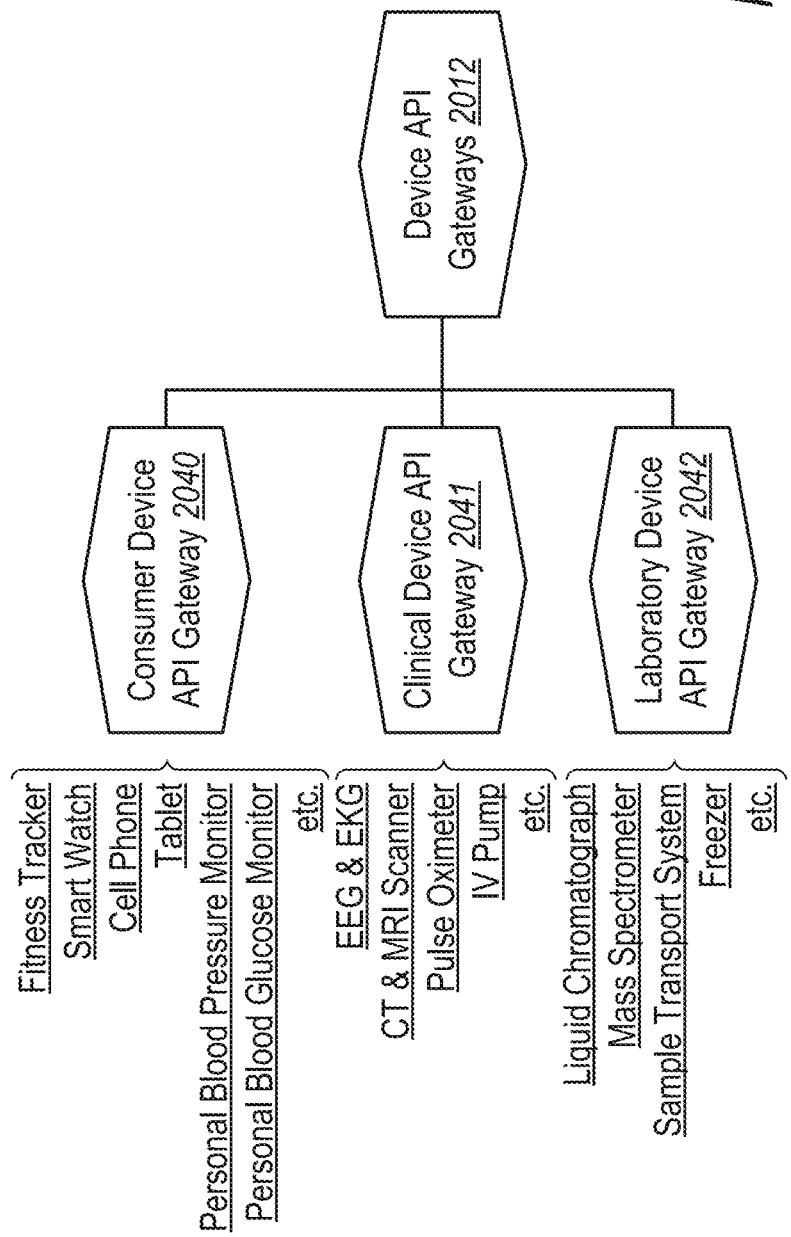
FIG. 20 is a block diagram illustrating device API gateways in the platform frontend in accordance with one or more embodiments of the present disclosure.

FIG. 20 is a block diagram illustrating device API gateways in the platform frontend in accordance with one or more embodiments of the present disclosure. The CMA Platform 10 may include capabilities for the integration of remote, intelligent devices into native platform operations through its Device API Gateway 2012. Through this interface, remote devices may connect to an application running on the CMA Platform 10 over the internet or other network. These devices may receive commands from or send commands to the application and may also transfer or stream data to or from the platform application. These remote interactions may be automated and integrated into multiple healthcare system operations supported by other applications running on the platform, in real-time. The Device API Gateway 2012 may be divided into, but not limited to, three sub-gateways.

In some embodiments, the Consumer Device API Gateway 2040 may enable user smart devices to interface with the platform. This may include a myriad of devices, such as but not limited to fitness trackers, smart watches, tablet devices, and personal health monitors as shown in FIG. 20.

In some embodiments, the Clinical Device Gateway 2041 may provide platform application access to smart devices installed in a clinical setting such as a hospital, physician's office, and/or outpatient clinic. These devices may include, but are not limited to EEG and EKG machines, cardiac monitors, ventilators, pulse oximeters, for example. Clinical devices may connect to the platform via secured networks installed within a healthcare facility.

In some embodiments, the Laboratory Device API Gateway 2042 may provide platform application access to intelligent clinical laboratory devices such as sample transport systems, liquid chromatographs, mass spectrometers, freezers, for example. Laboratory devices may connect to the platform via networks installed within or between healthcare facilities.

In some embodiments, modern, distributed, cloud-based applications and their infrastructures may combine to form very complex systems. The high-availability, performance, and reliability of these systems may be essential to critical operations and to the user experience. As these systems scale-up, it may be necessary to employ automated tools to measure and record the status and performance of the platform as a whole, as well as each system component, whether hardware or software, in real-time to assist system administrators in the maintenance and life cycles of these systems.

In some embodiments, the CMA Platform 10 may use Prometheus, an open-source tool for the automated, real-time acquisition and recording of system metrics. Metrics are data posted by a component of the system, regarding its status and performance. These metrics may be posted at a standard HTTP endpoint where they may be queried by the Prometheus tool. The CMA Platform 10 may use Grafana, another open-source tool, to graphically display the data from the Prometheus database to the user in a meaningful form. These dashboards may be used by the system administrators and others to maintain and troubleshoot the system. This is the functionality provided by the System and Applications Dashboards 2013 of the Platform Frontend 2001.

In some embodiments, there may be many system metrics that Prometheus may acquire "out-of-the-box", but there may be many application-specific metrics that are needed to support system maintenance. Therefore, every application and service implemented on the CMA Platform 10 may implement a/metrics HTTP endpoint to enable metrics acquisition by Prometheus, as well as a/health endpoint to enable a basic check of the operation of the service with a simple HTTP get request.

Figure 21:
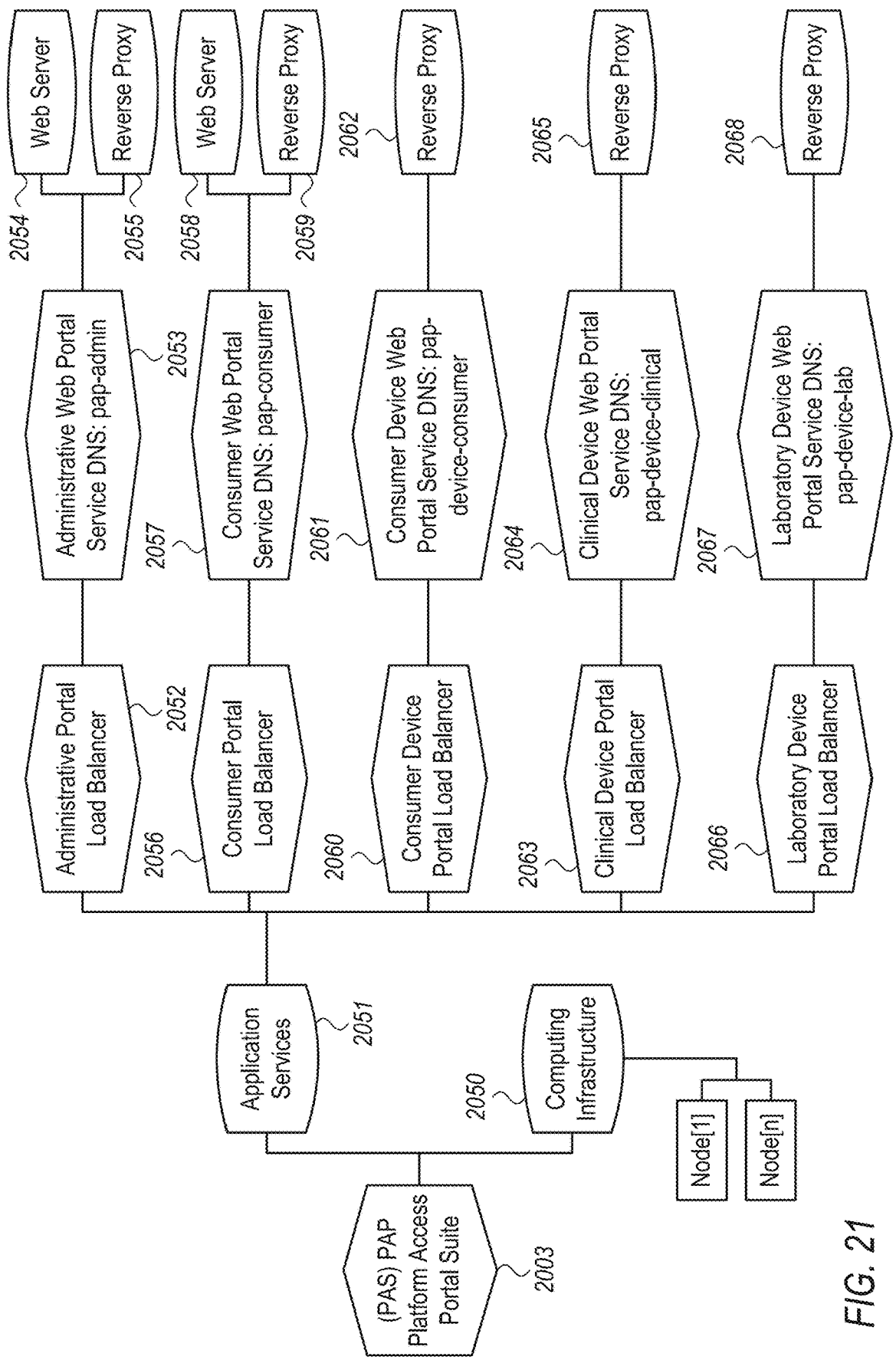
FIG. 21 is a block diagram illustrating a platform access portal in accordance with one or more embodiments of the present disclosure.

FIG. 21 is a block diagram illustrating a platform access portal 2003 in accordance with one or more embodiments of the present disclosure. The Platform Access Portal (PAP) 2003 may include the interfaces for controlled access to, and interaction with the Platform Backend Services 2004 for external users of the platform. The interfaces implemented within the PAP 2003 may be accessible to the Platform Frontend 2001 for presentation to users.

In some embodiments, the PAP 2003 may be implemented using the open-source version of NGINX, a product developed by F5. NGINX may be used to implement various features of the PAP 2003, which include, but are not limited to, the web servers and API gateways that are made available to the Platform Frontend 2001, and the load balancers that traffic the user requests coming into the platform as shown in FIG. 21.

In some embodiments, the Platform Access Portal 2003 may be implemented within a larger datacenter infrastructure, or standalone on a separate Computing Infrastructure 2050 that may include a least one computing node, with each node having at least one central processing unit (CPU), non-transient computing memory, and/or storage resources. The PAP 2003 may be connected to the platform backend network enabling it to communicate with the Platform Backend 2002 applications. The PAP 2003 may also be connected to the Platform Frontend 2001 which may include connection to the external networks which users and devices use to access the platform. These external networks may include but are not limited to the world-wide-web (the internet), and the healthcare organization's internal network infrastructure.

The Application Services 2051 implemented within the PAP 2003 may include but are not limited to web portals for administrative, consumer, and device access to the Platform Backend Services 2004.

In some embodiments, the Administrative Web Portal 2053 of the Platform Access Portal 2003 may provide access to the applications and operations in the Platform Backend Services 2004 that may implement external web interfaces. The Administrative Web Portal 2053 may be implemented using NGINX and may be preceded by the Administrative Portal Load Balancer 2052 as shown in FIG. 21 that manages the traffic of incoming network request among one or more instances of the Administrative Web Portal 2053 service. The service may include a Web Server 2054 for web browser access, and a Reverse-Proxy interface 2055 that may provide routing of incoming network requests to the appropriate application and the application's API interface.

In some embodiments, the web portal functions may not include the implementation of the API (Application Programming Interface) for any application running on the platform. The API for a given platform application may be implemented within the application where it is the responsibility of the application developer. Any web portal that is implemented by a web server may present at least one web page, which may be a home page for the application.

In some embodiments, the Consumer Web Portal 2057 of the Platform Access Portal 2003 may provide restricted access to the applications and operations in the Platform Backend Services 2004 that implement external interfaces. The Consumer Web Portal 2057 may be implemented using NGINX and may be preceded by the Consumer Portal Load Balancer 2056 that manages the traffic of incoming network request among one or more instances of the Consumer Web Portal 2057 service as shown in FIG. 21. The service may include a Web Server 2058 for web browser access, and a Reverse-Proxy interface 2059 that may provide routing of incoming network requests to the appropriate application and its API interface.

In some embodiments, the web portal functions may not include the implementation of the API (Application Programming Interface) for any application running on the platform. The API for a given platform application may be implemented within the application and is the responsibility of the application developer. Any web portal that is implemented by a web server may present at least one web page, which may be a home page for the application.

In some embodiments, the Consumer Device Web Portal 2061 of the Platform Access Portal 2003 may provide access to the applications and operations included in the Platform Backend Services 2004 that may implement interfaces for external, remote consumer device interaction. The Clinical Device Web Portal 2061 may be implemented using NGINX and may include the Consumer Device Portal Load Balancer 2060 that may manage the distribution of incoming network request among one or more instances of the Consumer Device Web Portal service 2061, which may include a Reverse-Proxy interface 2062 for routing of incoming network requests to the appropriate application in the Platform Backend Services 2004. The web portal functions may not include the implementation of the API (Application Programming Interface) for any application running on the platform. The API for a given platform application may be implemented within the application, which may be the responsibility of the application developer.

In some embodiments, the Clinical Device Web Portal 2064 of the Platform Access Portal 2003 may provide access to all the applications and operations included in the Platform Backend Services 2004 that may implement interfaces for external, remote clinical device interaction. The Clinical Device Web Portal 2064 may be implemented using NGINX and may include the Clinical Device Portal Load Balancer 2063 that may manage the distribution of incoming network request among one or more instances of the Clinical Device Web Portal service 2064, which may include a Reverse-Proxy interface 2065 for routing incoming network requests to the appropriate application in the Platform Backend Services 2004.

In some embodiments, the web portal functions may not include the implementation of the API (Application Programming Interface) for any application running on the platform. The API for a given platform application may be implemented within the application, which may be the responsibility of the application developer.

In some embodiments, the Laboratory Device Web Portal 2067 of the Platform Access Portal 2003 may provide access to all the applications and operations included in the Platform Backend Services 2004 that may implement interfaces for external, remote laboratory device interaction. The Laboratory Device Web Portal 2067 may be implemented using NGINX and may include the Laboratory Device Portal Load Balancer 2066 that may manage the distribution of incoming network request among one or more instances of the Laboratory Device Web Portal service 2067, which may include a Reverse-Proxy interface 2068 for routing incoming network requests to the appropriate application in the Platform Backend Services 2004.

In some embodiments, the Laboratory Device Web Portal 2067 of the Platform Access Portal 2003 may provide access to the applications and operations in the Platform Backend Services 2004 that may implement interfaces for interaction with remote, laboratory devices. The Laboratory Device Web Portal 2067 may be implemented using NGINX and may be preceded by the Laboratory Device Portal Load Balancer 2066 that manages the traffic of incoming network request among one or more instances of the Laboratory Device Web Portal 2067 service as shown in FIG. 21. The service may include a Reverse-Proxy interface 2068 that provides routing of incoming network requests to the appropriate application and its API interface. The web portal functions may not include the implementation of the API (Application Programming Interface) for any application running on the platform. The API for a given platform application may be implemented within the application, which may be the responsibility of the application developer.

In some embodiments, the addition of a new service application to the Platform Backend Services may also require the addition of one or more interfaces to enable consumption of the new feature by external users or devices. To accommodate this need, the Platform Access Portal 2003 may be extendable in two ways. The first way may be to develop additional interfaces within one or more of the default Platform Access Portal 2003 web portals (administrative, consumer or device). The second way may be to develop a completely new web portal and load balancer that may be added to the PAP 2003.

Figure 22:
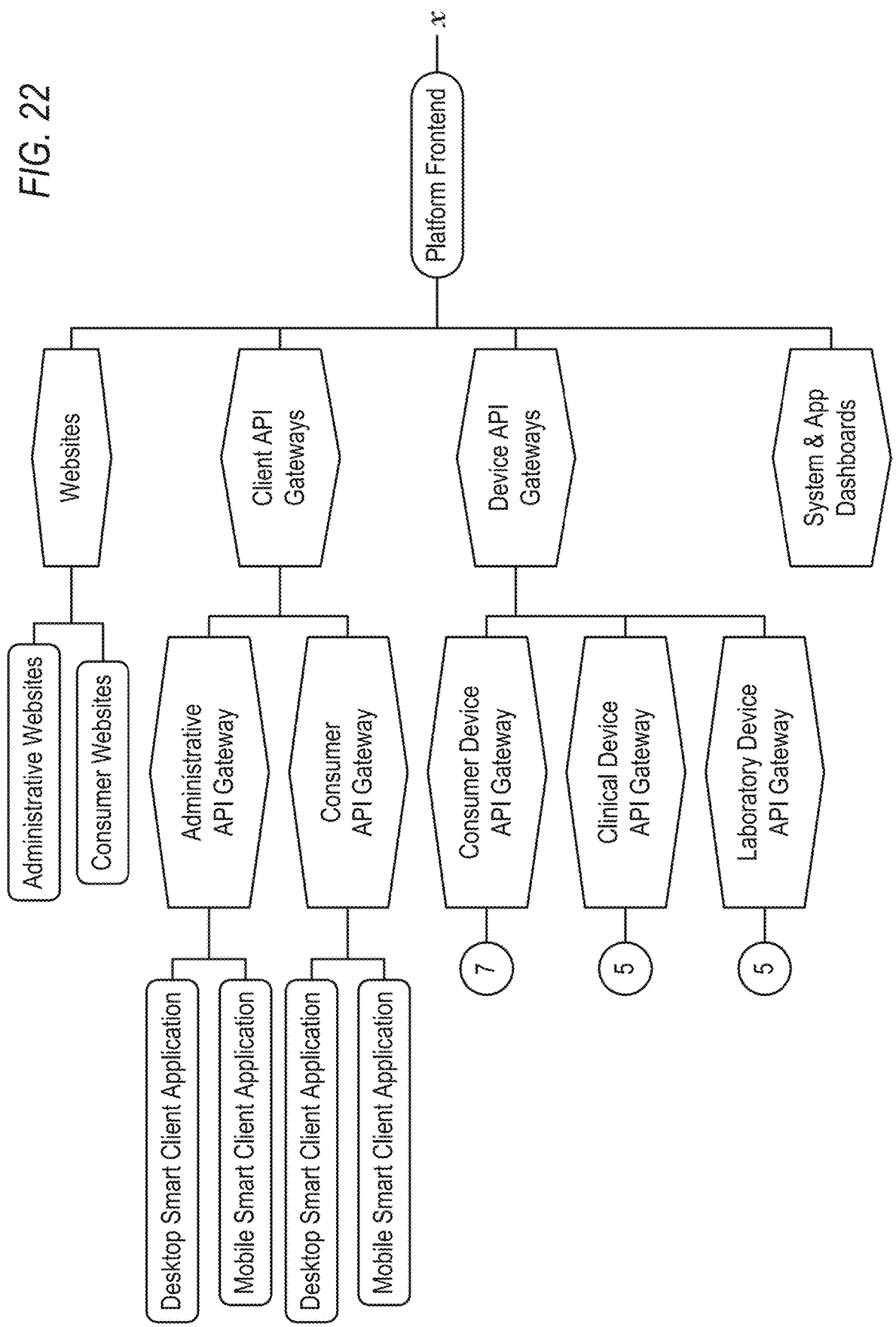
FIG. 22 is a block diagram of the overall platform design for user access to the platform in accordance with one or more embodiments of the present disclosure.
Figure 22:
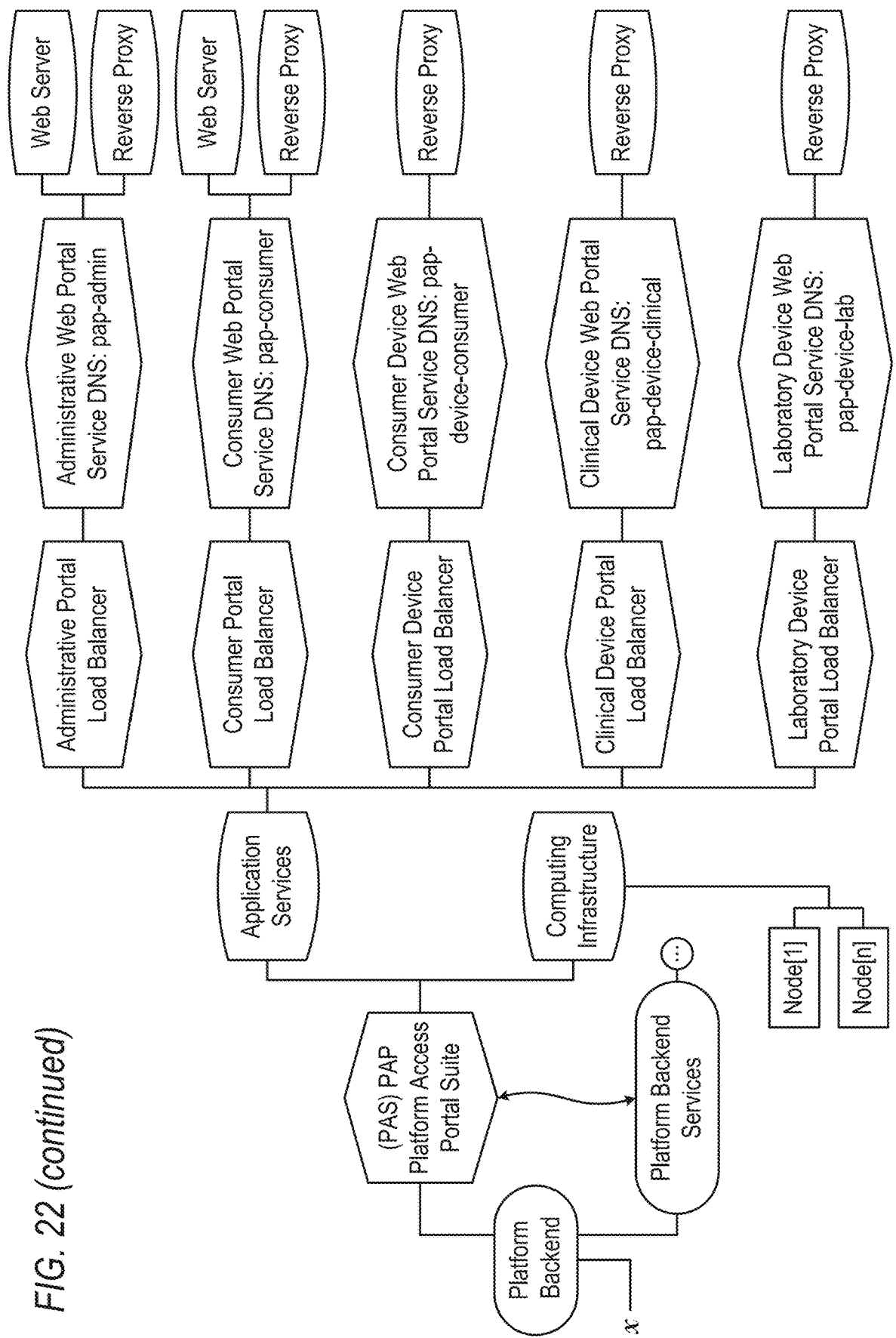

FIG. 22 is a block diagram of the overall platform design for user access to the platform in accordance with one or more embodiments of the present disclosure. The features of the Platform Frontend 2001 may be mapped to the features implemented in the Platform Access Portal 2003 of the Platform Backend 2002. Together, they implement the overall platform design for user access. A summary diagram of this design may be presented in the embodiments shown in FIG. 22.

Figure 23:
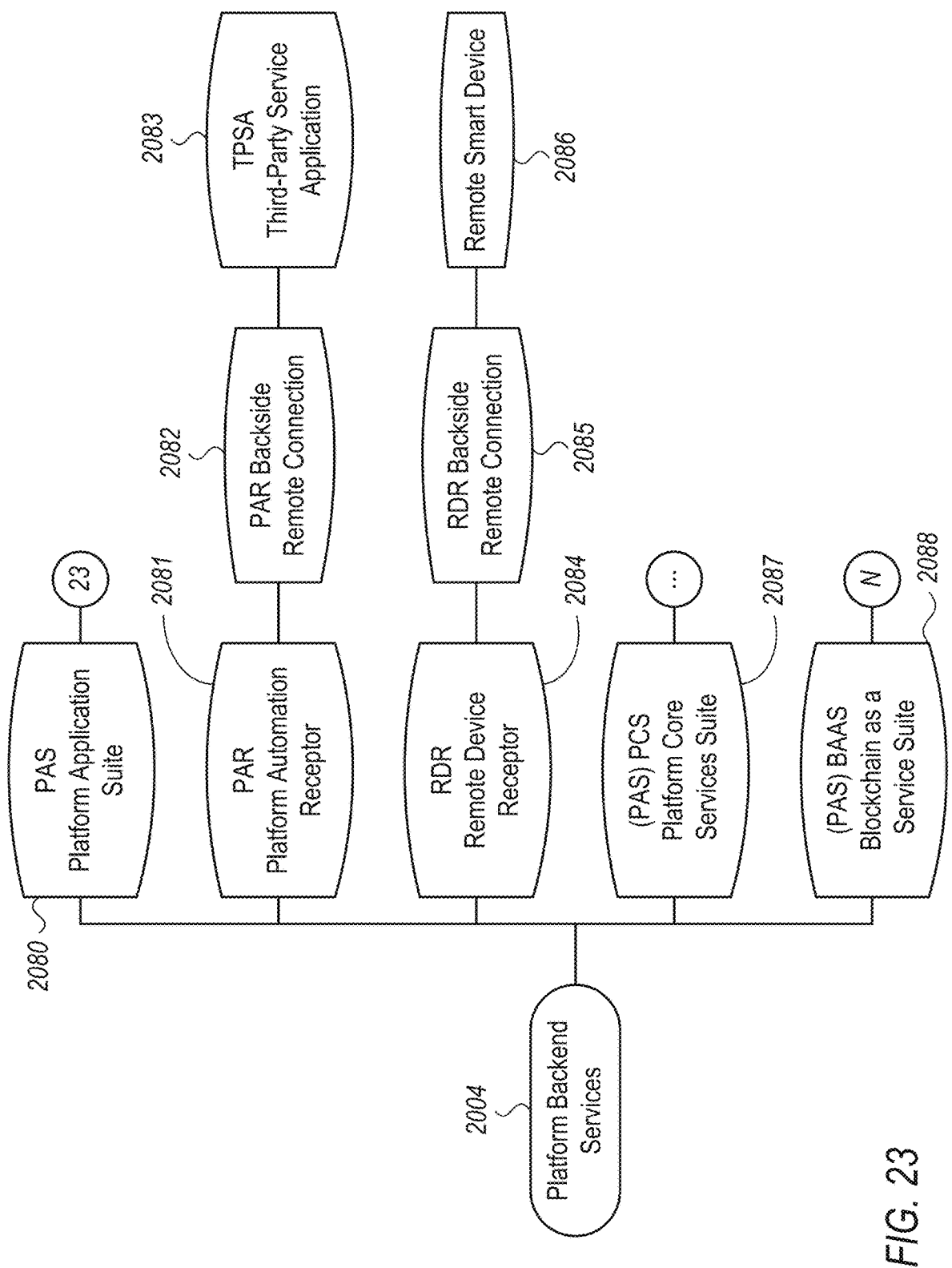
FIG. 23 is a block diagram illustrating platform backend services architecture in accordance with one or more embodiments of the present disclosure.

FIG. 23 is a block diagram illustrating platform backend services architecture in accordance with one or more embodiments of the present disclosure. The Platform Backend Services 2004 may include all the Platform applications and operations, except for the Platform Access Portal 2003. The Platform Backend Services 2004 may be implemented within the Platform's infrastructure and may not be externally accessible. External access to Platform Backend Services 2004 may be provided by the Platform Access Portal 2003 and presented to users through the Platform Frontend 2001.

In some embodiments, the Platform Backend Services 2004 may be laid out as a hierarchically structured, microservice ecosystem. The top-level component of the Platform Backend Services 2004 architecture may be a grouping of services called an Application Suite. An application suite may be a hierarchical structure of services that may embody a complete platform feature. There may be three types of application suite defined for the platform: a Platform Application Suite 2080, a Platform Automation Receptor 2081, and a Remote Device Receptor 2084.

In some embodiments, the Platform Application Suite (PAS) 2080 may include a complete microservice application implementing a feature or operation on the platform. The PAS 2080 may include multiple orchestrated services running together to implement the platform feature. The PAS 2080 may run natively on the Platform and may utilize various core platform resources, as well as interact directly with other Platform Application Suites running on the platform. There may be multiple Platform Application Suites running on the Platform at any time.

In some embodiments, the Platform Automation Receptor (PAR) 2081 may include a complete microservice application implementing an automated interface for the integration of a Third-Party Service Application 2083 into the CMA Platform 10. This feature may enable the data from disparate (external) sources, applications, and systems to be natively integrated into the Platform, to utilize platform resources, and to be interoperable with other PAS's running on the platform, in the same manner as would a native PAS 2080. The PAR 2081 may be a specialized version of a PAS 2080, that may communicate with the Third-Party Service Application 2083 over a direct communications link, referred to as a PAR Backside Remote Connection 2082. A PAR 2081 may enable the Platform to have complete control of one side of the integration interface to the Third-Party Service Application 2083. There may be multiple PAR's running on the Platform at any time.

In some embodiments, the Remote Device Receptor (RDR) 2084 may include a complete microservice application implementing an automated interface for the integration of a Remote Smart Device 2086 into the Platform. This feature may enable smart devices like fitness trackers, watches, cell phones, and tablets, as well as clinical and laboratory equipment to be natively integrated into the Platform, and to be interoperable with PAS's running on the platform. The RDR 2084 may be a specialized version of a PAS 2080, that may communicate with the Remote Smart Device 2086 over a direct communications link, referred to as a RDR Backside Remote Connection 2085. There may be multiple RDR's running on the Platform at any time.

Note that the Platform Access Portal 2003 may be implemented as a PAS. It may be treated separately due to its unique role as the bridge between the Platform Frontend 2001 and the Platform Backend 2002.

In some embodiments, there may be three Platform Application Suites (PAS's) 2080 that may define components of the Platform. The first two PAS's: the Platform Access Portal (PAP) 2003 and the Platform Core Services Suite (PCS) 2087 may include a standard set of external interfaces, features, and operations that may be needed for any system developed as described herein. These features and operations may also establish a set of standard resources that may be available to any service running on the platform. As the combination of these applications suites implement key references for the platform operation, they may be considered to be an operational source of truth for the platform. Hence, there may be only one instance of the PAP 2003 and PCS 2087 running on the platform at any time.

In some embodiments, the third PAS may be the Blockchain as a Service Suite (BAAS) 2088. The BAAS 2088 may be a blockchain based, distributed ledger system that is designed to meet the unique healthcare operations requirements of the platform as described herein. Each of these Platform Application Suites are described in subsequent sections of this disclosure.

Figure 24:
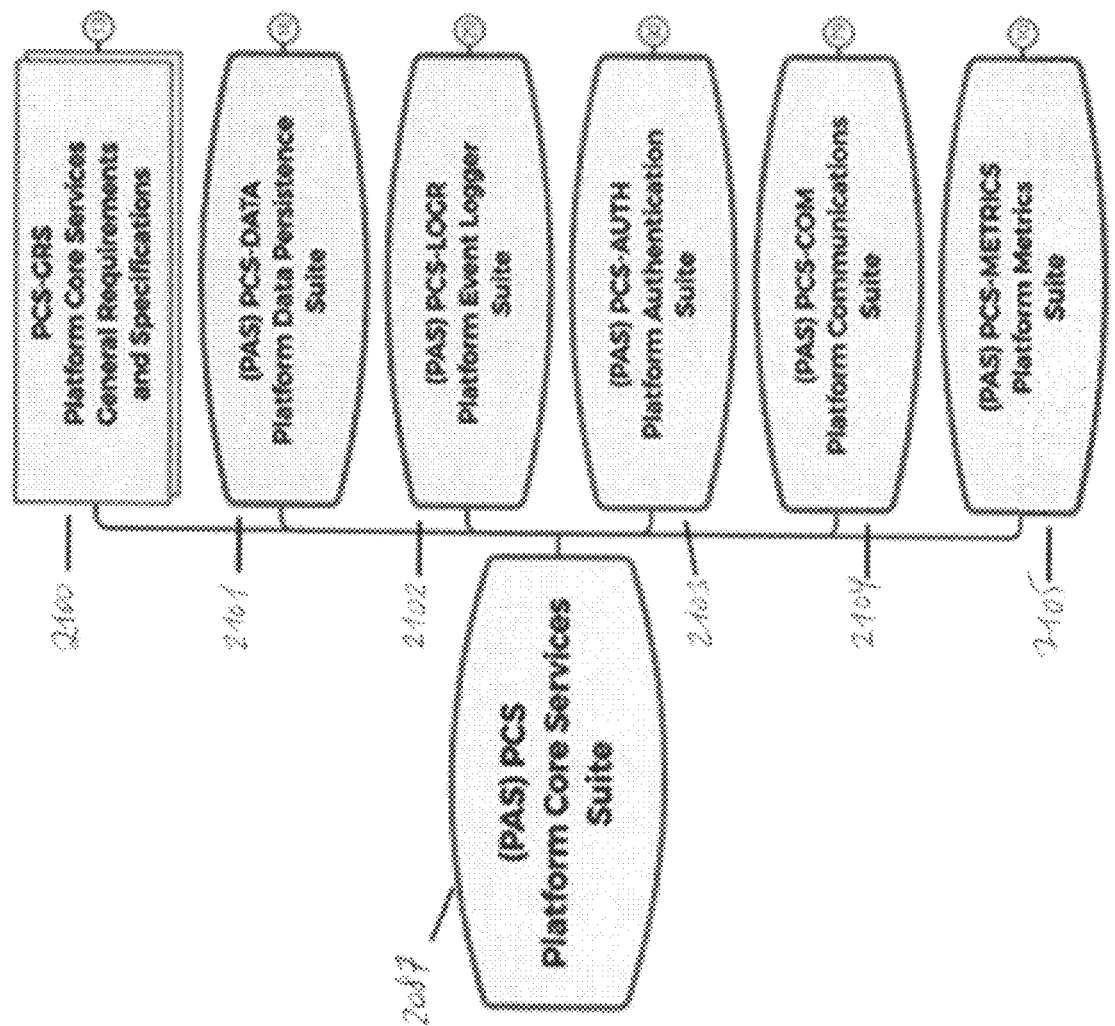
FIG. 24 is a block diagram illustrating a microservice core platform suite in accordance with one or more embodiments of the present disclosure.

FIG. 24 is a block diagram illustrating a microservice core platform suite in accordance with one or more embodiments of the present disclosure. The Platform Core Services Suite 2087 (PCS) may be a containerized, microservice application that implements "core platform" features and resources as shown in FIG. 24. These platform-defined features and resources may be made available to any application running on the Platform. As described above, there may be only one PCS 2087 running on the platform at any time.

In some embodiments, the PCS 2087 specification may include a set of General Requirements and Specifications (PCS-GRS) 2100 that may be used in the design of the PCS 2087 services. The PCS 2087 services include, but are not limited to:

1. A Platform Data Persistence Suite (PCS-DATA) 2101 may provide resources for service data persistence. In some embodiments, these resources may include relational and document database services.
2. A Platform Event Logger Suite (PCS-LOGR) 2102 may be a customizable, temporal event logging service.
3. A Platform Authentication Suite (PCS-AUTH) 2103 may implement user and device authentication services, and administrative and consumer access controls.

4. A Platform Communications Suite (PCS-COM) 2104 may provide notification and messaging services.
5. A Platform Metrics Suite (PCS-METRICS) 2105 may implement real-time monitoring and the recording of infrastructure and application metrics to support system security, maintenance, and reliability engineering Note that the following sections of this disclosure include detailed descriptions of each of the Platform Core Services Suite 2087 features.

Figure 25:
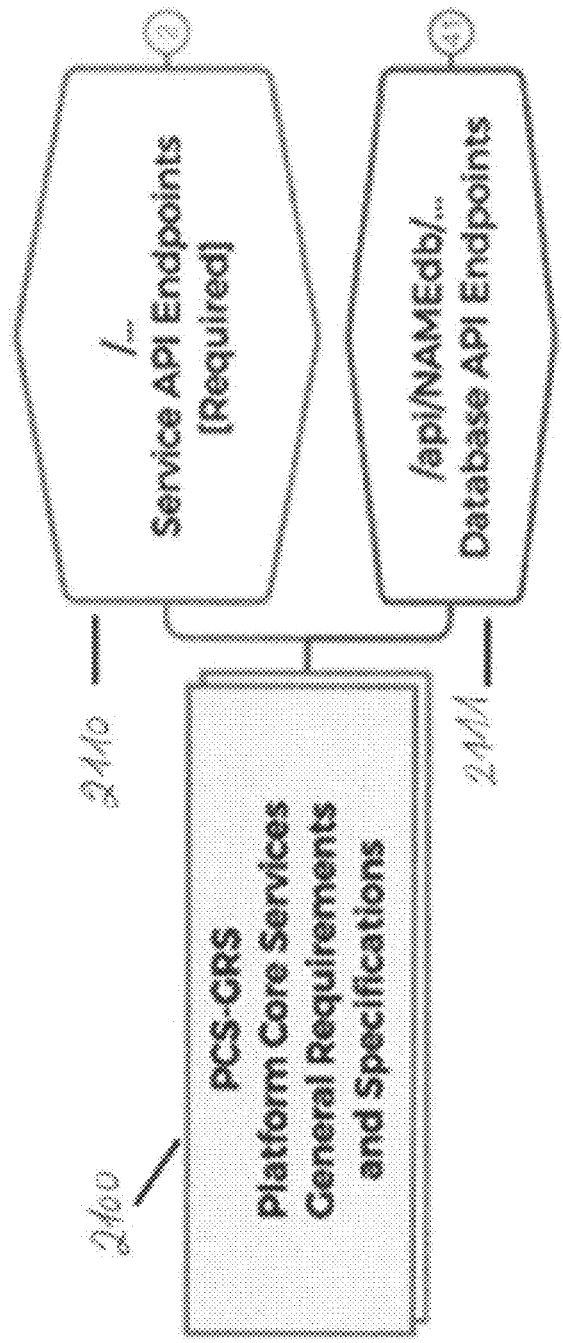
FIG. 25 is a block diagram illustrating a top-level PCS General Requirements and Specification block in accordance with one or more embodiments of the present disclosure.

FIG. 25 is a block diagram illustrating a top-level PCS General Requirements and Specification block in accordance with one or more embodiments of the present disclosure. The PCS General Requirements and Specifications (PCS-GRS) 2100 may define required and optional specifications for the implementations of various aspects of the PCS services. Among these specifications may be service-level and database API endpoints as shown in FIG. 25.

Figure 26:
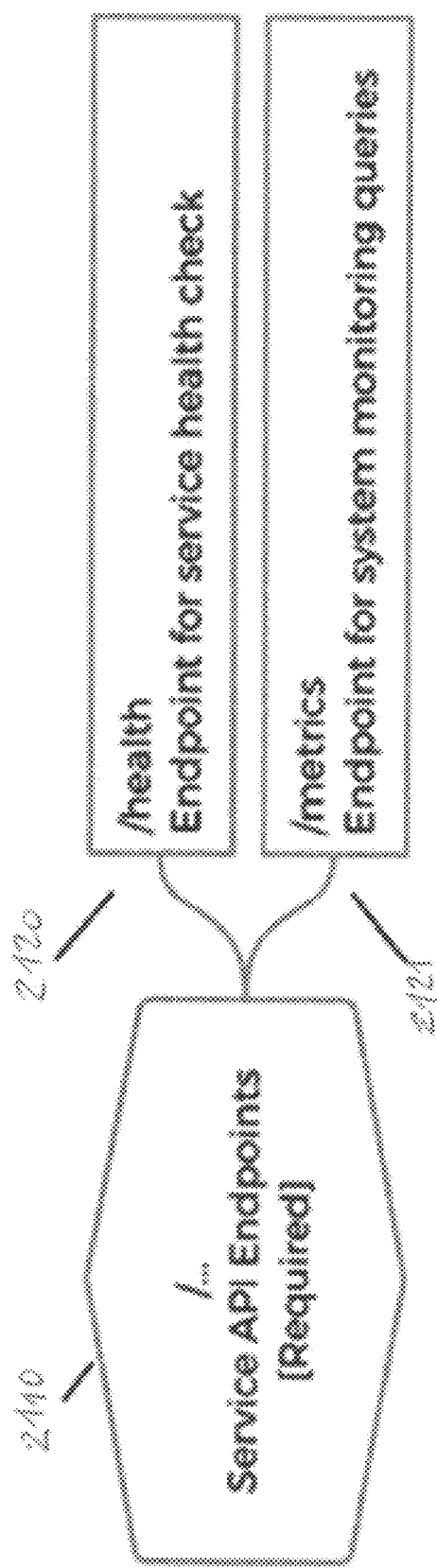
FIG. 26 is a block diagram illustrating PCS-GRS Service API Endpoints in accordance with one or more embodiments of the present disclosure.

FIG. 26 is a block diagram illustrating PCS-GRS Service API Endpoints in accordance with one or more embodiments of the present disclosure. The PCS Service API Endpoints 2110 may be HTTP endpoints that every service on the Platform is needed to implement. These endpoints may be currently specified as a REST API using the HTTP protocol. In other embodiments, the interface may be replicated under the gRPC protocol to provide an alternative communications method. This interface may be accessible on the Platform Backend Services 2003 network. These endpoints include but are not limited to the following.

In some embodiments, the/health Endpoint 2120 may implement a general service health check. When this endpoint is accessed, the service may respond with a "Status OK" message, if it is running. If the service has crashed, the requester may receive a network error. The /health endpoint is required by the platform Specification.

In some embodiments, the/metrics endpoint 2121 may implement a target for queries by a system monitoring application, such as Prometheus, for example. The Platform may use Prometheus for the acquisition and logging of system metrics. Prometheus may be included in the Platform Metrics Suite 2104 described later in this disclosure. The /metrics endpoint may provide any application metrics that are of value to system monitoring and/or maintenance. Each service may be implemented on the Platform may be required to provide at least, the following metrics:
 a. Total Requests Received: A counter of the total number of network request received by the service, implemented as a counter.
 b. Incoming Request Rate: A gauge measuring the rate of the incoming request.

Figure 27:
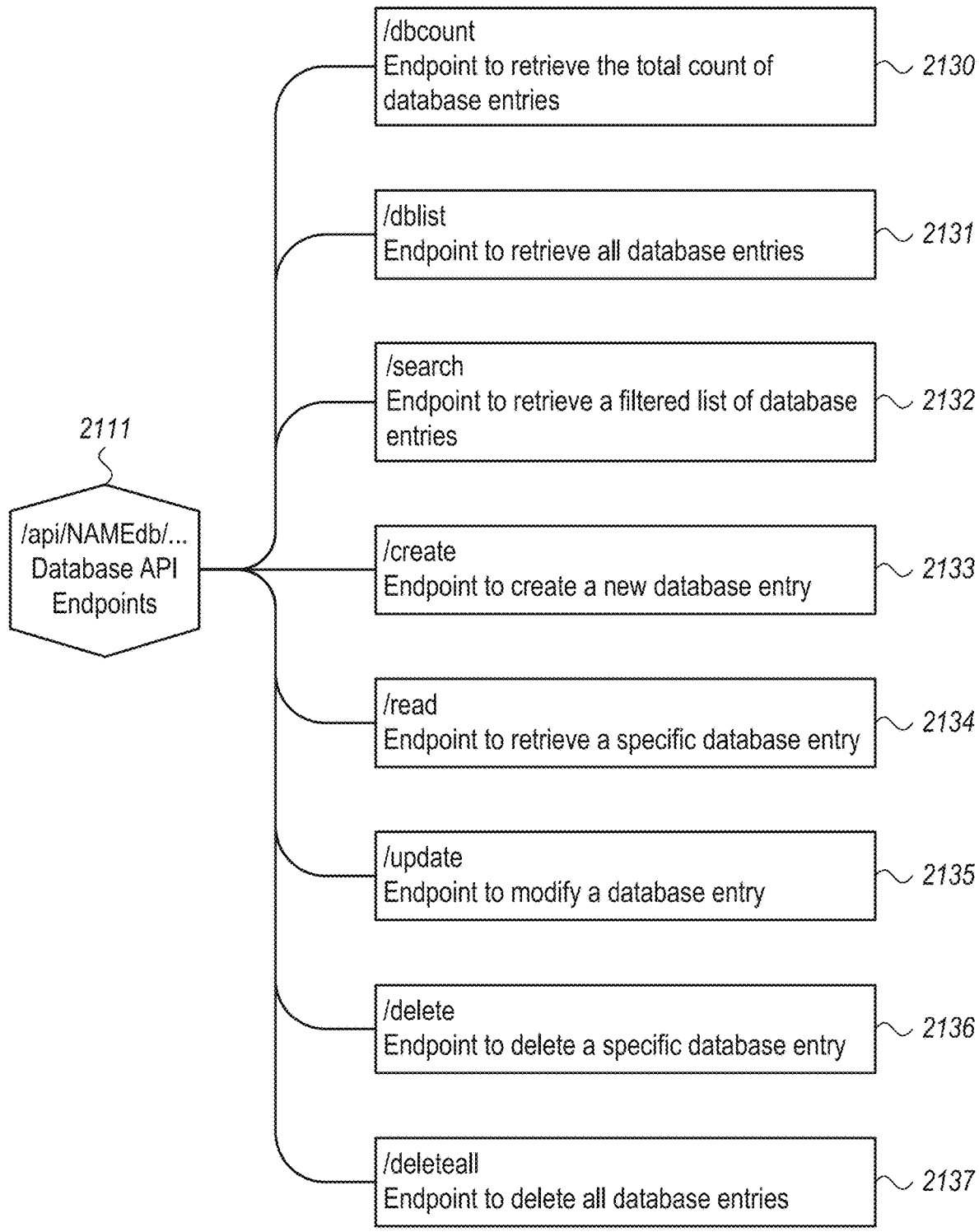
FIG. 27 is a block diagram illustrating MCP-GRS Database API endpoints in accordance with one or more embodiments of the present disclosure.

FIG. 27 is a block diagram illustrating MCP-GRS Database API endpoints in accordance with one or more embodiments of the present disclosure. The PCS Database API Endpoints 2111 may be HTTP endpoints that define a standard interface for direct interaction with a service database. The use of these endpoints may be optional but recommended. The PCS Database API Endpoints 2111 may be network communications endpoints that implement the basic CRUD (Create, Read, Update, Delete) operations on a service database. These endpoints may be currently specified as a REST API using the HTTP protocol.

In some embodiments, the interface may be replicated under the gRPC protocol to offer an alternative communications method. This interface may be accessible on the Platform Backend Services 2003 network and may be optional but recommended to support standardization among the platform applications.

In some embodiments, most of the Database API Endpoint(s) 2111 may expect to receive HTTP requests using the POST method. These requests may include a data payload in the HTTP request body which may have a defined format and may be referred to as the request data transfer object (DTO). The DTO may be described in the application source code. These endpoints are shown in FIG. 27.

The /dbcount Endpoint 2130: HTTP GET Returns the number of entries in the database.

The /dblist Endpoint 2131: HTTP GET Returns a listing of all entries in the database.

The /search Endpoint 2132: HTTP POST Returns a list of database entries, matching the search criteria specified in the received data transfer object.

The /create Endpoint 2133: HTTP POST Creates a new database entry using the received data transfer object.

The /read Endpoint 2134: HTTP POST Returns a single database entry, matching the search criteria specified in the received data transfer object.

The /update Endpoint 2135: HTTP POST Modifies the database entry specified in the search criteria in the received data transfer object.

The /delete Endpoint 2136: HTTP POST Deletes all database entries matching the search criteria specified in the received data transfer object. This endpoint requires a passcode.

The /deleteall Endpoint 2137: HTTP POST Deletes all of the entries in the database. This endpoint requires a passcode.

Figure 28:
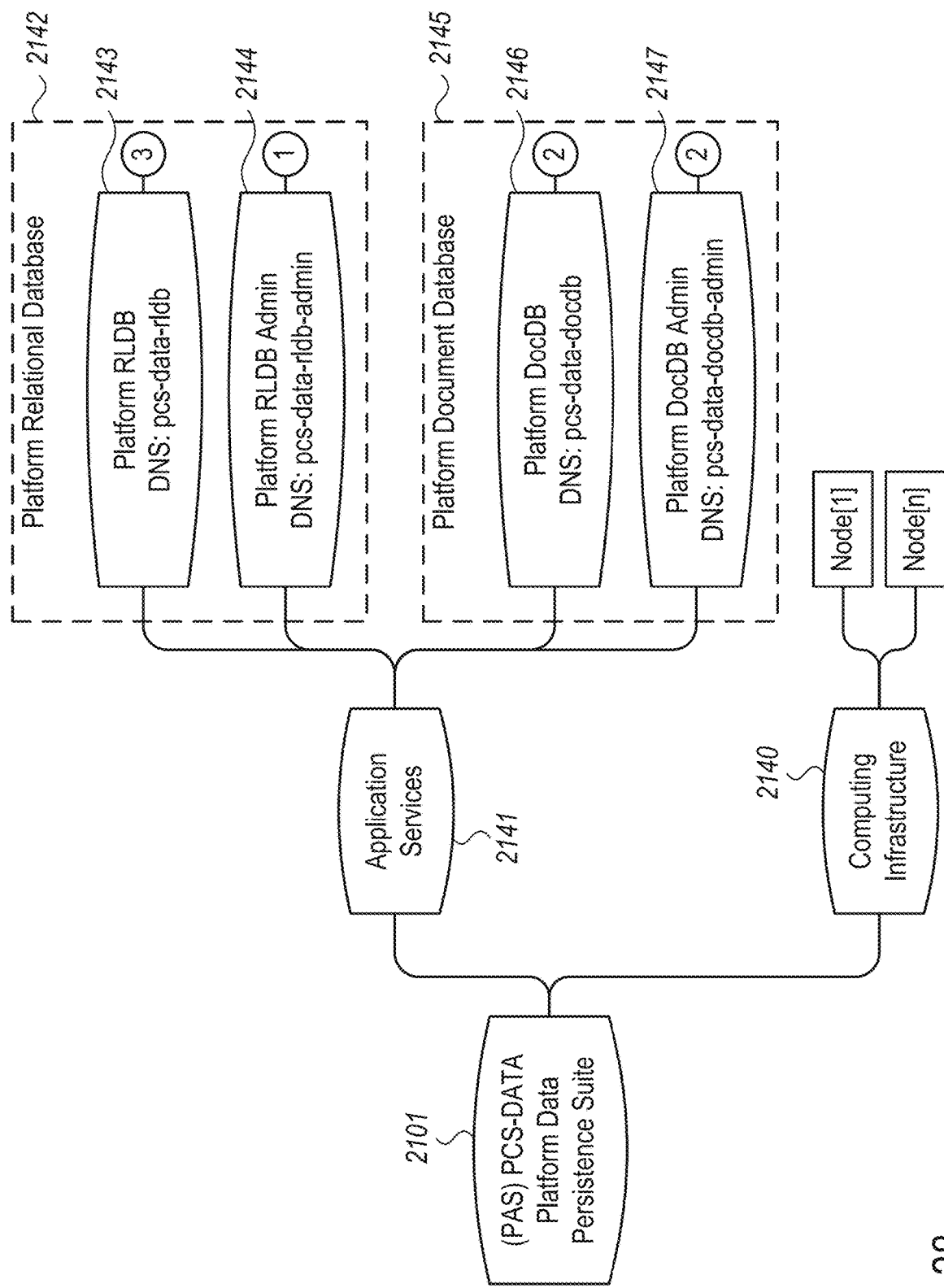
FIG. 28 is a block diagram illustrating a PCS Platform Data Persistence Suite in accordance with one or more embodiments of the present disclosure.

FIG. 28 is a block diagram illustrating a PCS Platform Data Persistence Suite in accordance with one or more embodiments of the present disclosure. Microservices may be generally ephemeral and may lack persistent storage for application data, yet most applications need to store data. The Platform Data Persistence Suite (PCS-DATA) 2101 is a feature of the Platform Core Services Suite 2087 that may meet this need by providing resources for data persistence (storage) as a series of platform services. These services may be accessible to any application running on the Platform Backend 2001. The PCS-DATA suite 2101 may be implemented as a resident part of a larger datacenter infrastructure, or on a standalone, Computing Infrastructure 2140 that may include of one or more computing nodes.

In some embodiments, The Platform Data Persistence Suite 2101 as shown in FIG. 28 may provide Application Services 2141 to support the storage of data. These services may include but are not limited to a Platform Relational Database 2142, and a Platform Document Database 2145.

In some embodiments, the Platform Relational Database 2142 may be implemented as an SQL database server denoted Platform RLDB 2143. The Platform RLDB may be implemented using an SQL based, relational database such as Postgres SQL or MySQL, for example. It may be accompanied by a web-based, administrative interface denoted Platform RLDB Admin 2144, which may provide maintenance and low-level manipulation of the database. The Platform RLDB may be accessible through REST API and gRPC interfaces and supports standard SQL queries.

In some embodiments, the Platform RLDB 2142 may be implemented as Postgres SQL that may be used to implement the database server, and Adminer may be used for the web administrative interface.

In some embodiments, the Platform Document Database 2145 may be implemented as a document database server denoted Platform DocDB 2146. The Platform DocDB may be implemented using a document database such as MongoDB, for example. It may be accompanied by a web based, administrative interface denoted "Platform DocDB Admin" 2147, which may provide maintenance and low-level manipulation of the database. The Platform DocDB may be accessible through REST API and gRPC interfaces.

In some embodiments, the Platform DocDB 2145 may be implemented with MongoDB that may be used to implement the database server, and Mongo-Express may be used for the web administrative interface.

Figure 29:
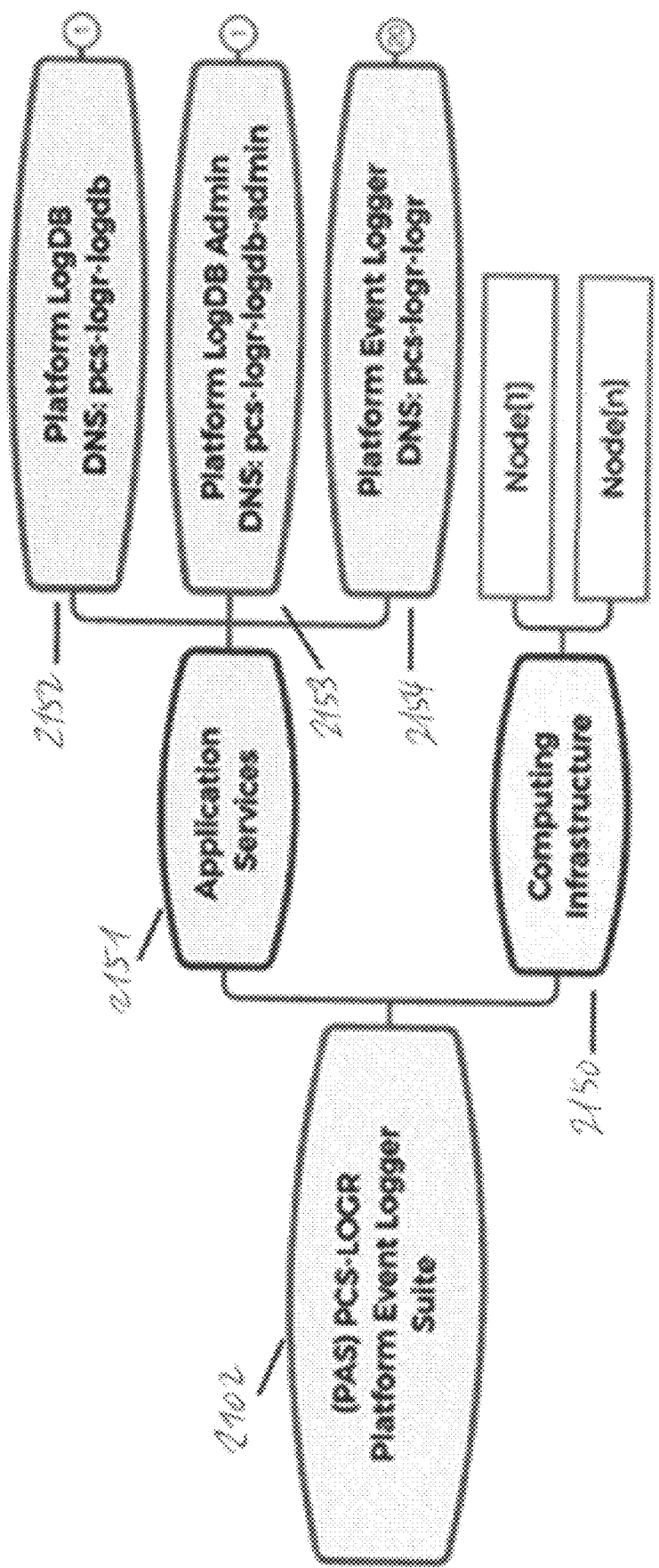
FIG. 29 is a block diagram illustrating a PCS Platform Event Logger Suite in accordance with one or more embodiments of the present disclosure.

FIG. 29 is a block diagram illustrating a PCS Platform Event Logger Suite in accordance with one or more embodiments of the present disclosure. The Platform Core Services 2087 may include a custom, time-series, event logging system, the Platform Event Logger Suite (PCS-LOGR) 2102. The PCS-LOGR 2102 may be used to record any event form any service and provides an alternative to the system metrics for recording application events. The Platform Event Logger Suite 2102 may be available to any application running on the platform. The PCS-LOGR 2102 may produce a text log that is easily human readable and may record the events to a relational database to enable event analytics and performance evaluation where desired.

In some embodiments, the Platform Event Logger Suite 2102 may be implemented as a resident part of a larger datacenter infrastructure, or on a standalone, "Computing Infrastructure" 2150 that may include one or more computing nodes.

In some embodiments, the Platform Logging Module 2102 may provide Application Services 2151 to support the logging of application events. These services may include but are not limited to the Logging Database, LogDB 2152, and the Platform Event Logger 2154.

In some embodiments, the logging database denoted as a Platform LogDB 2152 may be implemented as an SQL database server. In other embodiments, the Platform LogDB may be implemented using an SQL based, relational database, such as Postgres SQL or MySQL, for example. It may be accompanied by a web based, administrative interface denoted as a Platform LogDB Admin 2153, which may provide maintenance and low-level manipulation of the database. The Platform LogDB may be accessible through REST API and gRPC interfaces and may support standard SQL queries.

In some embodiments, the Platform LogDB 2152 may include Postgres SQL that may be used to implement the database server, and Adminer may be used for the web administrative interface.

Figure 30:
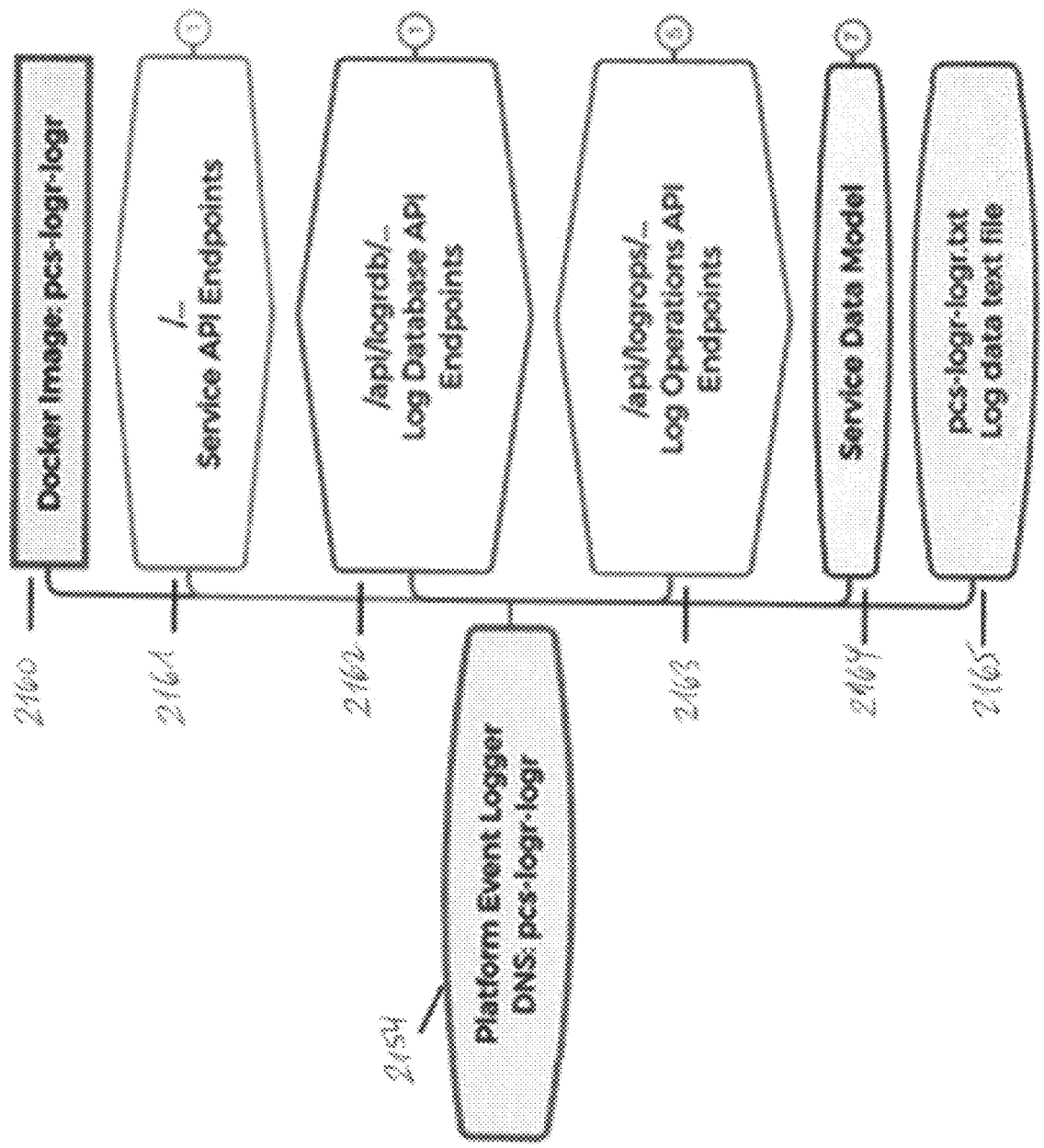
FIG. 30 is a block diagram illustrating a Platform Event Logger in accordance with one or more embodiments of the present disclosure.

FIG. 30 is a block diagram illustrating a Platform Event Logger in accordance with one or more embodiments of the present disclosure. A Platform Event Logger (PEL) 2154 may be the service interface to the event logging system that implements the API to be used to record events by other applications running on the platform. The PEL may be written in GO (Golang), a programming language developed by Google to utilize the resources and features of modern CPUs, non-transient computing memory, networks, and contemporary cloud-native infrastructure more effectively. The PEL may be a containerized microservice application created from a Docker image 2160.

In some embodiments, the Platform Event Logger 2154 may receive event record request from applications running on the platform on the internal network of the Platform Backend Services 2003 and may implement a REST API. The Platform Event Logger 2164 API commands may be divided into three functional groups: the Service API Endpoints Group 2161, the Log Database API Endpoints group 2162, and the Logging Operations API Endpoints group 2163.

In some embodiments, the Platform Event Logger Service API Endpoints 2161 may be HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

In some embodiments, the Platform Event Logger Service API Endpoints 2161 may conform to the PCS-GRS Service API Endpoint specification described hereinabove.

In some embodiments, the Platform Event Logger Log Database API Endpoints 2162 may include network communications endpoints that may implement the basic CRUD (Create, Read, Update, Delete) operations on the log database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Platform Event Logger Log Database API Endpoints 2162 may conform to the PCS-GRS Database API Endpoints specification described hereinabove.

Figure 31:
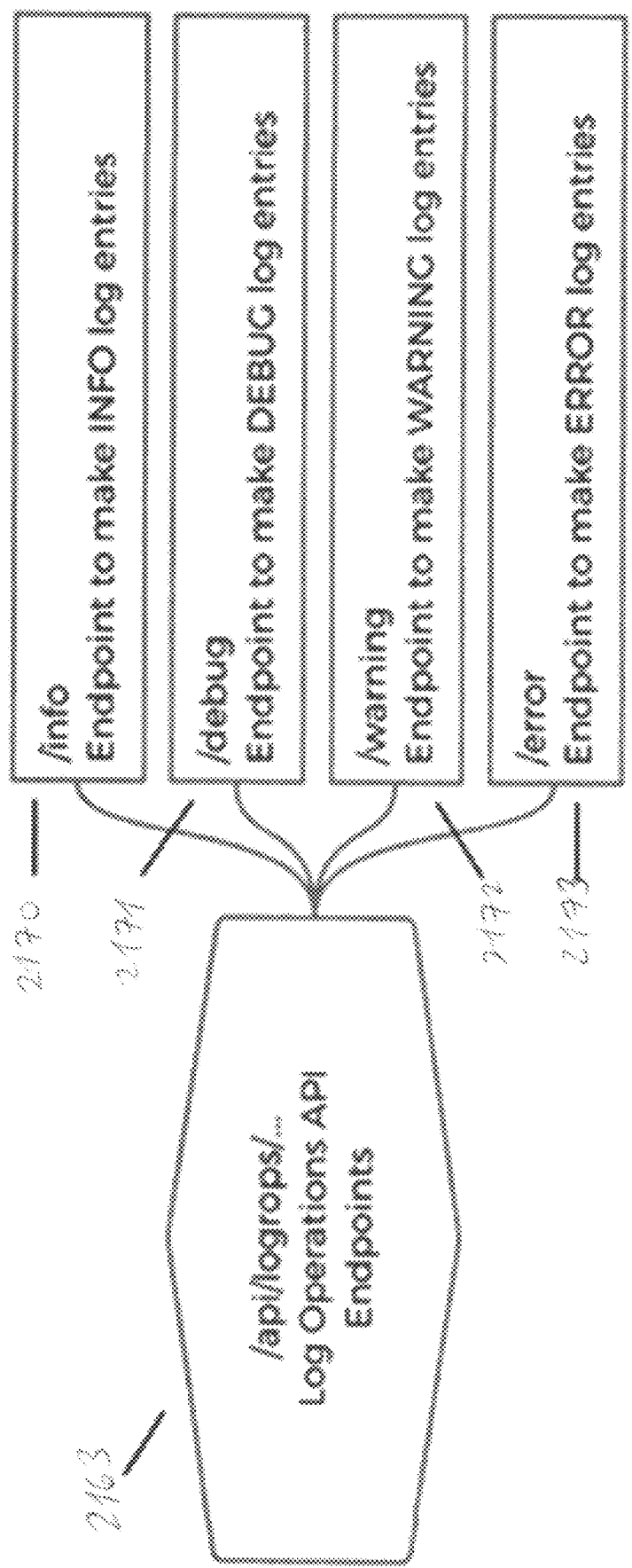
FIG. 31 is a block diagram illustrating operation endpoints of a Platform Event Logger in accordance with one or more embodiments of the present disclosure.

FIG. 31 is a block diagram illustrating operation endpoints of a Platform Event Logger in accordance with one or more embodiments of the present disclosure. The Platform Event Logger Log Operations API Endpoints 2163 may include network communications endpoints that may implement the API for the event logging feature. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Event Logger Operations API Endpoint(s) 2163 may receive HTTP requests using the POST method. These requests may include a data payload in the HTTP request body which has a defined structure and may be referred to as the request data transfer object (DTO). The DTO is described in the application's source code.

In some embodiments, each of the Logging Operations API Endpoints may include:

The /info Endpoint 2170: HTTP POST may create a database entry labeled "INFO". These entries may store informative messages, that may indicate that such an event has occurred and providing information about the event.

The /debug Endpoint 2171: HTTP POST may create a database entry labeled "DEBUG". These entries may store event messages that may be useful for application or system troubleshooting.

The /warning Endpoint 2172: HTTP POST may create a database entry labeled "WARNING". These entries store event messages that may be useful for application or system troubleshooting.

The /error Endpoint 2173: HTTP POST may create a database entry labeled "ERROR". These entries store event messages when an application error occurs. The message may include information regarding the error.

Figure 32:
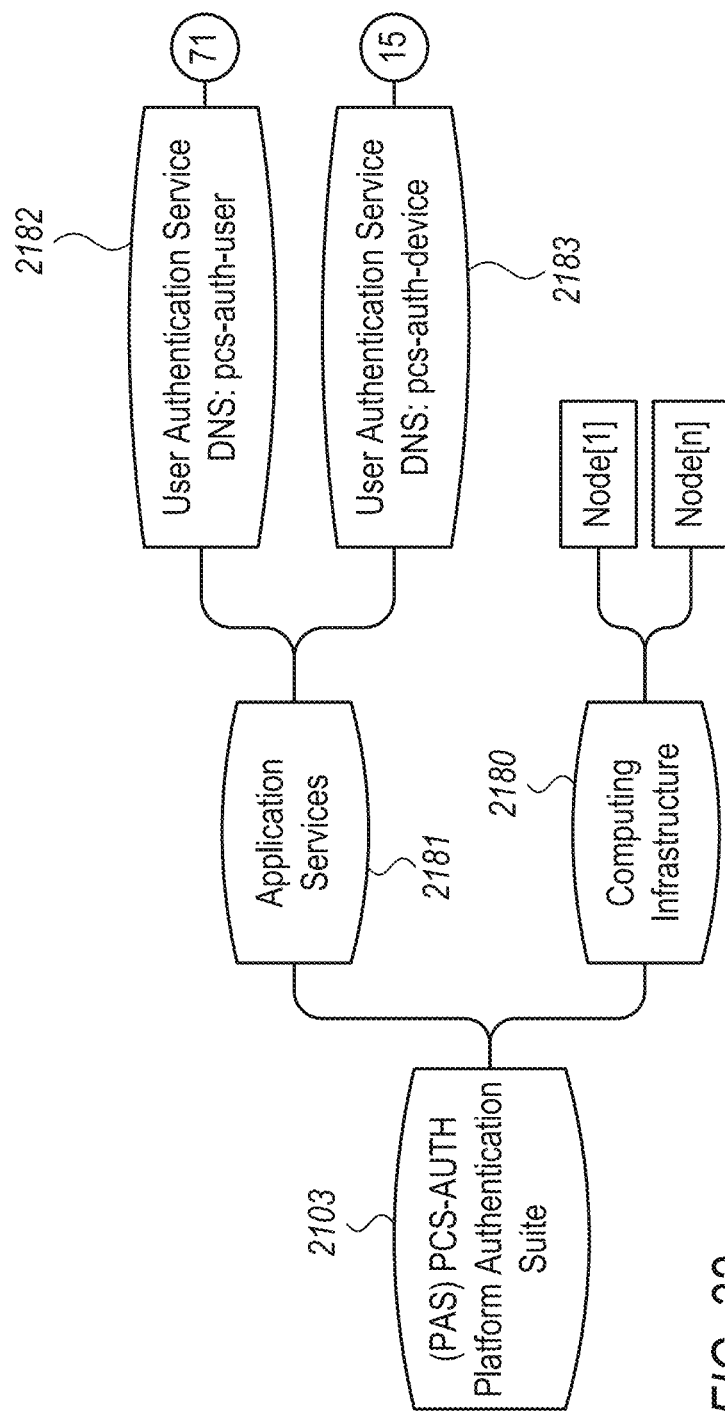
FIG. 32 is a block diagram illustrating a PCS Platform Authentication Suite in accordance with one or more embodiments of the present disclosure.

FIG. 32 is a block diagram illustrating a PCS Platform Authentication Suite in accordance with one or more embodiments of the present disclosure. The Platform Core Services Suite 2087 may include the Platform Authentication Suite (PCS-AUTH) 2103. The PCS-AUTH 2103 may store profiles of users and devices that may be used to authenticate request for access to the platform. The user and device profiles stored in the PCS-AUTH 2103 may also implement access controls that may restrict the profile's access to specific platform applications and features.

In some embodiments, the PCS-AUTH 2103 may be implemented as a resident part of a larger datacenter infrastructure, or on a standalone, "Computing Infrastructure" 2180 that may include one or more computing nodes.

In some embodiments, the PCS-AUTH 2103 may include two Application Services 2181. The User Authentication Service 2182 may be used to authenticate users attempting to access the platform, and the Device Authentication Service 2183 may be used for device authentication. Each authentication service may implement a database for storage of its respective profile information. These databases may be stored in the PCS Platform Data Persistence Suite 2101 in the Platform Document Database 2145.

Figure 33:
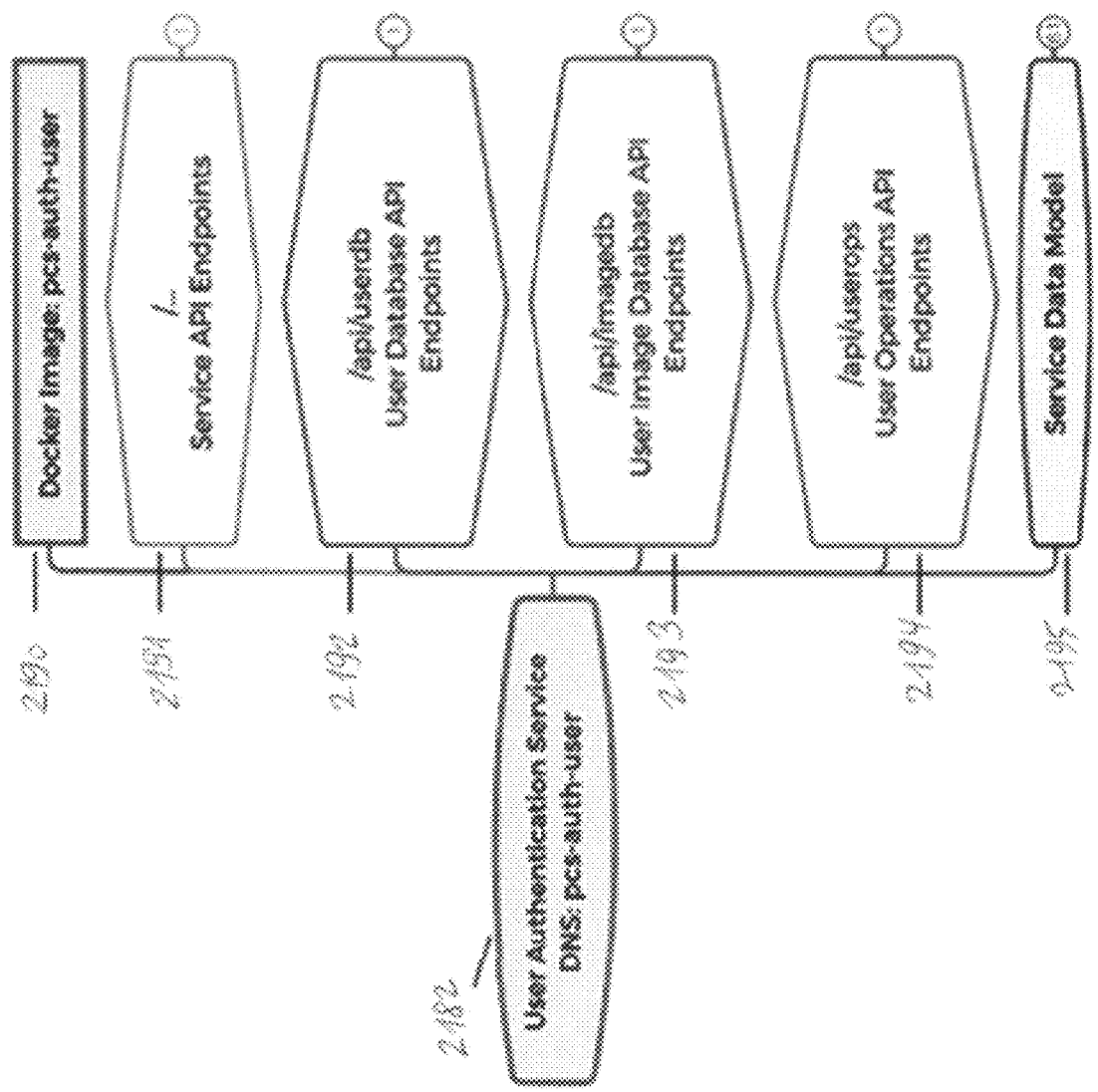
FIG. 33 is a block diagram illustrating a PCS-AUTH User Authentication Service in accordance with one or more embodiments of the present disclosure.

FIG. 33 is a block diagram illustrating a PCS-AUTH User Authentication Service in accordance with one or more embodiments of the present disclosure. The User Authentication Service (UAS) 2182 may implement the API to be used to interact with the user profiles database and to perform user operations. The UAS 2182 may be written in GO (Golang), a programming language developed by Google to utilize the resources and features of modern CPUs, non-transient computing memory, networks, and contemporary cloud-native infrastructure more effectively. The UAS 2182 may be a containerized microservice application created from a Docker image 2190.

In some embodiments, the User Authentication Service 2182 may receive a request from applications running on the platform on the internal network of the Platform Backend Services 2003 and may implement a REST API. The UAS 2182 API commands may be divided into four functional groups: The Service API Endpoints Group 2191, the User Database API Endpoints group 2192, the User Image Database API Endpoints group 2193, and the User Operations API Endpoints group 2194.

In some embodiments, the User Authentication Service API Endpoints 2191 may include HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

The User Authentication Service API Endpoints 2191 may conform to the PCS-GRS Service API Endpoint specification described hereinabove.

In some embodiments, the User Authentication Service User Database API Endpoints 2192 may include network communications endpoints that may implement the basic CRUD (Create, Read, Update, Delete) operations on the log database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the User Authentication Service User Database API Endpoints 2192 may conform to the PCS-GRS Database API Endpoints specification described hereinabove.

In some embodiments, the User Authentication Service User Image Database API Endpoints 2193 may include network communications endpoints that may implement the basic CRUD (Create, Read, Update, Delete) operations on the log database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the User Authentication Service User Image Database API Endpoints 2193 may conform to the PCS-GRS Database API Endpoints specification described hereinabove.

In some embodiments, the User Authentication Service User Operations API Endpoints 2194 may include network communications endpoints that may implement the API for the user operations features. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the User Operations API Endpoint(s) 2194 may receive HTTP requests using the POST method. These requests may include a data payload in the HTTP request body which may have a defined structure and may be referred to as the request data transfer object (DTO). The DTO may be described in the application's source code.

Figure 34:
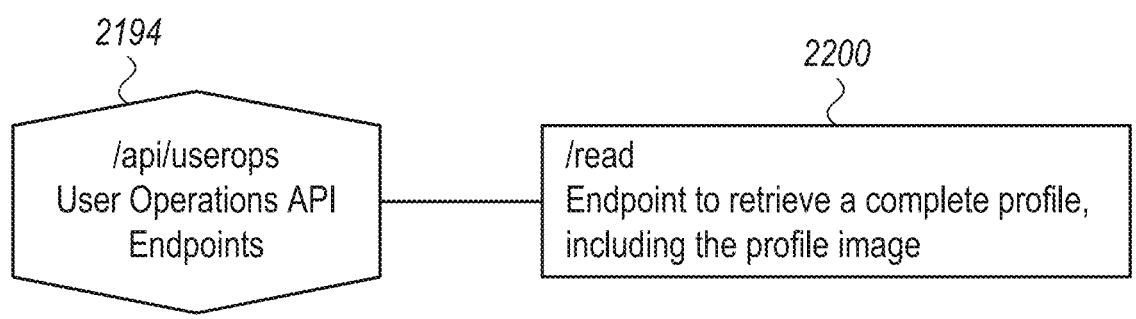
FIG. 34 is a block diagram illustrating User Operation API Endpoints in a User Authentication Service in accordance with one or more embodiments of the present disclosure.

FIG. 34 is a block diagram illustrating User Operation API Endpoints 2194 in a User Authentication Service in accordance with one or more embodiments of the present disclosure. A /read Endpoint 2200: HTTP POST may be used to retrieve a complete user profile that may include the user profile image.

Figure 35:
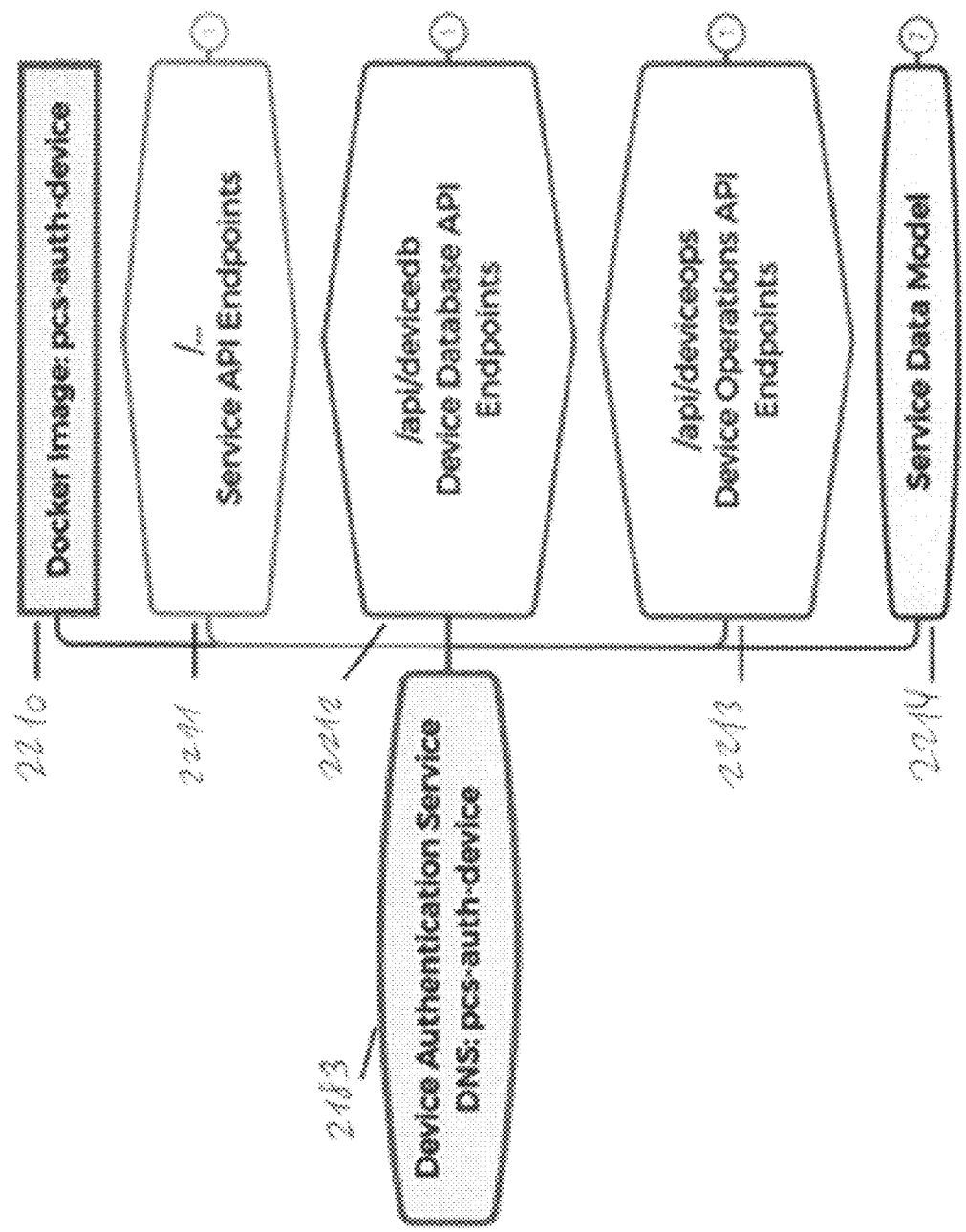
FIG. 35 is a block diagram illustrating an MCP-PAM Device Authentication Service in accordance with one or more embodiments of the present disclosure.

FIG. 35 is a block diagram illustrating an MCP-PAM Device Authentication Service in accordance with one or more embodiments of the present disclosure. The "Device Authentication Service" 2183 (DAS) implements the API to be used to interact with the device profiles database and to perform device authentication operations. The DAS 2183 is written in GO (Golang), a programming language developed by Google to utilize the resources and features of modern CPUs, non-transient computing memory, networks, and contemporary cloud-native infrastructure more effectively. The DAS 2183 is a containerized microservice application created from a Docker image 2210.

The Device Authentication Service 2183 may receive a request from applications running on the platform on the internal network of the Platform Backend Services 2003 and may implement a REST API. The DAS 2183 API commands may be divided into three functional groups: the Service API Endpoints Group 2211, the Device Database API Endpoints group 2212, and the Device Operations API Endpoints group 2213.

In some embodiments, the Device Authentication Service API Endpoints 2211 may include HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

In some embodiments, the Device Authentication Service API Endpoints 2211 may conform to the PCS-GRS Service API Endpoint specification described hereinabove.

In some embodiments, the Device Authentication Service Device Database API Endpoints 2212 may include network communications endpoints that implement the basic CRUD (Create, Read, Update, Delete) operations on the device database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Device Authentication Service Device Database API Endpoints 2212 may conform to the PCS-GRS Database API Endpoints specification described hereinabove.

In some embodiments, the Device Authentication Service Device Operations API Endpoints 2213 may include network communications endpoints that may implement the API for the device operations features. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Device Operations API Endpoint(s) 2213 may receive HTTP requests using the POST method. These requests may include a data payload in the HTTP request body which may have a defined structure and may be referred to as the request data transfer object (DTO). The DTO may be described in the application's source code.

Figure 36:
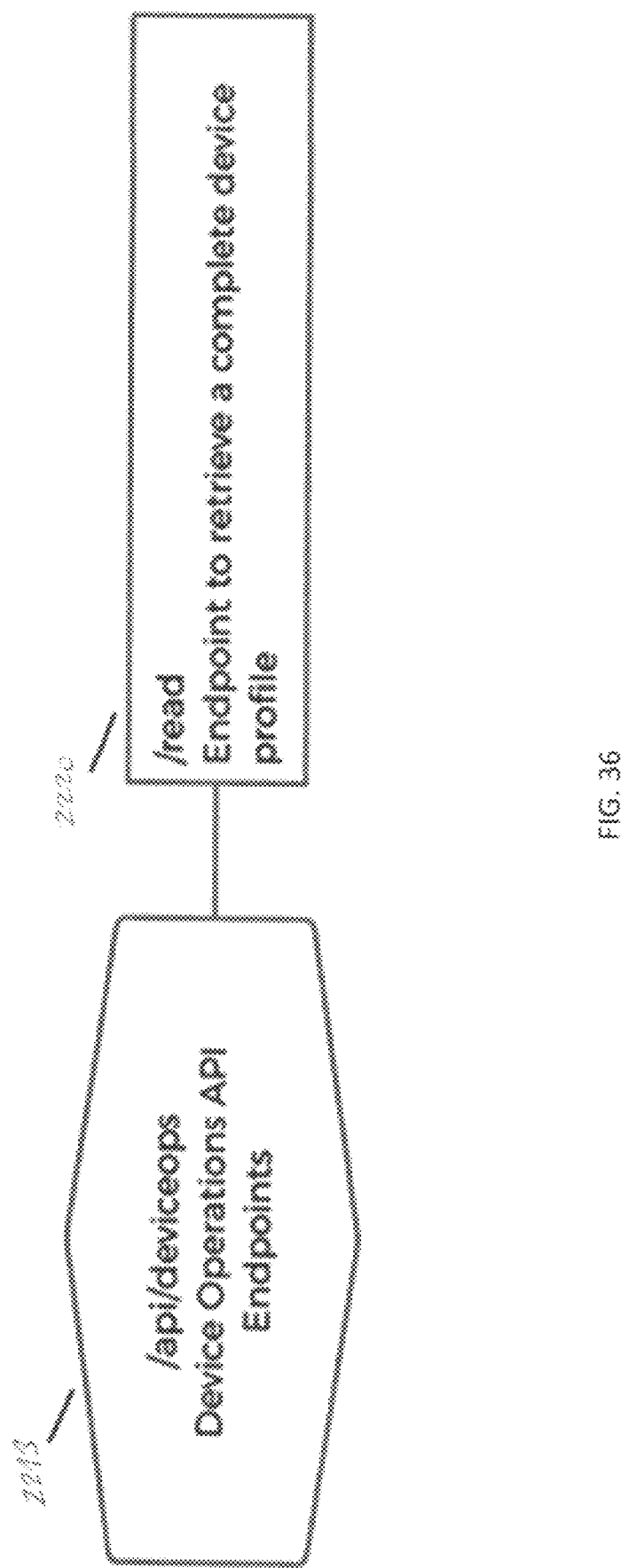
FIG. 36 is a block diagram illustrating Device Operation API Endpoints in a Device Authentication Service in accordance with one or more embodiments of the present disclosure.

FIG. 36 is a block diagram illustrating Device Operation API Endpoints 2213 in a Device Authentication Service in accordance with one or more embodiments of the present disclosure. The /read Endpoint 2220: HTTP POST may be used to retrieve a complete device profile.

Figure 37:
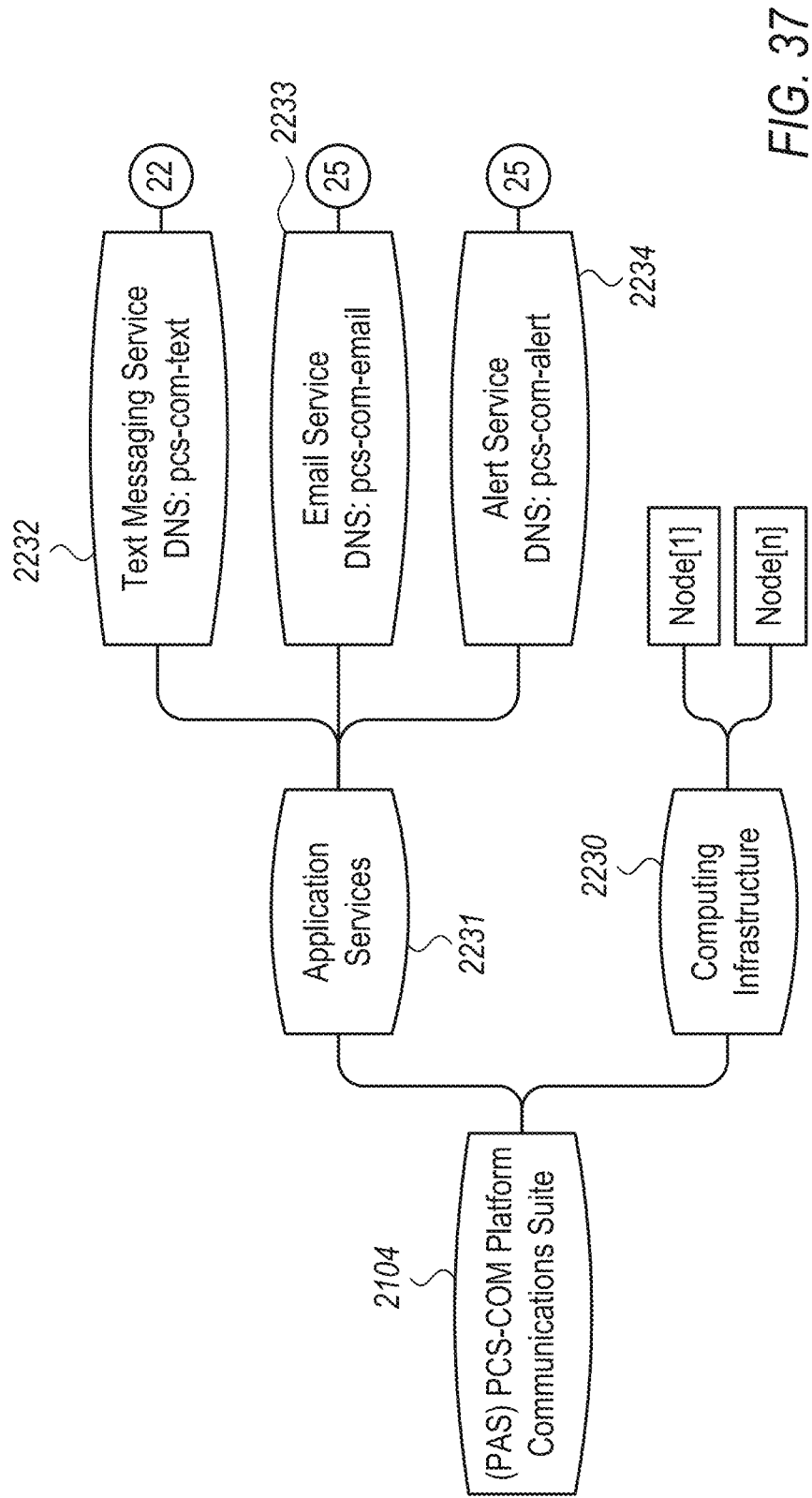
FIG. 37 is a block diagram illustrating a PCS Platform Communication Suite in accordance with one or more embodiments of the present disclosure.

FIG. 37 is a block diagram illustrating a PCS Platform Communication Suite in accordance with one or more embodiments of the present disclosure. The Platform Core Services Suite 2087 may include the Platform Communications Suite (PCS-COM) 2104. The PCS-COM 2104 may serve as the general communications service for the platform. Any application running on the platform may utilize the PCS-COM 2104 to send text, email or alert notifications.

In some embodiments, the PCS-COM 2104 may be implemented as a resident part of a larger datacenter infrastructure, or on a standalone Computing Infrastructure 2230 that may include one or more computing nodes.

In some embodiments, the PCS-COM 2104 may include three Application Services 2231. The Text Messaging Service 2232 may be used to send text message notifications to users, the Email Service 2233 may be used to send email notifications to users, and the Alert Service 2234 may be used to send alert notifications to client applications. Each service may implement a database for storage of its sent messages. These databases may be stored in the PCS Platform Data Persistence Suite 2101 in the Platform Document Database 2145.

Figure 38:
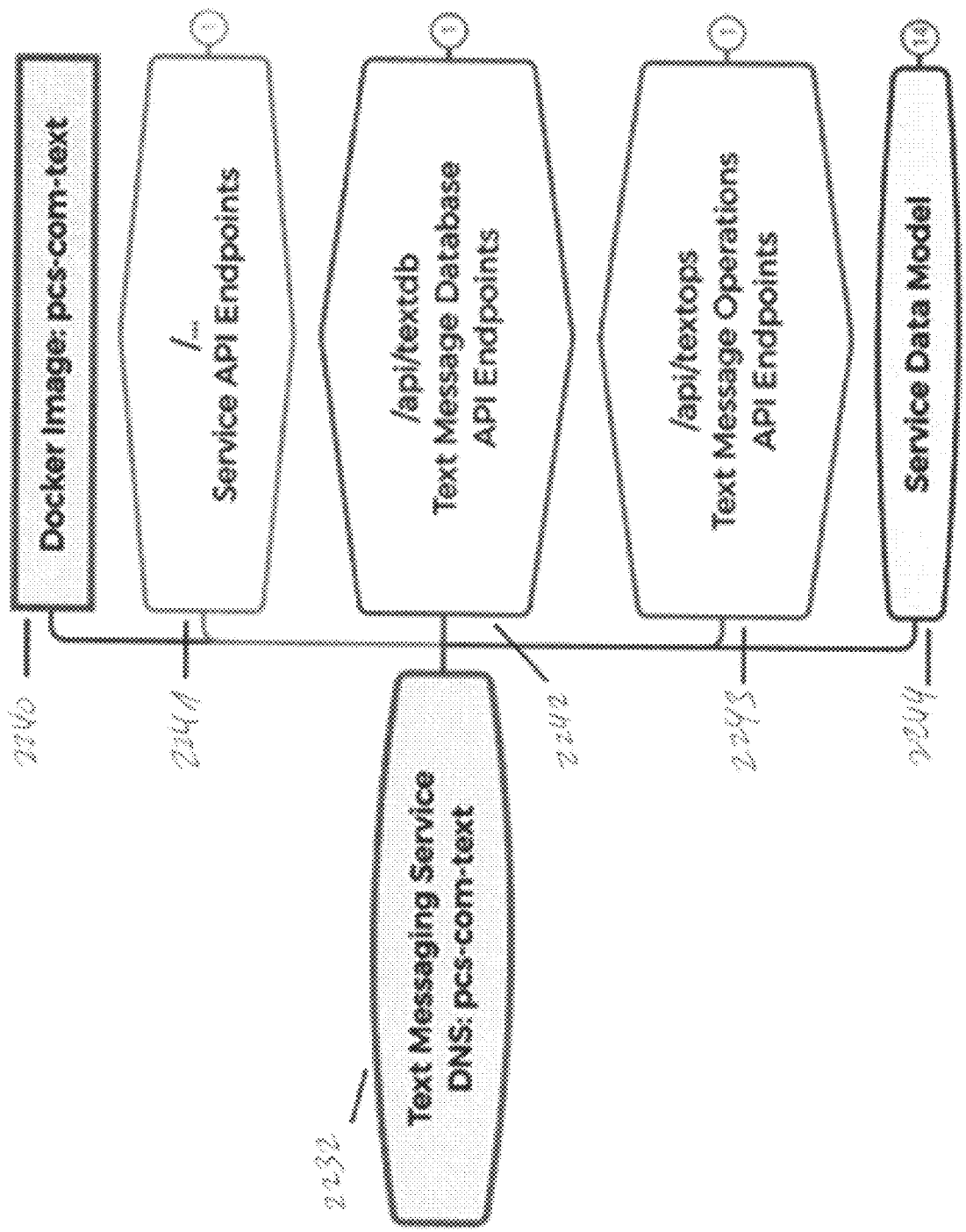
FIG. 38 is a block diagram illustrating a PCS-COM Text Messaging Service in accordance with one or more embodiments of the present disclosure.

FIG. 38 is a block diagram illustrating a PCS-COM Text Messaging Service in accordance with one or more embodiments of the present disclosure. The Text Messaging Service (TMS) 2232 may implement the API to be used to interact with the text message database and to perform text messaging operations. The TMS 2232 may be written in GO (Golang), a programming language developed by Google to utilize the resources and features of modern CPUs, non-transient computing memory, networks, and contemporary cloud-native infrastructure more effectively. The TMS 2232 may be a containerized microservice application created from a Docker image 2240.

In some embodiments, the Text Messaging Service 2232 may receive a request from applications running on the platform on the internal network of the Platform Backend Services 2003 and may implement a REST API. The TMS 2232 API commands may be divided into three functional groups: the Service API Endpoints Group 2241, the Text Message Database API Endpoints group 2242, and the Text Message Operations API Endpoints group 2243.

In some embodiments, the Text Message Service API Endpoints 2241 may include HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

In some embodiments, the Text Message Service API Endpoints 2241 may conform to the PCS-GRS Service API Endpoint specification described hereinabove.

In some embodiments, the Text Message Service Text Message Database API Endpoints 2242 may include network communications endpoints that may implement the basic CRUD (Create, Read, Update, Delete) operations on the text message database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Text Message Service Text Message Database API Endpoints 2242 may conform to the PCS-GRS Database API Endpoints specification described hereinabove.

In some embodiments, the Text Message Service Text Message Operations API Endpoints 2243 may include network communications endpoints that may implement the API for the text message operations. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Text Message Operations API Endpoint(s) 2243 may receive HTTP requests using the POST method. These requests may include a data payload in the HTTP request body which may have a defined structure and may be referred to as the request data transfer object (DTO). The DTO may be described in the application's source code.

Figure 39:
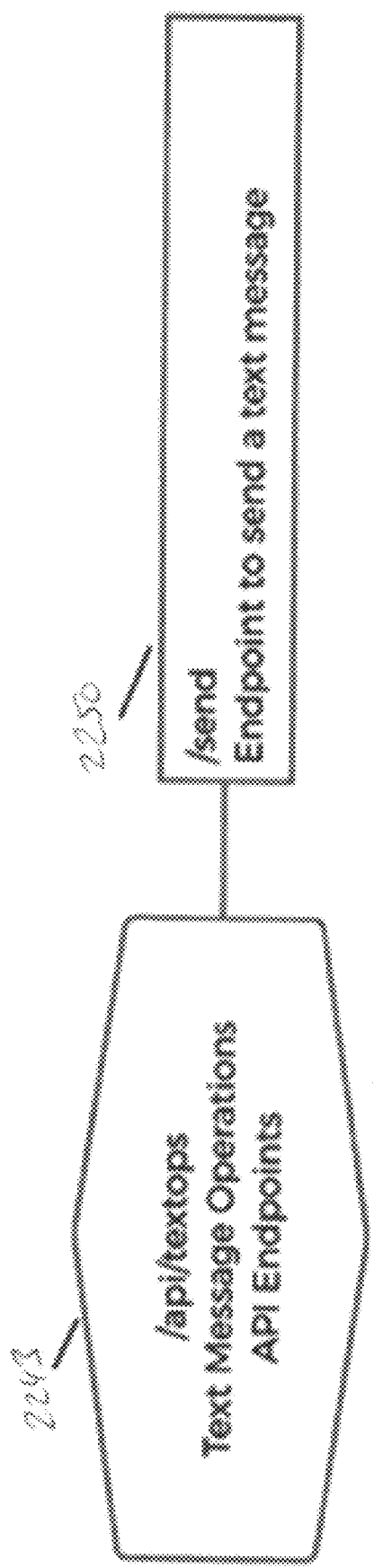
FIG. 39 is a block diagram illustrating Text Message Operations API Endpoints in a Text Messaging Service in accordance with one or more embodiments of the present disclosure.

FIG. 39 is a block diagram illustrating Text Message Operations API Endpoints 2243 in a Text Messaging Service in accordance with one or more embodiments of the present disclosure. The /read Endpoint 2250: HTTP POST may be used to retrieve a text message.

Figure 40:
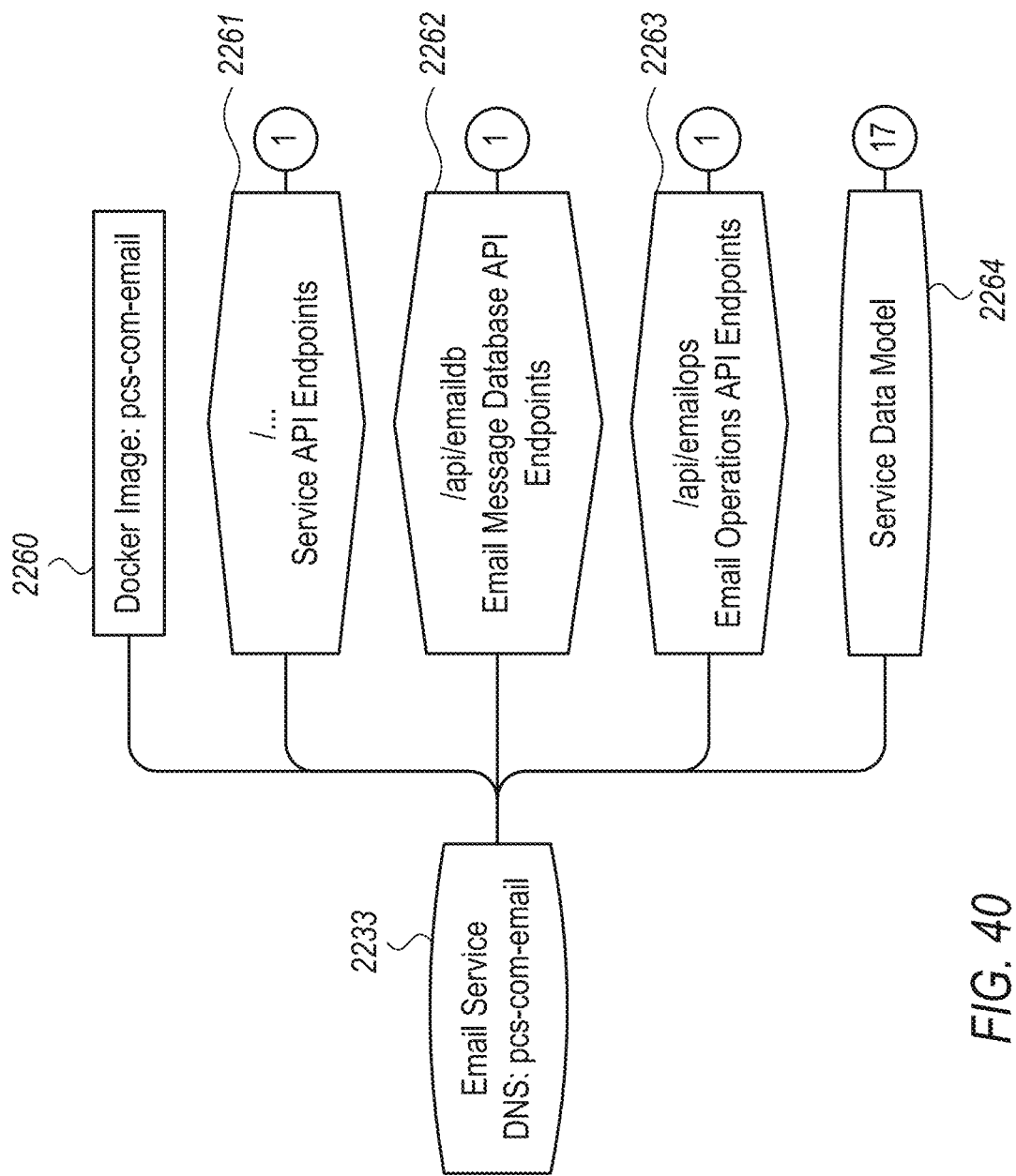
FIG. 40 is a block diagram illustrating an MCP-PMSG Email Service in accordance with one or more embodiments of the present disclosure.

FIG. 40 is a block diagram illustrating an MCP-PMSG Email Service in accordance with one or more embodiments of the present disclosure. The Email Service 2233 may implement the API to be used to interact with the email message database and to perform email messaging operations. The Email Service 2233 may be written in GO (Golang), a programming language developed by Google to utilize the resources and features of modern CPUs, non-transient computing memory, networks, and contemporary cloud-native infrastructure more effectively. The Email Service 2233 may be a containerized microservice application created from a Docker image 2260.

In some embodiments, the Email Service 2233 may receive a request from applications running on the platform on the internal network of the Platform Backend Services 2003 and implements a REST API. The Email Service 2233 API commands may be divided into three functional groups: the Service API Endpoints Group 2261, the Email Message Database API Endpoints group 2262, and the Email Operations API Endpoints group 2263. Refer to FIG. 25, below.

In some embodiments, the Email Service API Endpoints 2261 may include HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

In some embodiments, the Email Service API Endpoints 2261 may conform to the PCS-GRS Service API Endpoint specification described hereinabove.

In some embodiments, the Email Service Email Message Database API Endpoints 2262 may include network communications endpoints that may implement the basic CRUD (Create, Read, Update, Delete) operations on the email message database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Email Service Email Message Database API Endpoints 2262 may conform to the PCS-GRS Database API Endpoints specification described hereinabove.

In some embodiments, the Email Service Email Operations API Endpoints 2263 may include network communications endpoints that may implement the API for the email message operations. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Email Operations API Endpoint(s) 2263 may receive HTTP requests using the POST method. These requests may include a data payload in the HTTP request body which may have a defined structure and may be referred to as the request data transfer object (DTO). The DTO may be described in the application's source code.

Figure 41:
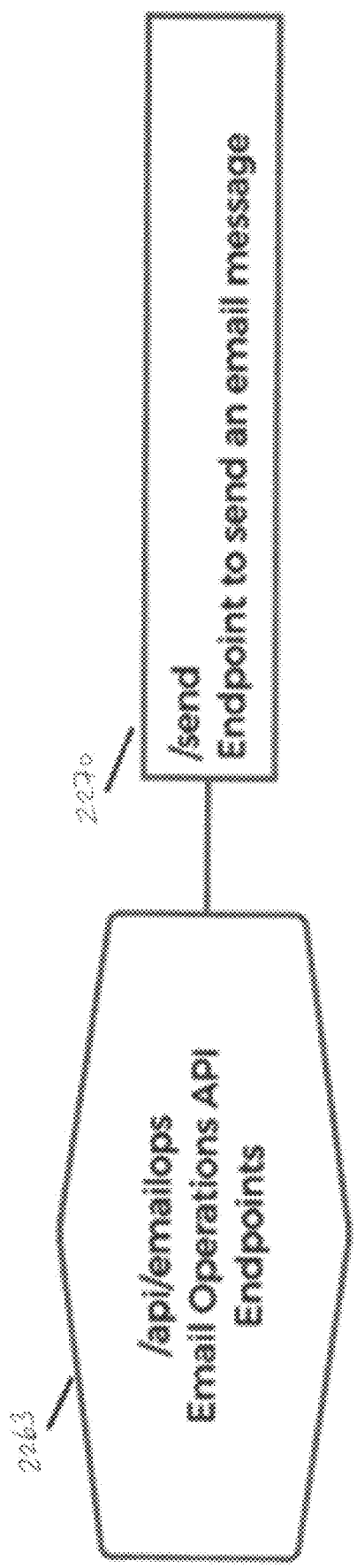
FIG. 41 is a block diagram illustrating Email Message Operation API Endpoints in an Email Message Service in accordance with one or more embodiments of the present disclosure.

FIG. 41 is a block diagram illustrating Email Message Operation API Endpoints 2263 in an Email Message Service in accordance with one or more embodiments of the present disclosure. The /read Endpoint 2270: HTTP POST may be used to retrieve an email message.

Figure 42:
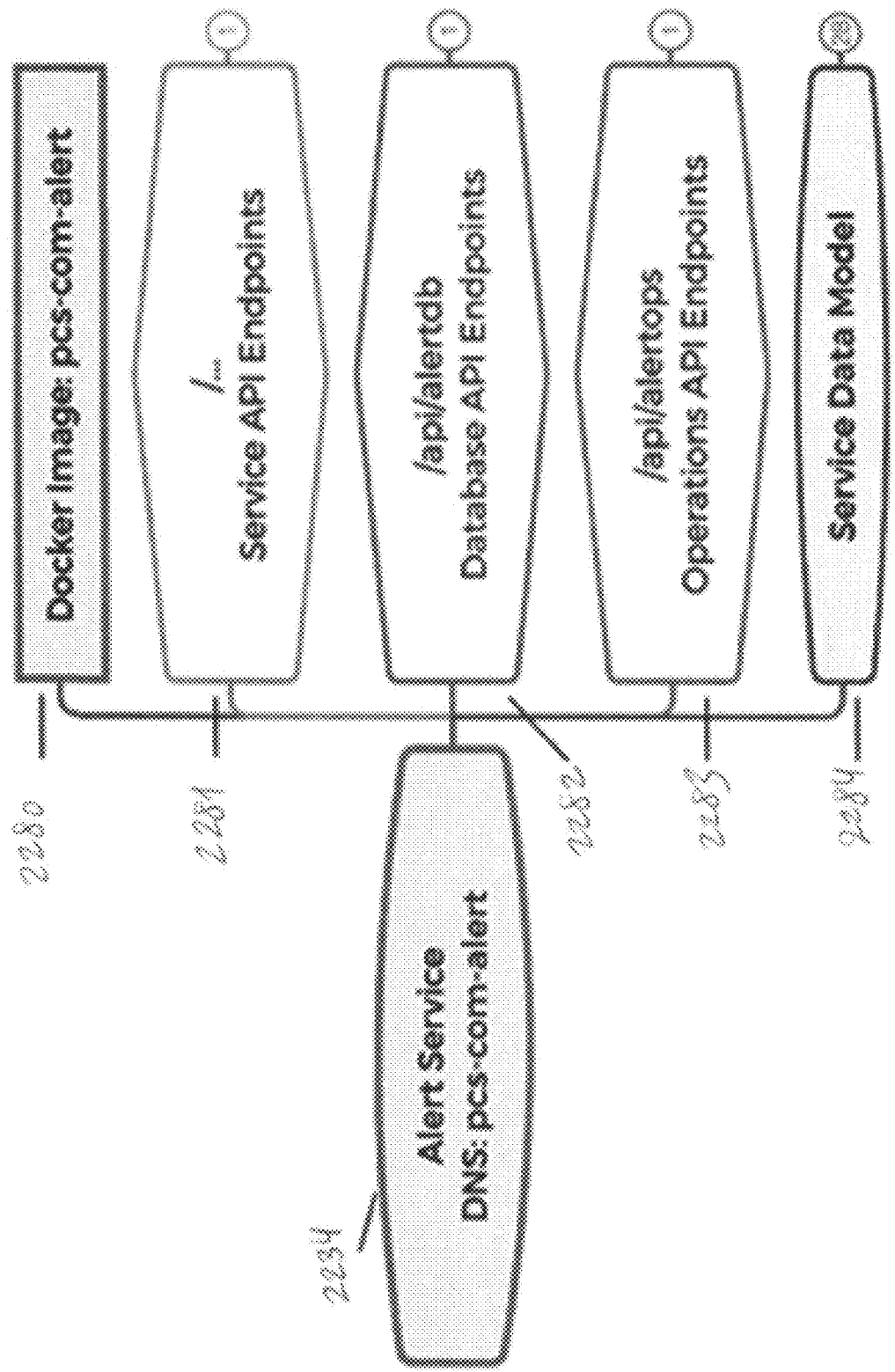
FIG. 42 is a block diagram illustrating a PCS-COM Alert Service in accordance with one or more embodiments of the present disclosure.

FIG. 42 is a block diagram illustrating a PCS-COM Alert Service in accordance with one or more embodiments of the present disclosure. The "Alert Service" 2234 may implement the API to be used to interact with the alert message database and to perform alert messaging operations. The Alert Service 2234 may be written in GO (Golang), a programming language developed by Google to utilize the resources and features of modern CPUs, non-transient computing memory, networks, and contemporary cloud-native infrastructure more effectively. The Alert Service 2234 may be a containerized microservice application created from a Docker image 2280.

In some embodiments, the Alert Service 2234 may receive a request from applications running on the platform on the internal network of the Platform Backend Services 2003 and may implement a REST API. The Alert Service 2234 API commands may be divided into three functional groups: the Service API Endpoints Group 2281, the Alert Message Database API Endpoints group 2282, and the Alert Operations API Endpoints group 2283.

In some embodiments, the Alert Service API Endpoints 2281 may include HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

In some embodiments, the Alert Service API Endpoints 2281 may conform to the PCS-GRS Service API Endpoint specification described hereinabove.

In some embodiments, the Alert Service Alert Message Database API Endpoints 2282 may include network communications endpoints that implement the basic CRUD (Create, Read, Update, Delete) operations on the email message database. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Alert Service Alert Message Database API Endpoints 2262 may conform to the PCS-GRS Database API Endpoints specification described hereinabove.

In some embodiments, the Alert Service Alert Operations API Endpoints 2283 may include network communications endpoints that implement the API for the alert message operations. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, the Alert Operations API Endpoint(s) 2283 may receive HTTP requests using the POST method. These requests may include a data payload in the HTTP request body which may have a defined structure and may be referred to as the request data transfer object (DTO). The DTO may be described in the application's source code.

Figure 43:
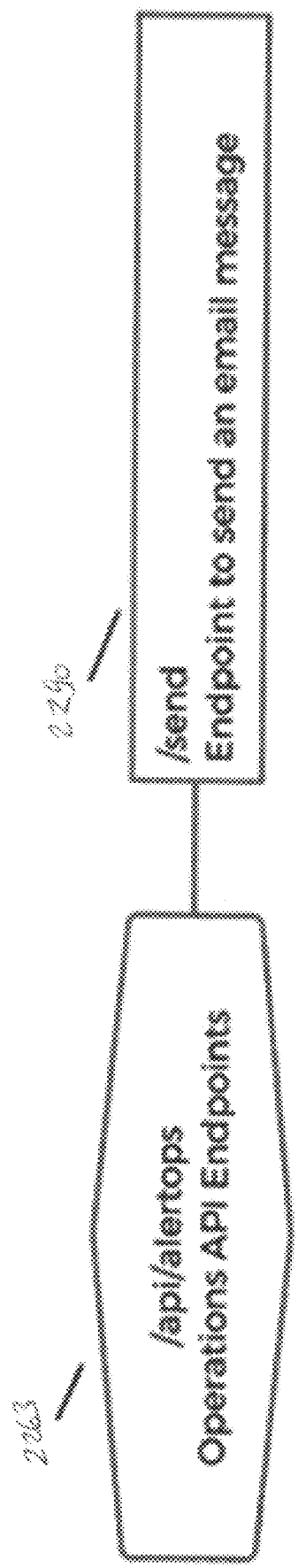
FIG. 43 is a block diagram illustrating Alert Operations API Endpoints in an Alert Service in accordance with one or more embodiments of the present disclosure.

FIG. 43 is a block diagram illustrating Alert Operations API Endpoints 2263 in an Alert Service in accordance with one or more embodiments of the present disclosure. The /read Endpoint 2290: HTTP POST may be used to retrieve an email message.

Figure 44:
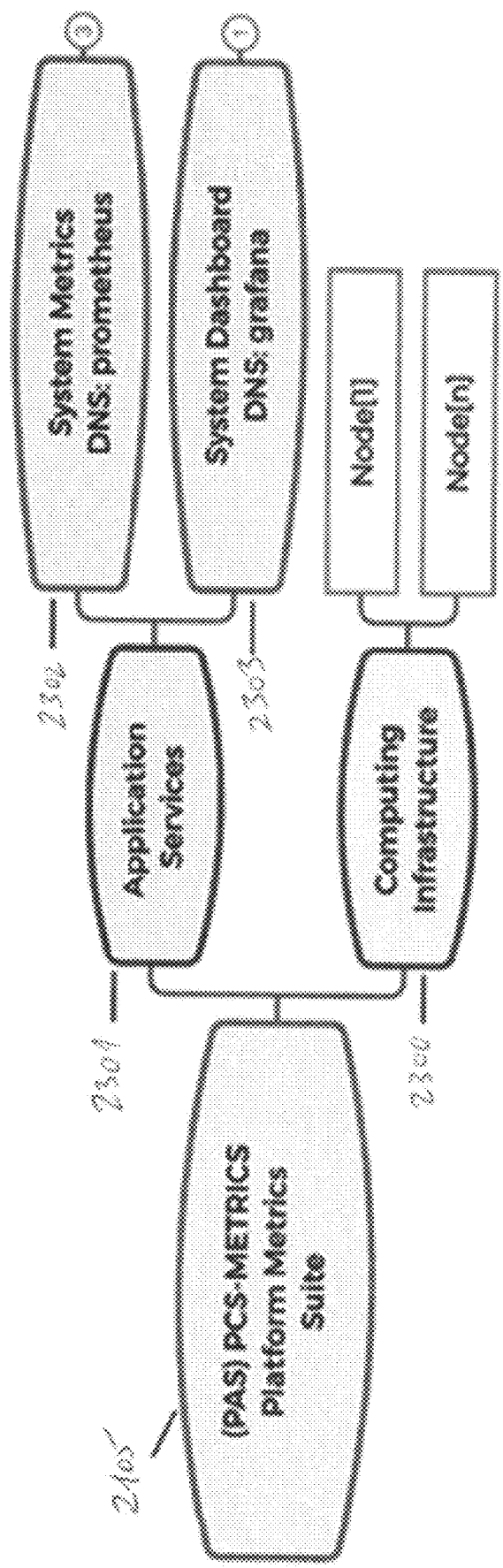
FIG. 44 is a block diagram illustrating a PCS Platform Metrics Suite in accordance with one or more embodiments of the present disclosure.

FIG. 44 is a block diagram illustrating a PCS Platform Metrics Suite in accordance with one or more embodiments of the present disclosure. The Platform Core Services 2087 may include the Platform Metrics Suite (PCS-METRICS) 2105. The PCS-METRICS 2105 may acquire various performance metrics from the platform's infrastructure and applications and may record them in a temporal database. The PCS-METRICS 2105 may then present these metrics to the system administrators in the form of dashboards, that may enable them to monitor, evaluate and troubleshoot of the platform in real-time. The PCS-METRICS may be implemented using system reliability engineering tools developed by Prometheus and Grafana.

In some embodiments, the PCS-METRICS 2105 may be implemented as a resident part of a larger datacenter infrastructure, or on a standalone, Computing Infrastructure 2300 that may include one or more computing nodes.

In some embodiments, the PCS-METRICS 2105 may include two Application Services 2301. The Prometheus service 2302 which may be used to acquire metrics data from the platform in real-time, may use the open-source application Prometheus. The Grafana service 2303 may present these system metrics to the system administrators in the form of dashboards, that may enable them to monitor, evaluate and troubleshoot of the platform in real-time, and may use the open-source application Grafana.

In some embodiments, the Platform Core Services Suite 2087 may implement one or more interfaces to enable external users to interact with the feature. These user interfaces (UI's) may be implemented within the Platform Access Portal Suite 2003 and made available through the Platform Frontend 2001.

In some embodiments, these UI's may include:
1) Administrative and consumer websites to enable access to the feature from a web browser
2) Administrative and consumer Client API Gateways to enable access to the feature by smart client applications. Desktop and mobile applications may be supported.

Figure 45:
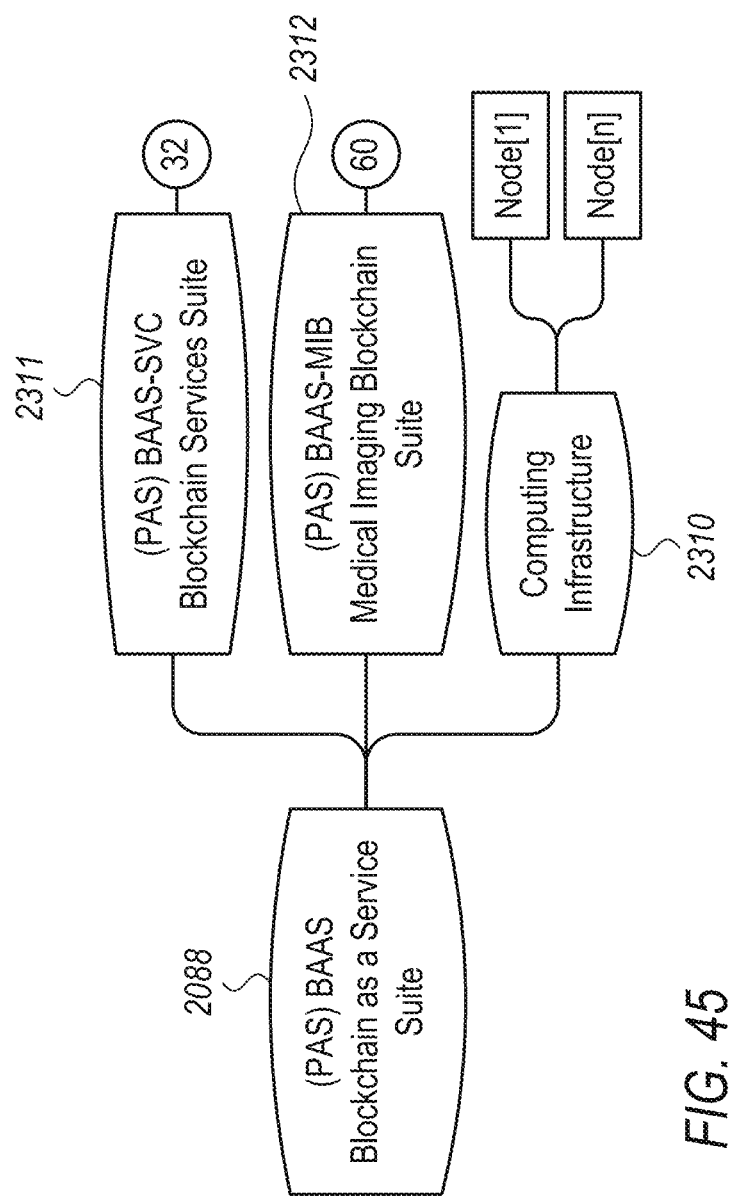
FIG. 45 is a block diagram illustrating a Blockchain as a Service Suite in accordance with one or more embodiments of the present disclosure.

FIG. 45 is a block diagram illustrating a Blockchain as a Service Suite in accordance with one or more embodiments of the present disclosure. The "Blockchain as a Service Suite" (BAAS) 2088 may be a cornerstone of the platform, serving as the platform level blockchain storage feature. The BAAS 2088 may be implemented using blockchain, distributed ledger, and supporting technologies to yield a platform service that may highly available, scalable, performant, and robust. The BAAS 2088 may provide the immutable medium for transparency, accountability, and "trust" among stakeholders that is the signature of the Platform.

In some embodiments, the strength of the immutability of a distributed ledger, blockchain system may be proportional to the number of computing nodes within the infrastructure that may hold copies of the given blockchain. For this reason, a design recommendation may be that the BAAS 2088 may be implemented on a standalone, Computing Infrastructure 2310 that may include dedicated computing nodes and clusters. This may provide an opportunity to optimize the BAAS 2088 according to its unique requirements for operations and computing infrastructure.

In some embodiments, the Blockchain as a Service Suite 2088 may include two, component platform application suites: the Blockchain Services Suite 2311, and the Medical Imaging Blockchain Suite 2312 where:
1) The Blockchain Services Suite 2311 may be a generic Blockchain as a Service (BaaS) platform which may implement a blockchain based, distributed ledger system.
2) The Medical Imaging Blockchain Suite 2312 may be a proprietary BaaS platform that may include features to efficiently handle medical imaging data, the clinical operations that accompany it, and the integration of these features into the healthcare operations ecosystem.

In some embodiments, the Blockchain as a Service Suite 2088 may be a required, platform level application suite, and may be accessible to any application running on the Platform.

Figure 46:
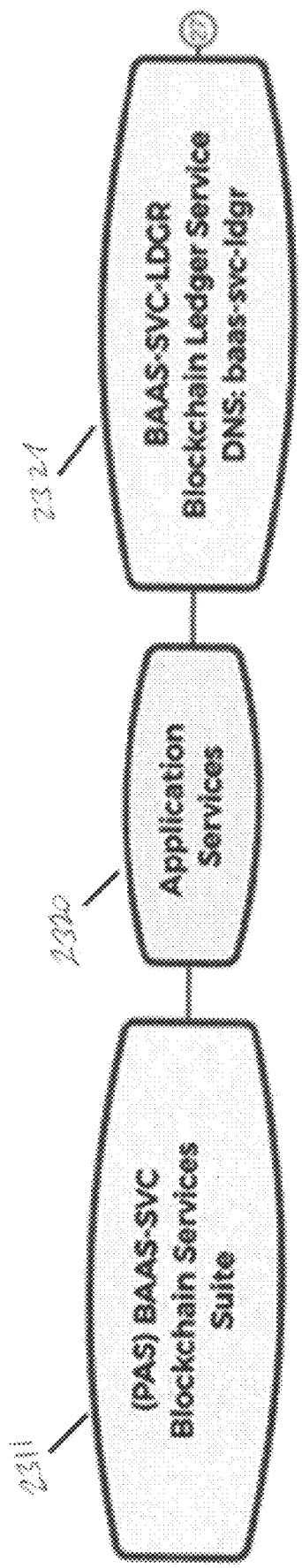
FIG. 46 is a block diagram illustrating a BAAS-SVC-LDGR Blockchain Ledger Service in accordance with one or more embodiments of the present disclosure.

FIG. 46 is a block diagram illustrating a BAAS-SVC-LDGR Blockchain Ledger Service in accordance with one or more embodiments of the present disclosure. The Blockchain Services Suite (BAAS-SVC) 2311 may implement a generic blockchain based, distributed ledger, service. The BAAS-SVC 2311 may include a set of Application Services 2320 that may implement its functionality. This set of Application Services 2320 may include a single service application: the Blockchain Ledger Service (BAAS-SVC-LDGR) 2321. The BAAS-SVC-LDGR 2321 may implement the API to be used to interact with the generic blockchain as a service platform. The BAAS-SVC-LDGR 2321 may be written in GO (Golang), a programming language developed by Google to utilize the resources and features of modern CPUs, non-transient computing memory, networks, and contemporary cloud-native infrastructure more effectively.

Figure 47:
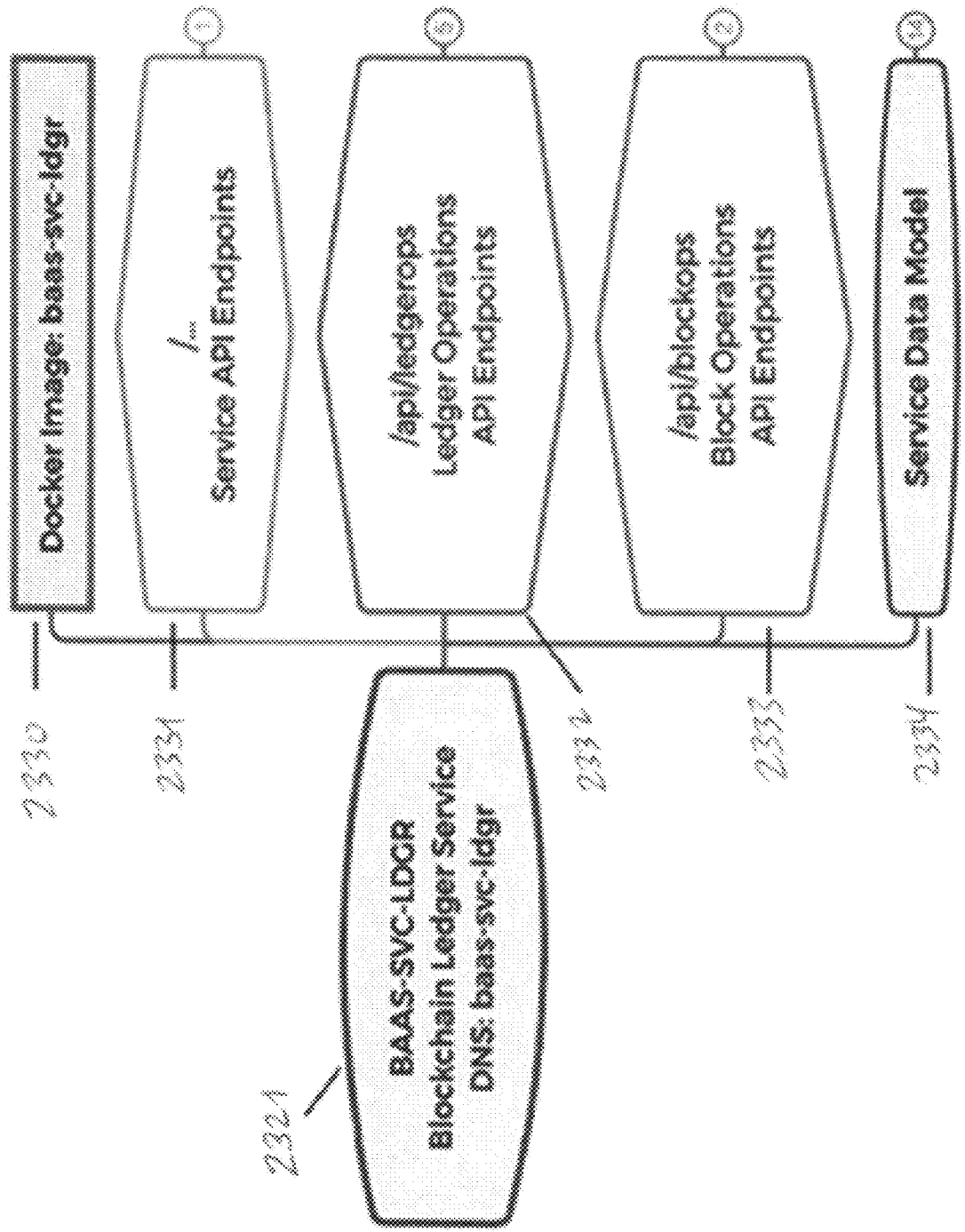
FIG. 47 is a block diagram illustrating a Blockchain Ledger Service in accordance with one or more embodiments of the present disclosure.

FIG. 47 is a block diagram illustrating the Blockchain Ledger Service 2321 in accordance with one or more embodiments of the present disclosure.

Figure 48:
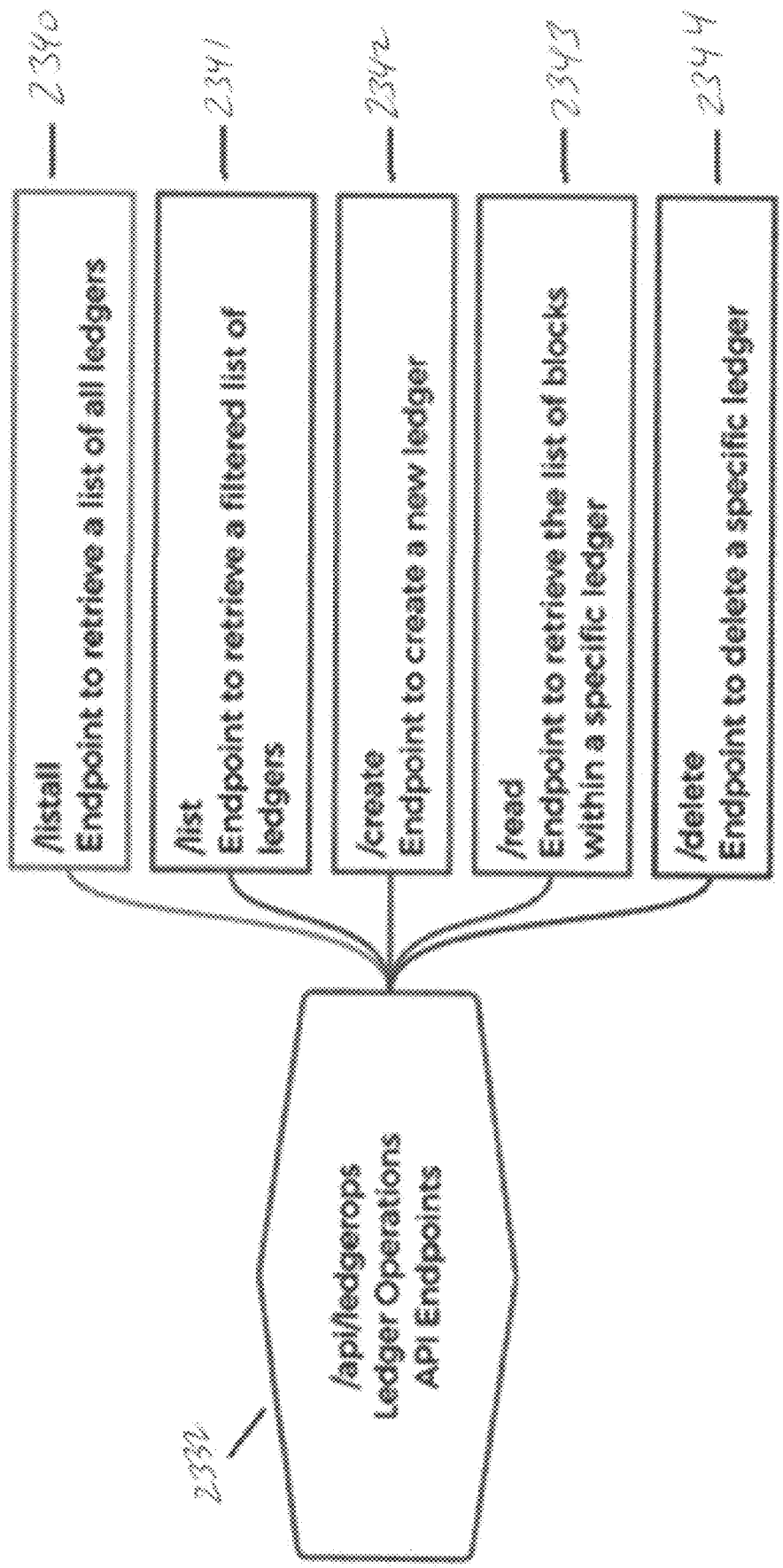
FIG. 48 is a block diagram illustrating BAAS-SVC-LDGR Ledger API Endpoints in accordance with one or more embodiments of the present disclosure.

FIG. 48 is a block diagram illustrating BAAS-SVC-LDGR Ledger API Endpoints 2332 in accordance with one or more embodiments of the present disclosure.

Figure 49:
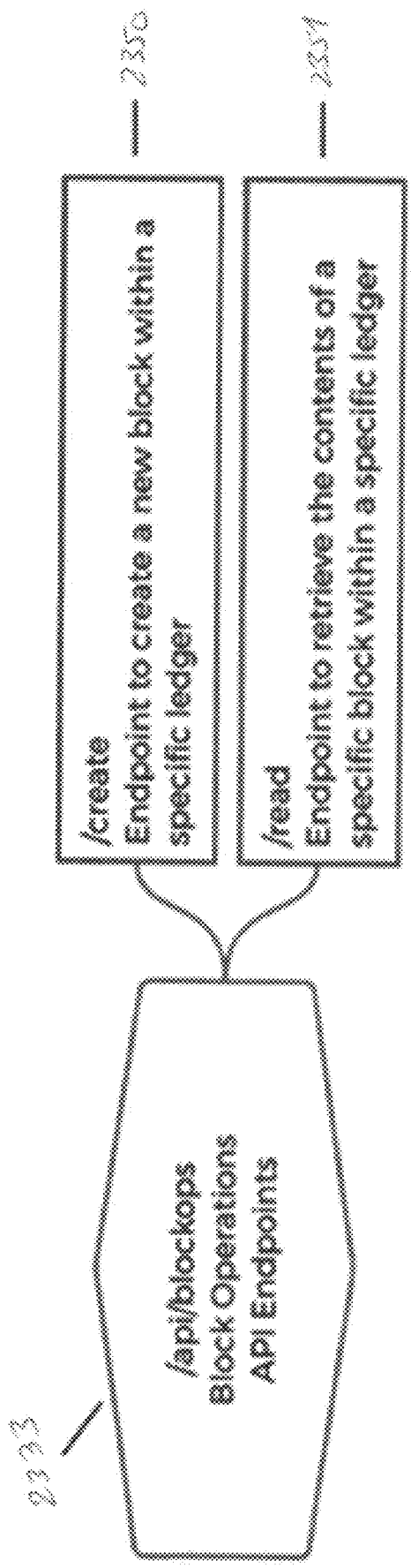
FIG. 49 is a block diagram illustrating BAAS-SVC-LDGR Ledger Block Operations API Endpoints in accordance with one or more embodiments of the present disclosure.

FIG. 49 is a block diagram illustrating BAAS-SVC-LDGR Ledger Block Operations API Endpoints 2333 in accordance with one or more embodiments of the present disclosure.

In some embodiments, the Blockchain Ledger Service (BAAS-SVC-LDGR) 2321 may receive a request from applications running on the platform on the internal network of the Platform Backend Services 2003 and may implement a REST API. The BAAS-SVC-LDGR 2321 API commands may be divided into three functional groups: the Service API Endpoints Group 2331, the Ledger Operations API Endpoints group 2332, and the Block Operations API Endpoints group 2333.

In some embodiments, the Blockchain Ledger Service API Endpoints 2331 may include HTTP endpoints that every service on the Platform may be required to implement. These endpoints may be currently specified as a REST API using the HTTP protocol. In other embodiments, the interface may be replicated under the gRPC protocol to provide an alternative communications method. This interface may be accessible on the Platform Backend Services 2003 network.

In some embodiments, the Blockchain Ledger Service API Endpoints 2331 may conform to the PCS-GRS Service API Endpoint specification described hereinabove.

In some embodiments, the Blockchain Ledger Service may include Ledger Operations API Endpoints 2332 that may further include network communications endpoints that may implement operations on the blockchain ledgers. These endpoints may be currently specified as a REST API using the HTTP protocol. In some embodiments, the interface may be replicated under the gRPC protocol to offer an alternative communications method. This interface may be accessible on the Platform Backend Services 2003 network.

In some embodiments, the Blockchain Ledger Service may include Block Operations API Endpoints 2333 that may further include network communications endpoints that may implement operations on the blocks within the specified blockchain ledger. These endpoints may be currently specified as a REST API using the HTTP protocol. In other embodiments, the interface may be replicated under the gRPC protocol to offer an alternative communications method. This interface may be accessible on the Platform Backend Services 2003 network.

In some embodiments, with regard to most of the Blockchain Ledger Service, Block Operations API Endpoint(s) 2333 may receive HTTP requests using the POST method. These requests may include a data payload in the HTTP request body which may have a defined format and may be referred to as the request data transfer object (DTO). The DTO may be described in the application source code.

The /create Endpoint 2350: HTTP POST may create a new block within the specified blockchain ledger.

The /read Endpoint 2351: HTTP POST may retrieve the contents of the specified block within a specific blockchain ledger.

Figure 50:
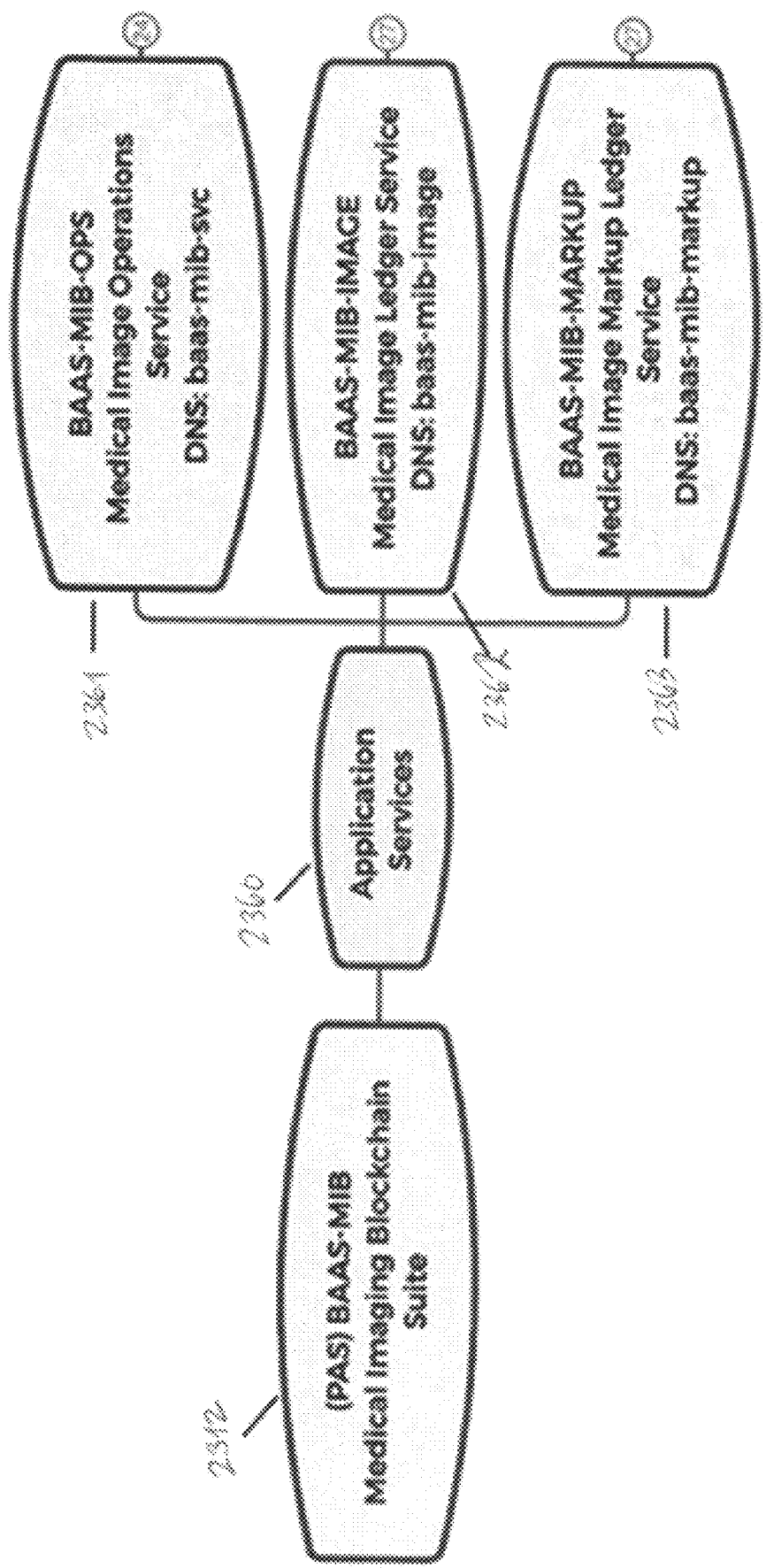
FIG. 50 is a block diagram illustrating a Medical Imaging Blockchain Suite in accordance with one or more embodiments of the present disclosure.

FIG. 50 is a block diagram illustrating a Medical Imaging Blockchain Suite in accordance with one or more embodiments of the present disclosure. The Medical Imaging Blockchain Suite (BAAS-MIB) 2312 may implement a blockchain based, distributed ledger service, that may be specifically designed to meet the operational needs of medical imaging. The BAAS-MIB 2312 may include a set of Application Services 2360 that may include three service components: the Medical Image Operations Service (BAAS-MIB-OPS) 2361, the Medical Image Ledger Service (BAAS-MIB-IMAGE) 2362, and the Medical Image Markup Ledger Service (BAAS-MIB-MARKUP) 2363. The BAAS-MIB 2312 may be structurally diagramed in FIG. 35, and briefly described in the following.

In some embodiments, the Medical Image Operations Service 2361 may implement aggregate operation on the medical imaging data. These operations may involve any or all components of the Medical Imaging Blockchain Suite 2312.

In some embodiments, the Medical Image Ledger Service 2362 may implement the operations for storage of the original medical images within the blockchain ledger system. These operations may be similar to those of the BAAS-SVC-LDGR 2321 service as described hereinabove.

In some embodiments, the Medical Image Markup Ledger Service 2363 may implement the operation for storage of the medical image markup data within the blockchain ledger system. This data may be created when analyzing and processing the associated medical images.

In some embodiments, the Medical Imaging Blockchain Suite 2312 may be a required, platform application suite, and may be accessible to any application running on the Platform.

Figure 51:
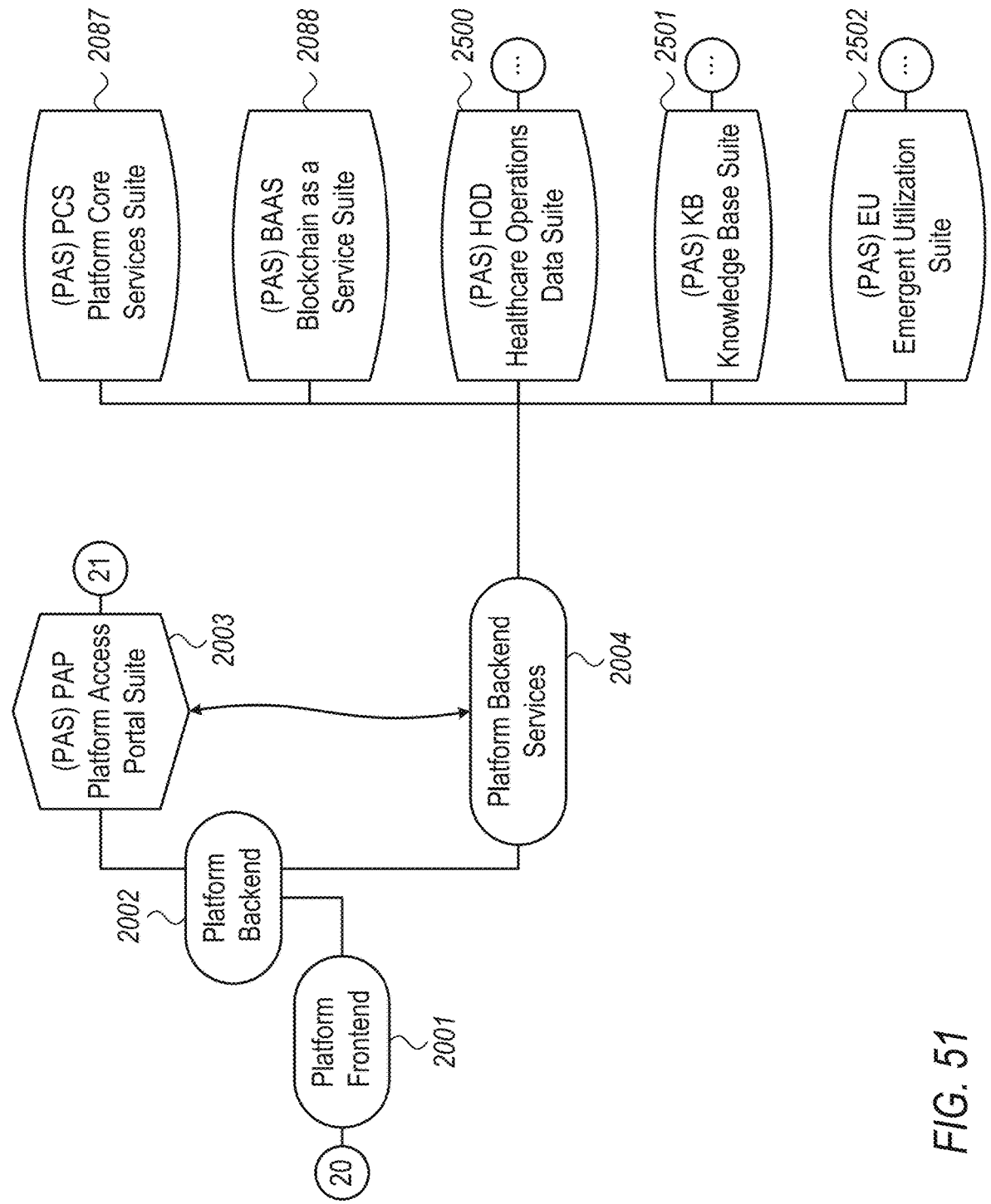
FIG. 51 is a block diagram illustrating a system architecture diagram of the CMA Platform 10 in accordance with one or more embodiments of the present disclosure.

FIG. 51 is a block diagram illustrating a system architecture diagram of the CMA Platform 10 in accordance with one or more embodiments of the present disclosure. The embodiment of Emergent Utilization on the platform may include four, top-level platform application suites (PAS's) in addition to the Platform features as described hereinabove. As shown in FIG. 51, these platform application suites may include Operations Data Reference Suite (ODR) 2500, the Knowledge Base Suite (KB) 2501, and the Emergent Utilization Suite (EU) 2502.

Figure 52:
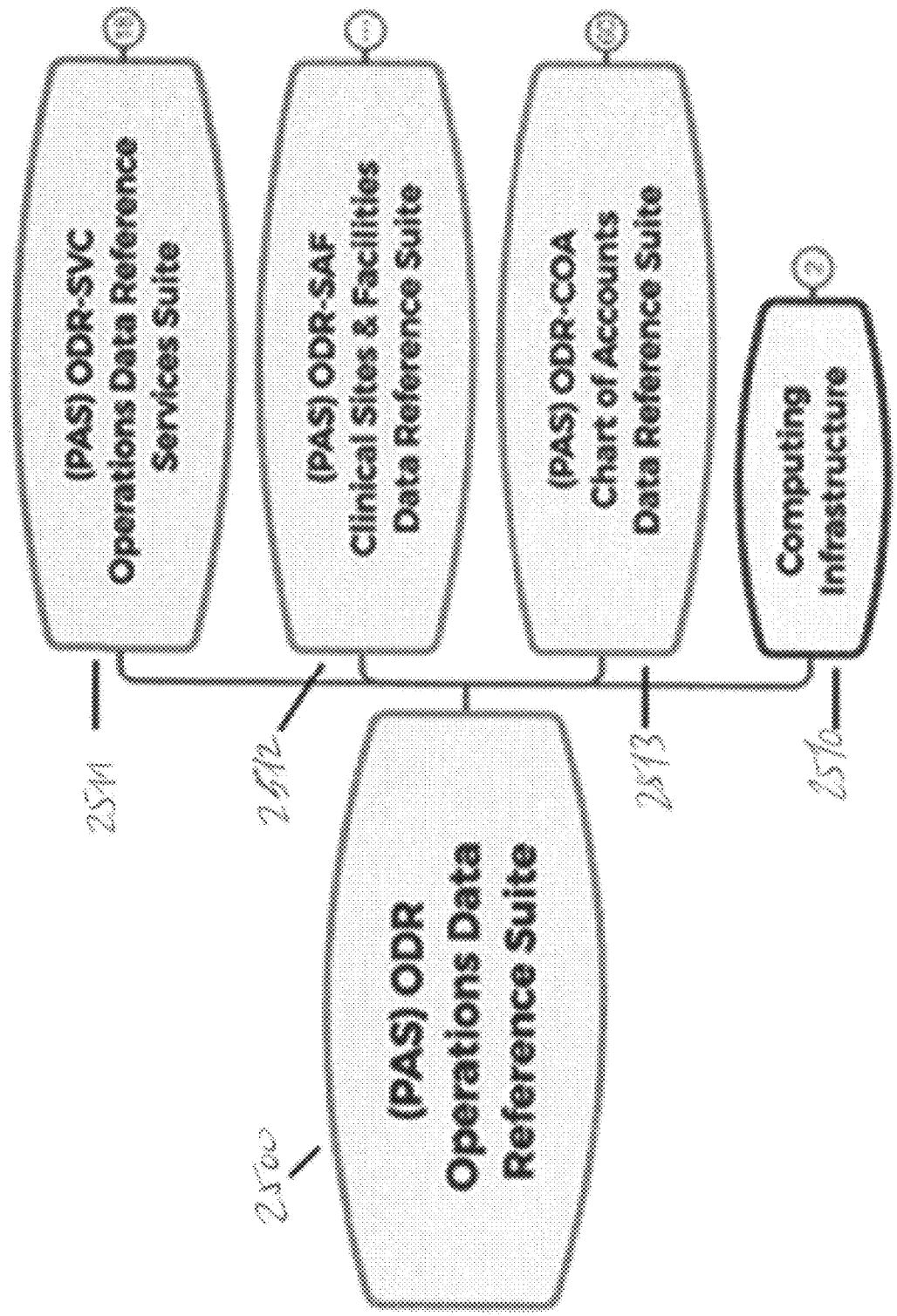
FIG. 52 is a block diagram illustrating an Operations Data Reference Suite Architecture in accordance with one or more embodiments of the present disclosure.

FIG. 52 is a block diagram illustrating an Operations Data Reference Suite Architecture in accordance with one or more embodiments of the present disclosure. The Operations Data Reference Suite (ODR) 2500 may be a suite of data repositories that may include reference data to support common healthcare operations. Examples of such data may be lists of operating sites, facilities within those sites, and charts of accounts.

In some embodiments, the ODR 2500 may be implemented as a resident part of a larger datacenter infrastructure, or on a standalone, "Computing Infrastructure" 2510 that may include one or more computing nodes.

In some embodiments, the ODR 2500 may internally be hierarchically structured and may include a PAS for each type of data. The Data Operations Reference Suite 2500 may include three, platform application suites: the Operations Data Reference Services Suite 2511, the Clinical Sites & Facilities Data Reference Suite 2512, and the Chart of Accounts Data Reference Suite 2513 as shown in FIG. 52.

In some embodiments, the Operations Reference Data Services Suite 2511 may implement aggregate operations involving the other application suites within the Operations Data Reference Suite 2500.

In some embodiments, the Clinical Sites & Facilities Data Reference Suite 2512 may include database services for clinical sites and the facilities within those sites, and a service to perform aggregate operations involving site and facility data. The suite may also include services to record and maintain blockchain ledgers that may include snap shots of the contents of each database to form an historical record of changes in the site and facilities database content.

In some embodiments, the Chart of Accounts Data Reference Suite 2513 may include a database service for storage of the organization's Chart of Accounts. The suite may also include a service to record and to maintain a blockchain ledger that may include snap shots of the database content to form an historical record of changes in the chart of accounts database.

In some embodiments, the Operation Data Reference Suite 2500 may be accessible to any application running on the Platform. The ODR 2500 may be also required to support the implementations of the Emergent Utilization Suite 202.

In some embodiments, the Operations Data Reference Suite 2500 may implement one or more interfaces to enable external users to interact with the feature. These user interfaces (UI's) may be implemented within the Platform Access Portal Suite 2003 and may be made available through the Platform Frontend 2001.

In some embodiments, these UI's may include:
3) Administrative and consumer websites to enable access to the feature from a web browser
4) Administrative and consumer Client API Gateways to enable access to the feature by smart client applications. Desktop and mobile applications may be supported.

Figure 53:
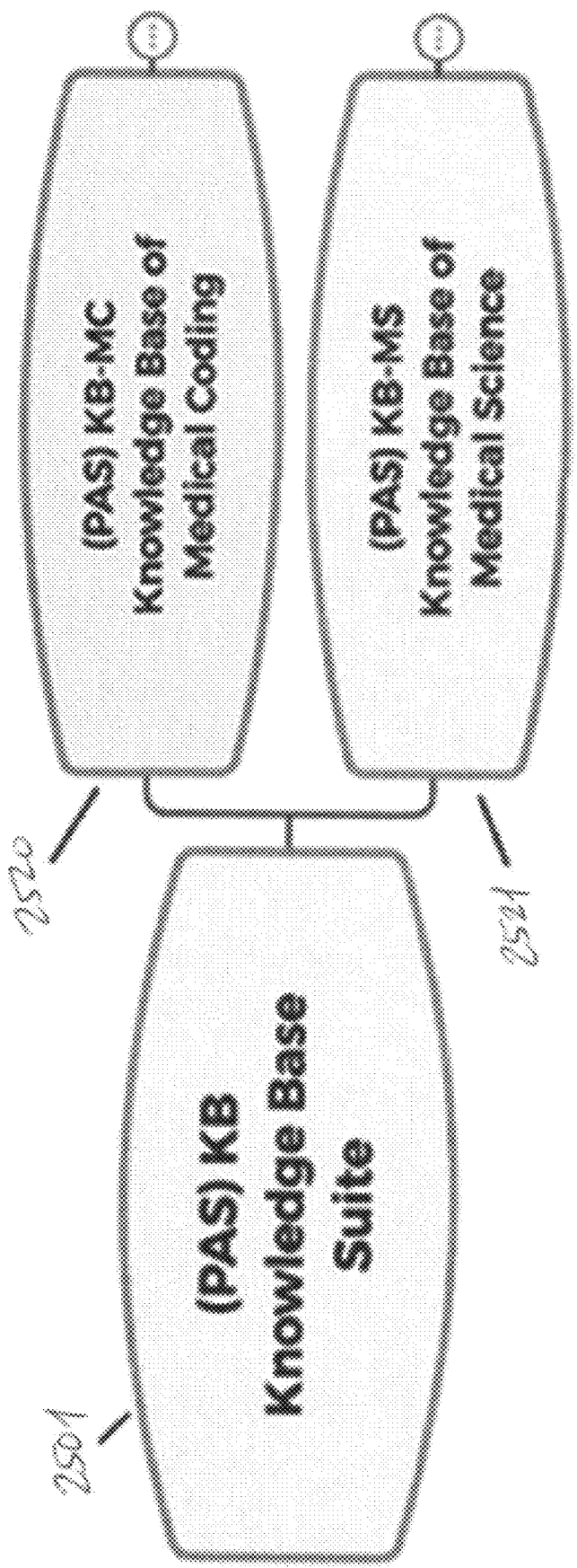
FIG. 53 is a block diagram illustrating a Knowledge Base Suite Architecture in accordance with one or more embodiments of the present disclosure.

FIG. 53 is a block diagram illustrating a Knowledge Base Suite Architecture in accordance with one or more embodiments of the present disclosure. The Knowledge Base Suite (KB) 2501 may include the platform's knowledge systems. A Knowledge Base 201 may be defined as a platform application that autonomously acquires, structures, stores, and operates upon data from a specific target on the internet to yield specific information or knowledge regarding the target's content. This knowledge may be used by other features on the platform, or users of the Platform.

In some embodiments, internally, the Knowledge Base Suite 2501 may be hierarchically structured and may include a PAS for each category of target. The Knowledge Base Suite 2501 may include two such categories: the Knowledge Base of Medical Coding 2520, and the Knowledge Base of Medical Science 2521. In addition to the specific knowledge base service suites, each category may include an application suite to perform aggregate operations across knowledge bases within the suite.

In some embodiments, the Knowledge Base of Medical Coding 2520 may be a second level platform application suite that may organize a series of third level knowledge base suites specifically target, but are not limited to ICD-10, MS-DRG, and CPT codes. The KB-MC 2520 may use the Blockchain as a Service Suite 2088 services to store its data and a temporal log of its operations to form an auditable path and to support temporal reproducibility. This may be to support, transparency, auditability, and immutability of this information.

In some embodiments, the Knowledge Base of Medical Science 2521 may be a second level platform application suite that may organize a series of third level knowledge base suites specifically target. Examples of such targets may include but are not limited to the Cardiopulmonary, Gastrointestinal, Bariatric medical fields. The KB-MS 2521 may use the Blockchain as a Service Suite 2088 services to store its data and a temporal log of its operations to form an auditable path and to support temporal reproducibility. This may be to support, transparency, auditability, and immutability of this information.

In some embodiments, the Knowledge Base Suite 2501 may be accessible to any application running on the Platform. The KB suite 2501 may also be required to support the implementations of the Emergent Utilization Suite 2502.

Figure 54:
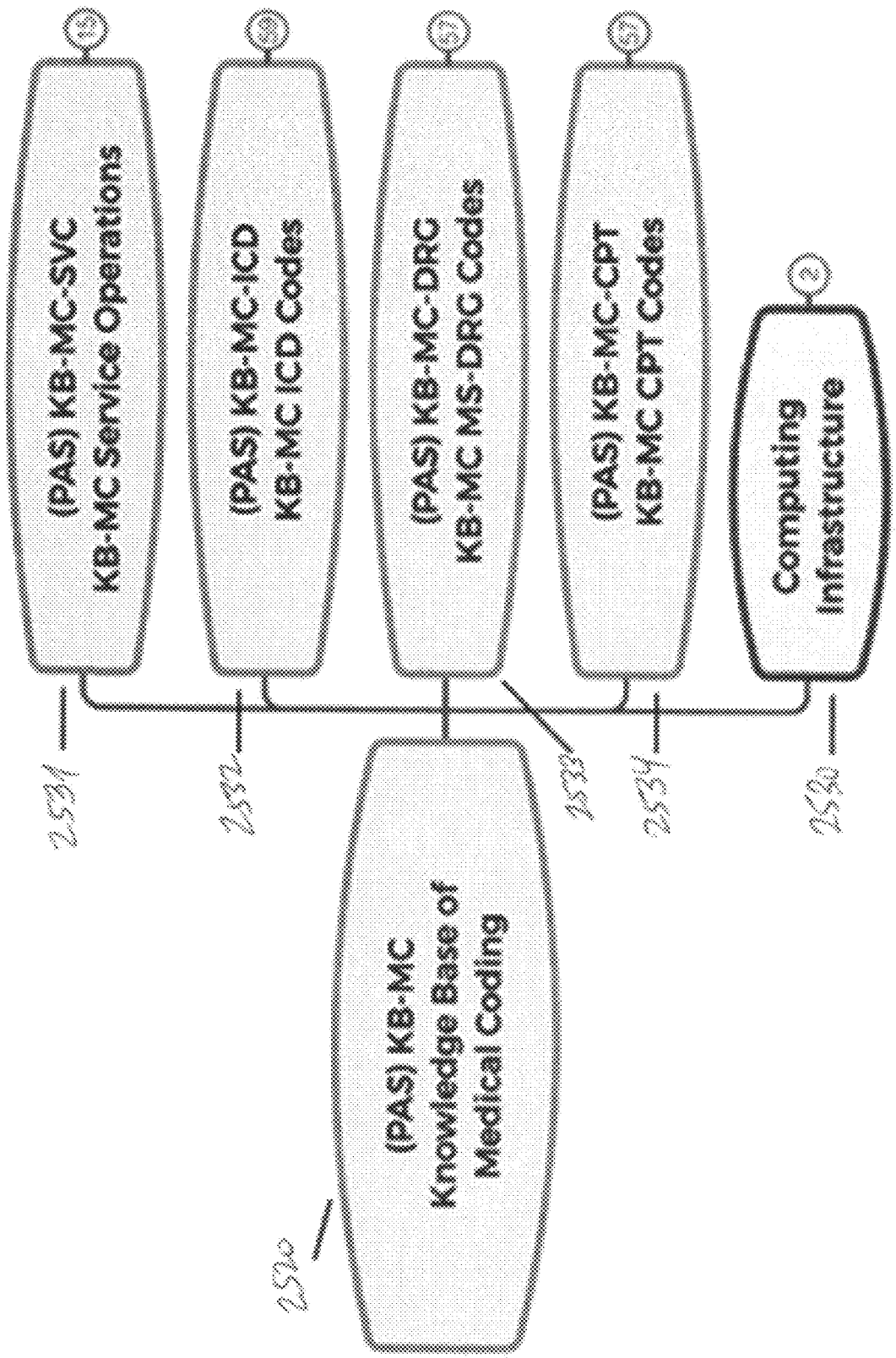
FIG. 54 is a block diagram illustrating a Knowledge Base of Medical Coding Architecture in accordance with one or more embodiments of the present disclosure.

FIG. 54 is a block diagram illustrating a Knowledge Base of Medical Coding Architecture in accordance with one or more embodiments of the present disclosure. Knowledge of medical coding may be a required component of utilization management. The Knowledge Base of Medical Coding (KB-MC) 2520 may fulfill this requirement. The KB-MC 2520 may serve three purposes: The first purpose may be to autonomously acquire and maintain of a body of knowledge of medical coding, as described hereinabove. The second purpose may be to employ the body of knowledge to return an accurate and complete assignment of medical codes associated with a presented clinical document. Finally, the third purpose may be that the KB-MC 2520 may also provide translation between medical coding standards as this may vary among payer requirements. The KB-MC 2520 may use the ICD (currently ICD-10) medical coding standard as the basis for its operations as this standard is international, and the most detailed and specific of the major medical coding standards. The KB-MC 2520 may use its translation features to convert its results into the other supported medical coding standards.

In some embodiments, the KB-MC 2520 may be implemented as a second-level hierarchical architecture within the Knowledge Base Suite (KB) 2501, where the next level of the hierarchy may also include of Platform Application Suites (PAS's). These PAS's may include but are not limited to the following:

1) The KB-MC Service Operations Suite 2531 may implement services to perform aggregate and administrative operations over features of the KB-MC 2520 as a whole. These aggregate features may include the translation of medical codes between the supported medical coding standards.
2) The KB-MC ICD Codes Suite 2532 may be the core PAS of the KB-MC 2520. It may implement automated knowledge acquisition of the ICD (International Classification of Diseases) medical codes, and all operations and features associated with the ICD codes. In addition, the KB-MC ICD Codes Suite 2532 may use Natural Language Processing (NLP) and to read, interpret, and to assign ICD medical codes to submitted clinical documents.
3) The KB-MC MS-DRG Codes Suite 2533 may implement automated knowledge acquisition of the MS-DRG (Medicare Severity Diagnosis Related Groups) medical codes, and all operations and features associated with the codes.
4) The KB-MC CPT Codes Suite 2534 may implement automated knowledge acquisition of the CPT (Current Procedural Terminology) medical codes, and all operations and features associated with the codes.

In some embodiments, the KB-MC 2520 may be implemented as a resident part of a larger datacenter infrastructure, or on a standalone, Computing Infrastructure 2530 that may include one or more computing nodes. The KB-MC 2520 services may be available to any applications running on the Platform.

Figure 55:
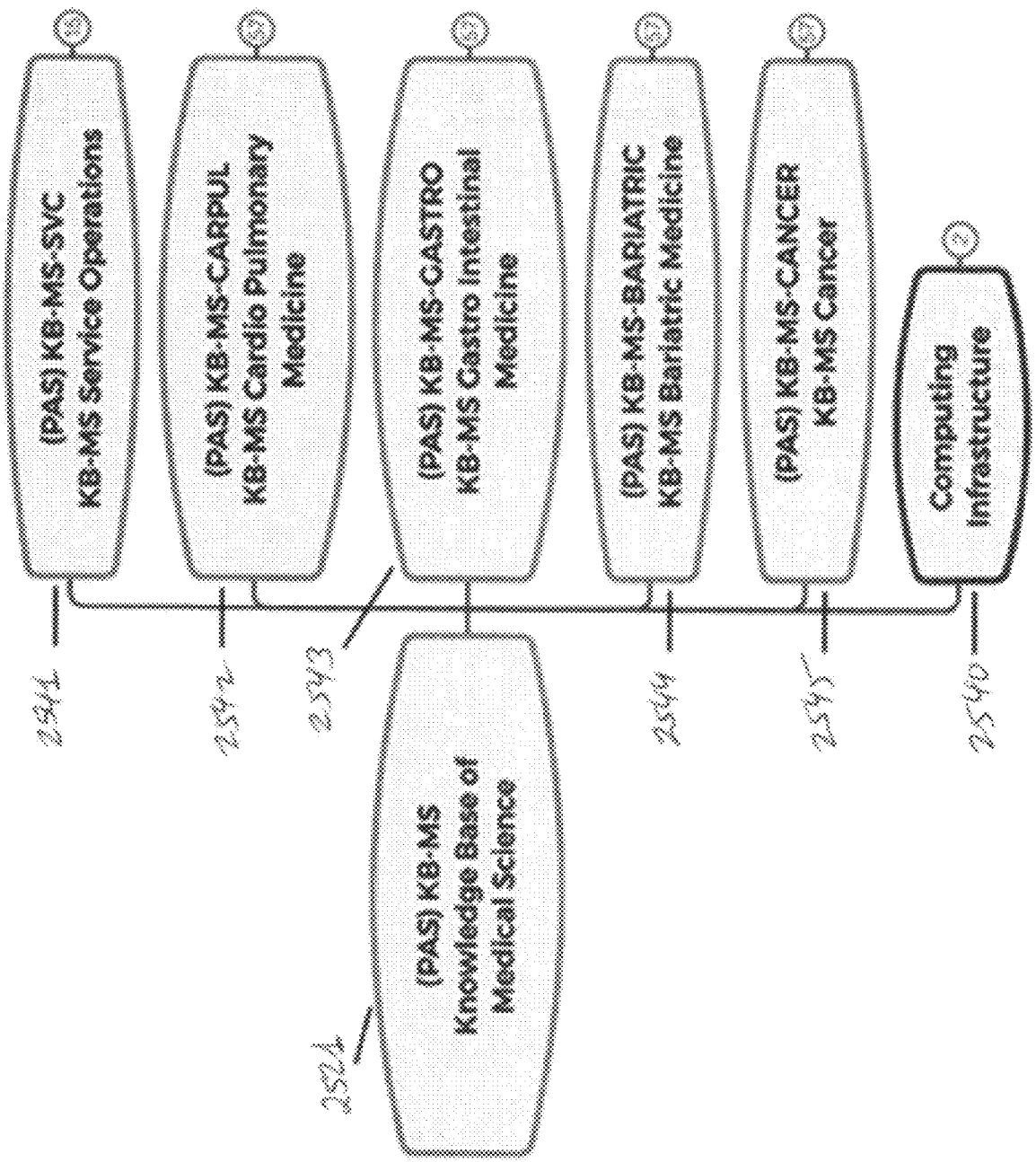
FIG. 55 is a block diagram illustrating a Knowledge Base of Medical Science Architecture in accordance with one or more embodiments of the present disclosure.

FIG. 55 is a block diagram illustrating a Knowledge Base of Medical Science Architecture in accordance with one or more embodiments of the present disclosure. Knowledge of medical science may be needed for the automated determination of medical necessity in medical claims adjudication. This may be a primary objective of the platform design. The purpose of the Knowledge Base of Medical Science (KB-MS) 2521 may fulfill the functional requirements of the Knowledge Base of Medical Science. This base of medical knowledge may be autonomously acquired, globally, from peer-reviewed, community accepted, published sources, and it may be stored in temporal ledgers within the Blockchain as a Service Suite 2088 as described hereinabove to provide transparency, auditability, and immutability.

In some embodiments, the KB-MS 2521 may be implemented as a second-level hierarchical architecture within the Knowledge Base Suite (KB) 2501. The next level of the hierarchy may also include Platform Application Suites (PAS's). These PAS's may be organized into two functional groups. The first group may include features that may perform aggregate operations that may involve multiple fields of medicine. It may include the KB-MS Service Operations suite 2541 which may implement these operations. The second group may include Platform Application Suites for each supported field of medicine. These may include but are not limited to those presented in FIG. 55, in items 2542 through 2545. As each field of medicine may be a very large topic and the implementation of each knowledge base may be very complex, they will not be presented in detail in this disclosure.

Note that the data elements stored within the KB-MS 2521 may be referenced to the ICD medical codes. Hence, the KB-MS 2521 may carry an operational dependence upon the KB-MC 2520 (Knowledge Base of Medical Coding).

In some embodiments, the KB-MS 2521 may be implemented as a resident part of a larger datacenter infrastructure, or on a standalone, Computing Infrastructure 2540 that may include one or more computing nodes. The KB-MS 2521 services may be available to any applications running on the Platform.

In some embodiments, the Knowledge Base Suite 2501 may implement one or more interfaces to enable external users to interact with the feature. These user interfaces (UI's) may be implemented within the Platform Access Portal Suite 2003 and may be made available through the Platform Frontend 2001.

In some embodiments, these UI's may include:
5) Administrative and consumer websites to enable access to the feature from a web browser
6) Administrative and consumer Client API Gateways to enable access to the feature by smart client applications. Desktop and mobile applications will be supported.

Figure 56:
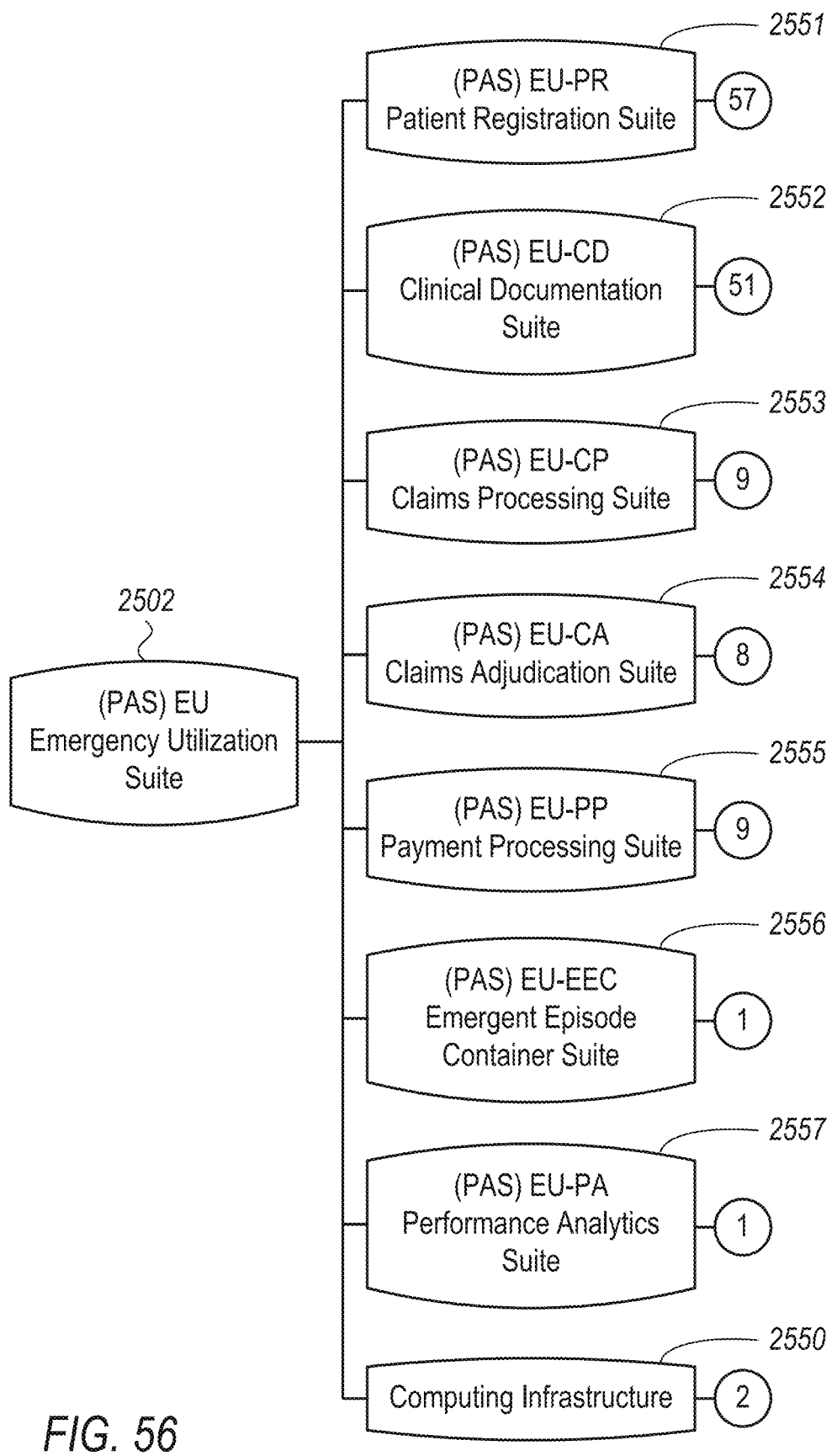
FIG. 56 is a block diagram illustrating an Emergent Utilization Suite Architecture in accordance with one or more embodiments of the present disclosure.

FIG. 56 is a block diagram illustrating an Emergent Utilization Suite Architecture in accordance with one or more embodiments of the present disclosure. The Emergent Utilization Suite (EU) 2502 may include the data and operations that may include the process of Emergent Utilization as described herein throughout this disclosure.

In some embodiments, internally, the Emergent Utilization Suite 2502 may be hierarchically structured and organized into three functional groups of Platform Application Suites The first group is the Emergent Utilization Process Group, which may include a PAS for each phase of the Emergent Utilization process. The second group may include the PAS that may further include the Emergent Episode Container management and interface operations. The final group may include the PAS that may be responsible for the system performance analytics.

In some embodiments, the Emergent Utilization Process Group may include the sequence of operations that may include the EU process as described herein. Each step in the process may be performed by a corresponding Platform Application Suite (PAS) that may include:

1) The Patient Registration Suite 2551 may begin the emergent utilization flow with operations to support patient admission. These operations may include but are not limited to the retrieval of the patient data from the EMR (Electronic Medical Record) system, the creation of the Emergent Episode Container (EEC) 300, and the retrieval of the patient's referral and insurance plan information. Finally, the admissions information is stored in the EEC 300.
2) The Clinical Documentation Suite 2552 may record patient consultation information, that may include the physician-patient conversation, and the physician's notes. The Clinical Documentation Suite 2552 may use NLP (Natural Language Processing) and the services of the KB-MS (Knowledge Base of Medical Science) to compile the patient consult information, physician observations, diagnostic test results, and the information may be stored in the case EEC 300 into a medically coded transcript of the patient care process. The transcript may then be stored in the case EEC 300. This process may be repeated more than once in the course of an emergent episode.
3) The Claims Processing Suite 2553 may retrieve the medically coded transcripts from the EEC 300 of the case when care delivery may be completed. The Claims Processing Suite may use the transcripts and the services of the Knowledge Base of Medical Coding (KB-MC) 2520, the Knowledge Base of Medical Science (KB-MS) 2521, the Knowledge Base of Claims Preparation Requirements (KB-CPR) 2522, combined with clinician review, to create the medical claim. The process may be completed by the storage of the completed claim in the EEC 300 of the case.
4) The Claims Adjudication Suite 2554 may retrieve the completed medical claim and the medically coded transcripts from the EEC 30 of the case when notified of the completion. The Claims Adjudication Suite may use the services of the Knowledge Base of Medical Coding (KB-MC) 2520, and the Knowledge Base of Medical Science (KB-MS) 2521. The Claims Adjudication Suite 2554 may retrieve the medically coded transcripts from the EEC 300 of the case and may remove the clinician review information. The Claims Adjudication Suite 2554 may use the remainder of the transcript information to formulate a series of reference claims based only upon the established medical science. The Claims Adjudication Suite 2554 may compare the content of the submitted claim to those of the reference claims to determine the correlation between them. If the correlation is sufficient, the submitted claim may be marked for payment. If the correlation is not sufficient, the claim may be marked for denial. The result may be then stored in the EEC 300 of the case.
5) The Payment Processing Suite (EU-PP) 2555 may provide an automated payment process for the payment of medical claims. Upon receipt of an adjudication completion notification from the Claims Adjudication Suite 2554, the EU-PP 2555 may retrieve the adjudication result from the EEC 300 of the case. If the result indicates that the claim should be paid, the EU-PP 2555 may engage the appropriate smart contract whose definition may be stored within the Knowledge Base of Payer/Provider Contracts (KB-PPC), to execute the specified transfer of funds from the payer to the provider accounts.

In some embodiments, the Emergent Episode Container Suite (EU-EEC) 2556 may be the data persistence component of the Emergent Utilization Suite 2502 for implementing the Emergent Episode Container and its associated functions as described herein. The EU-EEC Suite 2556 may include the operational API service that supports the operations of the Emergent Utilization Suite 2502, as well as the implementation of the working storage systems that support the in-process Emergent Utilization workflow. The EU-EEC 2556 may also implement the data structures, operations, and transaction interface to the Blockchain as a Service Suite 2088 that may constitute the blockchain infrastructure where the Emergent Episode Containers may be stored.

In some embodiments, the Performance Analysis Suite (EU-PA) 2557 may be the performance evaluation component of the Emergent Utilization Suite 2502. Each service implemented within the Emergent Utilization Suite may be required to send key performance data to the EU-PA 2557. The EU-PA Suite 2557 may aggregate the application and system performance data and may perform analytics that may be used for system optimization. In other embodiments, machine learning and/or robotic process automation may be employed in many of the performance optimizations, thus enabling the EU Suite 2502 to become autonomously self-optimizing.

In some embodiments, the Emergent Utilization Suite 2502 may implement one or more interfaces to enable external users to interact with the feature. These user interfaces (UI's) may be implemented within the Platform Access Portal Suite 2003 and may be made available through the Platform Frontend 2001.

In some embodiments, these UI's may include:
7) Administrative and consumer websites to enable access to the feature from a web browser
8) Administrative and consumer Client API Gateways to enable access to the feature by smart client applications. Desktop and mobile applications will be supported.

Figure 57:
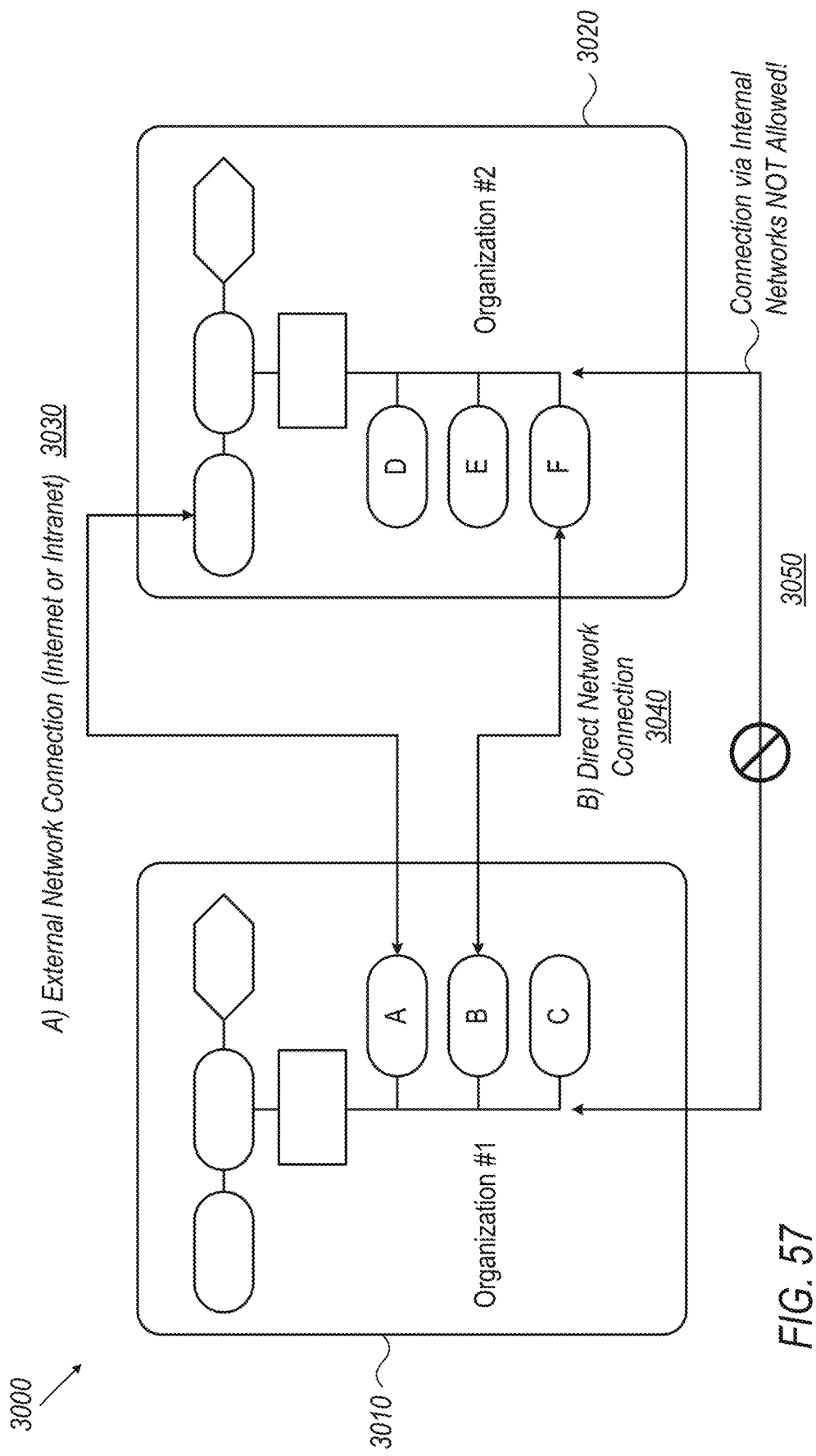
FIG. 57 is a block diagram illustrating Interconnected Platforms in accordance with one or more embodiments of the present disclosure.

FIG. 57 is a block diagram illustrating Interconnected Platforms in accordance with one or more embodiments of the present disclosure. The CMA platform 10 may be designed with a platform-based architecture. In practice, for organizational or operational reasons, it may not be practical to develop or implement all of the operations of the CMA platform 10 on a single platform. To accommodate such scenarios, the CMA platform 10 may include the capability to support operations development in a multi-platform, integrated environment.

In some embodiments, the Platform may include features for the connection of the platform to an external third-party application by use of the Platform Automation Receptor 2081. The PAR 2081 may be used to connect one operational system of one platform to another, or to multiple systems. FIG. 57 illustrates different exemplary embodiments for such platform interconnection.

In some embodiments, in connection option "A", an external network connection may be used, where Platform Application Suite-A is a PAR implemented on a platform associated with Organization #1. The Suite-A PAR may be connected over the external network to the Client API of a platform associated with Organization #2. This may enable the platform associated with Organization #1 to integrate to the platform associated with Organization #2 as a "third-party application". This connection may be driven from the Organization #1 platform.

In some embodiments, in connection option "B", a dedicated, direct network connection may be used. In this case Platform Application Suite-B may be a PAR implemented on the platform associated with Organization #1, and Platform Application Suite-F may be a PAR implemented on the platform associated with Organization #2. Option "B" may be used to implement an inter-platform connection that may be interactive from both ends.

Figure 58:
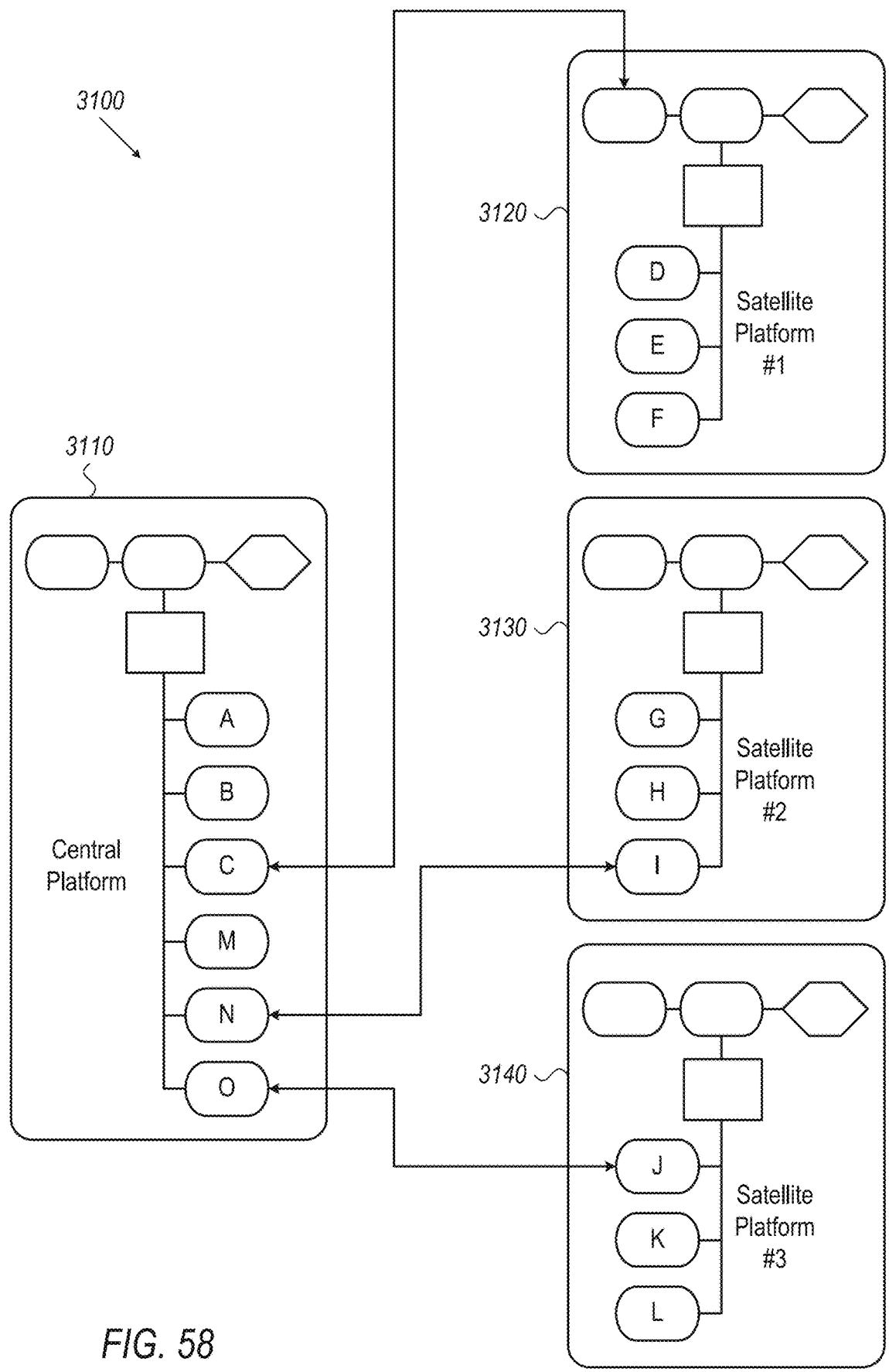
FIG. 58 is a block diagram illustrating Central/Satellite Program Architecture in accordance with one or more embodiments of the present disclosure.

FIG. 58 is a block diagram illustrating Central/Satellite Program Architecture in accordance with one or more embodiments of the present disclosure. Another Platform interconnection structure may that of a "central platform" that may connect to and integrate with multiple satellite platforms as shown in FIG. 58. Note that connection options "A" and "B" may be used together to implement a heterogeneous connection architecture. This capability may be used to create very complex interfaces when the broad range of capabilities for the implementation of a PAR may be considered.

Although the embodiments disclosed herein related to healthcare related claim management—claim document generation and claim adjudication systems, these systems may be applied to any form of insurance such as life insurance, homeowner insurance, and/or car insurance where generally a first user (e.g., a insured client or patient) is receiving services by a second user (e.g., a service provider) where a claim is generated that is paid for by a third user (a payer or an insurance company).

Figure 59:
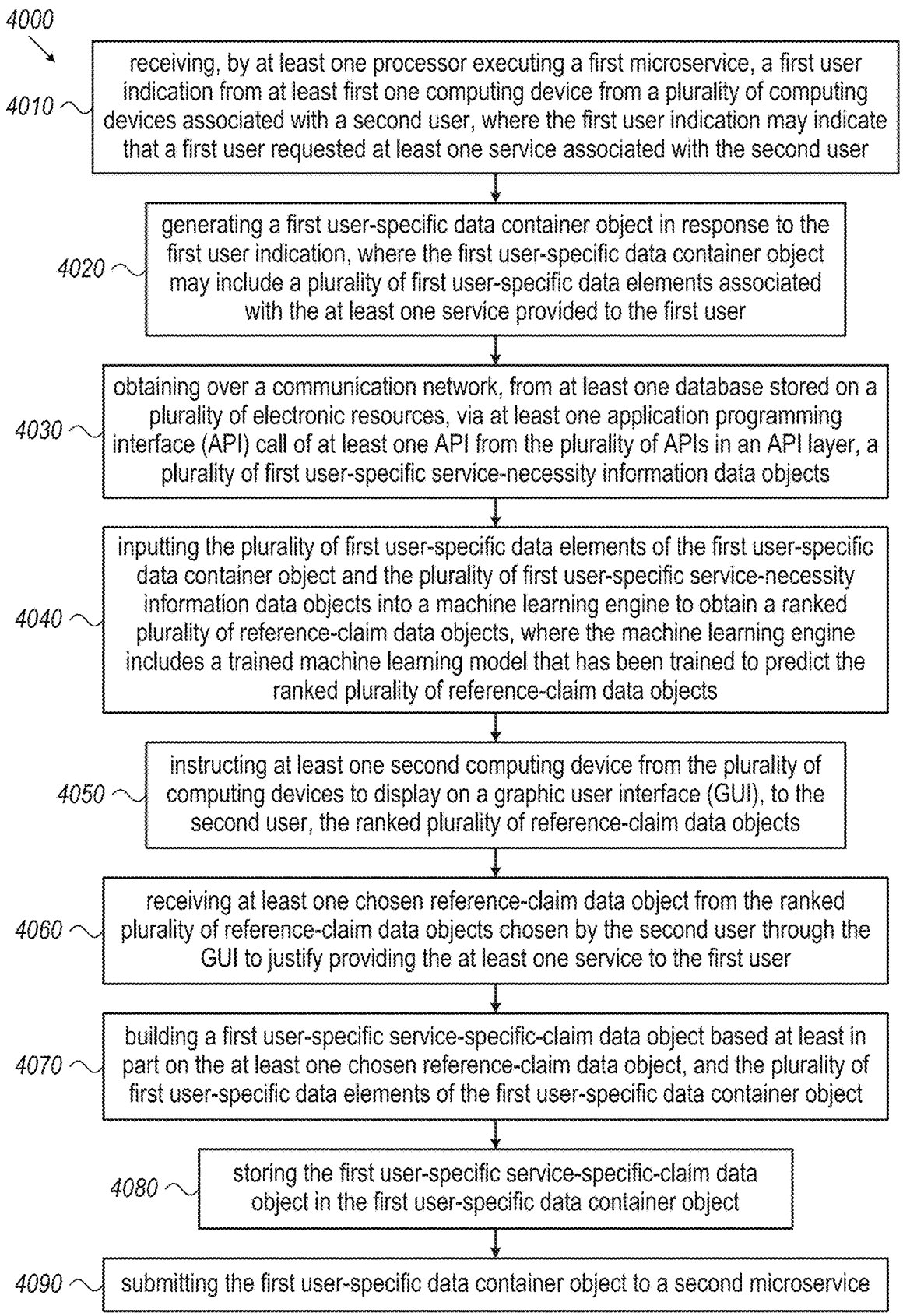
FIG. 59 is a flowchart of a method for generating a first-user-specific service-specific claim data object in accordance with one or more embodiments of the present disclosure.

FIG. 59 is a flowchart of a method 4000 for generating a first-user-specific service-specific claim data object in accordance with one or more embodiments of the present disclosure. The method 4000 may be performed by a first microservice and may be executed by at least one processor. The method 4000 may be the process for an automated generation of a claim (e.g., claim document) to request payment for the services provided by the service provider.

The method 4000 may include receiving 4010, by at least one processor executing a first microservice, a first user indication from at least first one computing device from a plurality of computing devices associated with a second user, where the first user indication may indicate that a first user requested at least one service associated with the second user.

The method 4000 may include generating 4020 a first user-specific data container object in response to the first user indication, where the first user-specific data container object may include a plurality of first user-specific data elements associated with the at least one service provided to the first user.

The method 4000 may include obtaining 4030 over a communication network, from at least one database stored on a plurality of electronic resources, via at least one application programming interface (API) call of at least one API from the plurality of APIs in an API layer, a plurality of first user-specific service-necessity information data objects.

The method 4000 may include inputting 4040 the plurality of first user-specific data elements of the first user-specific data container object and the plurality of first user-specific service-necessity information data objects into a machine learning engine to obtain a ranked plurality of reference-claim data objects, where the machine learning engine includes a trained machine learning model that has been trained to predict the ranked plurality of reference-claim data objects.

The method 4000 may include instructing 4050 at least one second computing device from the plurality of computing devices to display on a graphic user interface (GUI), to the second user, the ranked plurality of reference-claim data objects.

The method 4000 may include receiving 4060 at least one chosen reference-claim data object from the ranked plurality of reference-claim data objects chosen by the second user through the GUI to justify providing the at least one service to the first user.

The method 4000 may include building 4070 a first user-specific service-specific-claim data object based at least in part on the at least one chosen reference-claim data object, and the plurality of first user-specific data elements of the first user-specific data container object.

The method 4000 may include storing 4080 the first user-specific service-specific-claim data object in the first user-specific data container object.

The method 4000 may include submitting 4090 the first user-specific data container object to a second microservice.

In some embodiments, the method 4000 implemented by the generic first microservice in FIG. 59 for generating a user-specific service-specific claim data object may be mapped to the CMA platform 10 embodiments described herein for executing the claim document generator microservices 40 as follows: the first microservice may be the claim document generator microservice 40 and the second microservice may be the claim adjudication microservice 60. The first user may be a patient and the second user may be a provider. The first user indication may be new patient indication from the new patient alert monitor 575. The at least one service may be the at least one medical service provided to the patient by the provider.

In some embodiments, the first user-specific data container object may be the patient-specific data container object such as the emergent episode container (EEC) 300. The plurality of first user-specific data elements may be the plurality of patient-specific data elements such as the consult packages 610_0 . . . 610_n, each patient-specific data element may include patient data associated with the at least one medical service provided to the patient in one or more consults between patient and provider as shown in the embodiments of FIG. 9. The at least one database may the medical knowledge database (e.g., the Knowledge Base of Medical Science 630) that may be stored in the plurality of electronic resources 25A . . . 25B.

In some embodiments, the plurality of first user-specific service-necessity information data objects may be a plurality of patient-specific medical-necessity information data objects that may be fetched by the seeker 920 from the medical knowledge database (e.g., the Knowledge Base of Medical Science 630) shown in FIG. 12. The ranked plurality of reference-claim data objects may be the ranked plurality of reference-claim document objects such as the ranked package recipes 655 that may be displayed to the provider representative such as a physician as shown in FIG. 12. The ranked package recipes may be ranked according to medical necessity as determined by the ground truth of medical knowledge found in the Knowledge Base of Medical Science 630, accepted and agreed upon by both payer and/or provider. The first user-specific service-specific-claim data object may be a patient-specific service-specific-claim file object or the claim that is submitted to the adjudication microservice.

Figure 60:
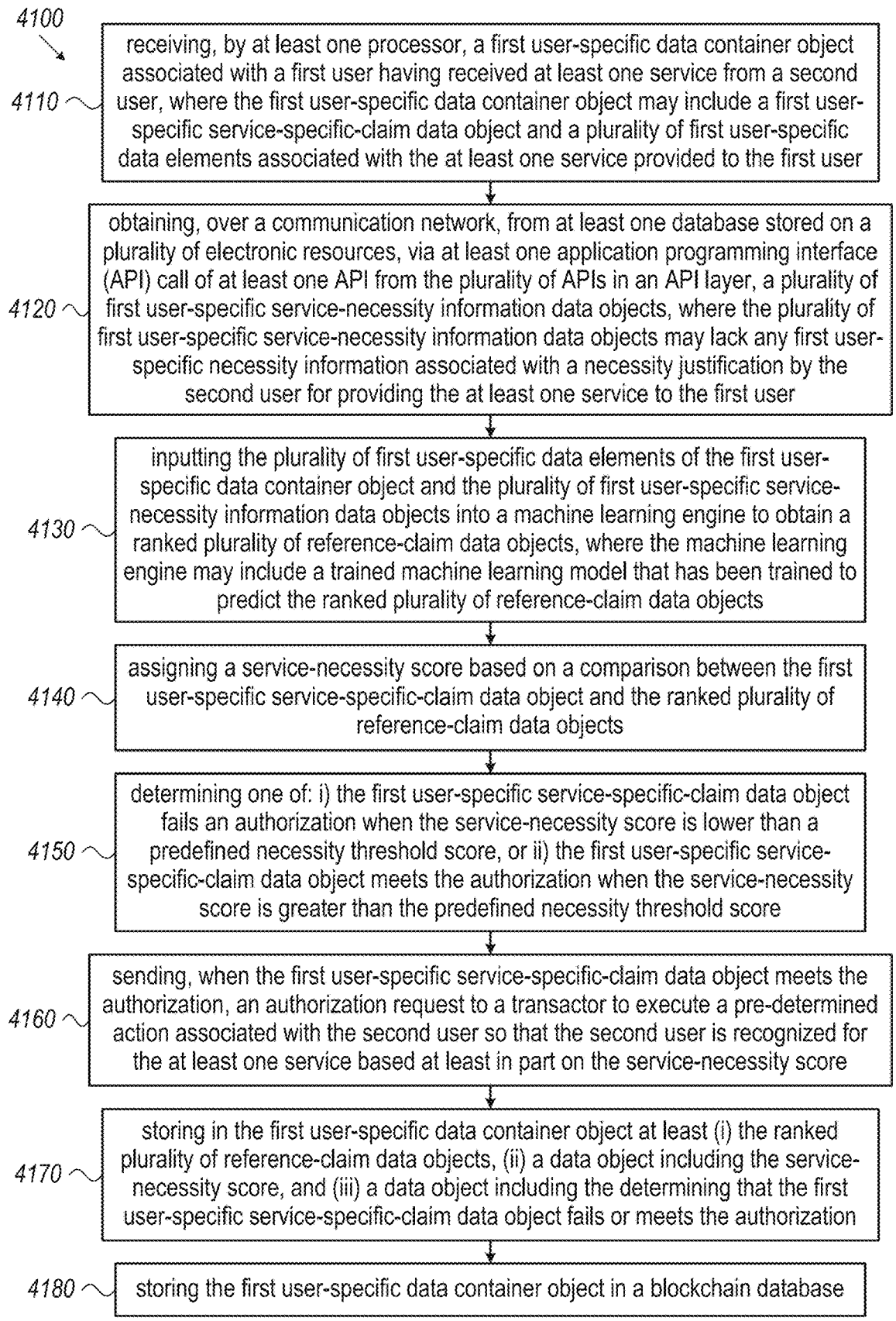
FIG. 60 is a flowchart of a method for determining when a first-user-specific service-specific claim data object meets or fails an authorization in accordance with one or more embodiments of the present disclosure.

FIG. 60 is a flowchart of a method 4100 for determining when a first-user-specific service-specific claim data object meets or fails an authorization in accordance with one or more embodiments of the present disclosure. The method 4100 may be performed by a microservice and may be executed by at least one processor. The method 4100 may be the process for an automated adjudication of a claim (e.g., claim document) to request payment by the first user (e.g., an insured person or an insured entity) for the services provided by the second user (e.g., service provider).

The method 4100 may include receiving 4110, by at least one processor, a first user-specific data container object associated with a first user having received at least one service from a second user, where the first user-specific data container object may include a first user-specific service-specific-claim data object and a plurality of first user-specific data elements associated with the at least one service provided to the first user.

The method 4100 may include obtaining 4120 over a communication network, from at least one database stored on a plurality of electronic resources, via at least one application programming interface (API) call of at least one API from the plurality of APIs in an API layer, a plurality of first user-specific service-necessity information data objects, where the plurality of first user-specific service-necessity information data objects may lack any first user-specific necessity information associated with a necessity justification by the second user for providing the at least one service to the first user.

The method 4100 may include inputting 4130 the plurality of first user-specific data elements of the first user-specific data container object and the plurality of first user-specific service-necessity information data objects into a machine learning engine to obtain a ranked plurality of reference-claim data objects, where the machine learning engine may include a trained machine learning model that has been trained to predict the ranked plurality of reference-claim data objects.

The method 4100 may include assigning 4140 a service-necessity score based on a comparison between the first user-specific service-specific-claim data object and the ranked plurality of reference-claim data objects.

The method 4100 may include determining 4150 one of: i) the first user-specific service-specific-claim data object fails an authorization when the service-necessity score is lower than a predefined necessity threshold score, or ii) the first user-specific service-specific-claim data object meets the authorization when the service-necessity score is greater than the predefined necessity threshold score.

The method 4100 may include sending 4160, when the first user-specific service-specific-claim data object meets the authorization, an authorization request to a transactor to execute a pre-determined action associated with the second user so that the second user is recognized for the at least one service based at least in part on the service-necessity score.

The method 4100 may include storing 4170 in the first user-specific data container object at least (i) the ranked plurality of reference-claim data objects, (ii) a data object including the service-necessity score, and (iii) a data object including the determining that the first user-specific service-specific-claim data object fails or meets the authorization.

The method 4100 may include storing 4180 the first user-specific data container object in a blockchain database.

In some embodiments, the method 4100 implemented by the generic first microservice in FIG. 60 for adjudicating a user-specific service-specific claim data object may be mapped to the CMA platform 10 embodiments described herein for executing the claim adjudication microservices 60 as follows: The microservice may be the claim adjudication microservice 60. The first user may be a patient and the second user may be a provider. The at least one service may be at least one medical service provided to the patient by the provider. The first user-specific data container object may be a patient-specific data container object such as the emergent episode container (EEC) 300. The first user-specific service-specific-claim data object may be a patient-specific service-specific-claim file object (e.g., the submitted claim 930 for adjudication). The plurality of first user-specific data elements may be the plurality of patient-specific data elements such as the consult packages 610_0 . . . 610_n, each patient-specific data element may include patient data associated with the at least one medical service provided to the patient in one or more consults between patient and provider as shown in the embodiments of FIG. 9. The at least one database may be the medical knowledge database (e.g., the Knowledge Base of Medical Science 630) that may be stored in the plurality of electronic resources 25A . . . 25B.

In some embodiments, the plurality of first user-specific service-necessity information data objects may be a plurality of patient-specific medical-necessity information data objects that were fetched by the seeker 1025 from the medical knowledge database (e.g., the Knowledge Base of Medical Science 630) shown in FIG. 13. However, the search query determined by the query builder 1020 may lack or not have any medical necessity justifications given by the provider. Stated differently, the query builder may ignore any of the physician actions shown in the table 800 of FIG. 11 in the search query (e.g., patient diagnosis, prescribed medication, prescribed treatment, and/or prescribed therapy). The ranked plurality of reference-claim data objects may be the ranked plurality of reference-claim document objects such as the ranked package recipes 1030 that are as shown in FIG. 13. These reference claims represented by the reference-claim document objects may be used by the claim comparator 1115 to compare them to the submitted claim 930 for adjudication.

In some embodiments, the service-necessity score may be a medical service necessity score outputted by the claim comparator 1115. The authorization may be the authorization for payment approval if the claim is approved by the pay or deny module 1120. The authorization request may a payment request to the transactor 1205. The predetermined action may be sending a payment to an account of the provider for the at least one medical service provided to the patient. The blockchain database 120 may be a blockchain database for storing the patient-specific data container object (e.g., the EEC blockchain DB 140).

Figure 61:
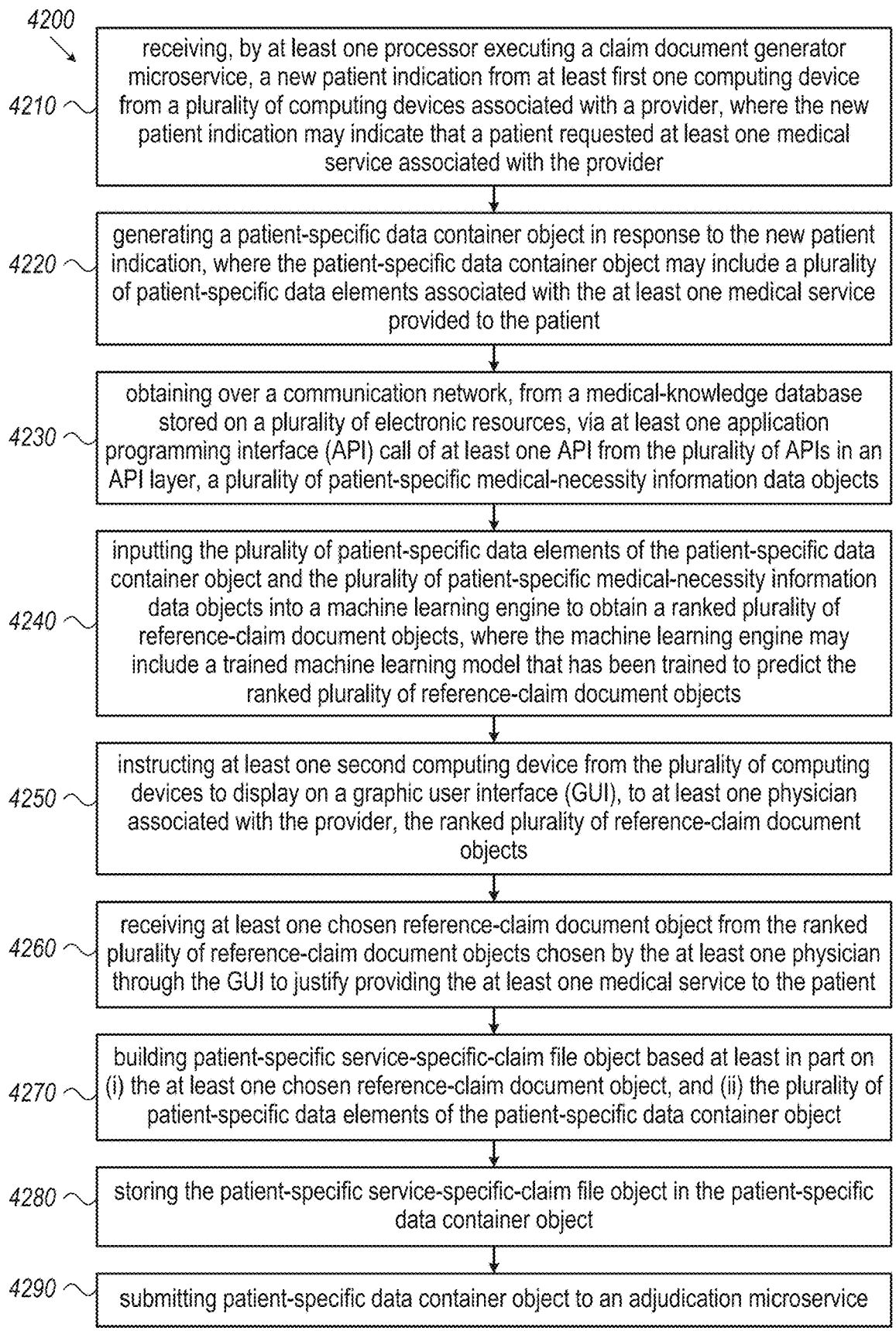
FIG. 61 is a flowchart of a method for generating a patient-specific service-specific claim file object in accordance with one or more embodiments of the present disclosure.

FIG. 61 is a flowchart of a method 4200 for generating a patient-specific service-specific claim file object in accordance with one or more embodiments of the present disclosure. The method 4200 may be performed by the claim document generator microservice 40 and may be executed by at least one processor 50 in the plurality of backend devices implementing the platform layer.

The method 4200 may include receiving 4210, by at least one processor executing a claim document generator microservice, a new patient indication (e.g., detected by the new patient alert monitor 575) from at least first one computing device from a plurality of computing devices (e.g., the plurality of provider devices 90A . . . 90B in the platform frontend 2001) associated with a provider, where the new patient indication may indicate that a patient requested at least one medical service associated with the provider.

The method 4200 may include generating 4220 a patient-specific data container object (e.g., the EEC 300 such as by the admissions processor 585, for example) in response to the new patient indication, where the patient-specific data container object may include a plurality of patient-specific data elements (such as the consult packages 610_0 . . . 610_n) associated with the at least one medical service provided to the patient.

The method 4200 may include obtaining 4230 over a communication network, from a medical-knowledge database (e.g., the KB-MS 630) stored on a plurality of electronic resources 25A . . . 25B, via at least one application programming interface (API) call of at least one API 105 (e.g., the electronic resource API 105) from the plurality of APIs in an API layer 100, a plurality of patient-specific medical-necessity information data objects (e.g., obtained from the KB-MS 630 database query).

The method 4200 may include inputting 4240 the plurality of patient-specific data elements of the patient-specific data container object and the plurality of patient-specific medical-necessity information data objects into a machine learning engine (e.g., the document design expert system 22 that may include recipe builder 925 or recipe ranker/generator 26 and/or (first) MLM Model 24) to obtain a ranked plurality of reference-claim document objects 655, where the machine learning engine may include a trained machine learning model that has been trained to predict the (first) ranked plurality of reference-claim document objects.

The method 4200 may include instructing 4250 at least one second computing device from the plurality of computing devices to display on a graphic user interface (GUI) 91A . . . 91B, to at least one physician associated with the provider, the ranked plurality of reference-claim document objects 650.

The method 4200 may include receiving 4260 at least one chosen reference-claim document object from the ranked plurality of reference-claim document objects chosen by the at least one physician through the GUI to justify providing the at least one medical service to the patient.

The method 4200 may include building 4270 patient-specific service-specific-claim file object (e.g., the claim document 930) based at least in part on (i) the at least one chosen reference-claim document object, and (ii) the plurality of patient-specific data elements (e.g., the consult packages 610_0 . . . 610_n) of the patient-specific data container object (e.g., the EEC 300).

The method 4200 may include storing 4280 the patient-specific service-specific-claim file object in the patient-specific data container object (e.g., the EEC 300).

The method 4200 may include submitting 4290 patient-specific data container object (e.g., the EEC 300) to an adjudication microservice 60.

Figure 62:
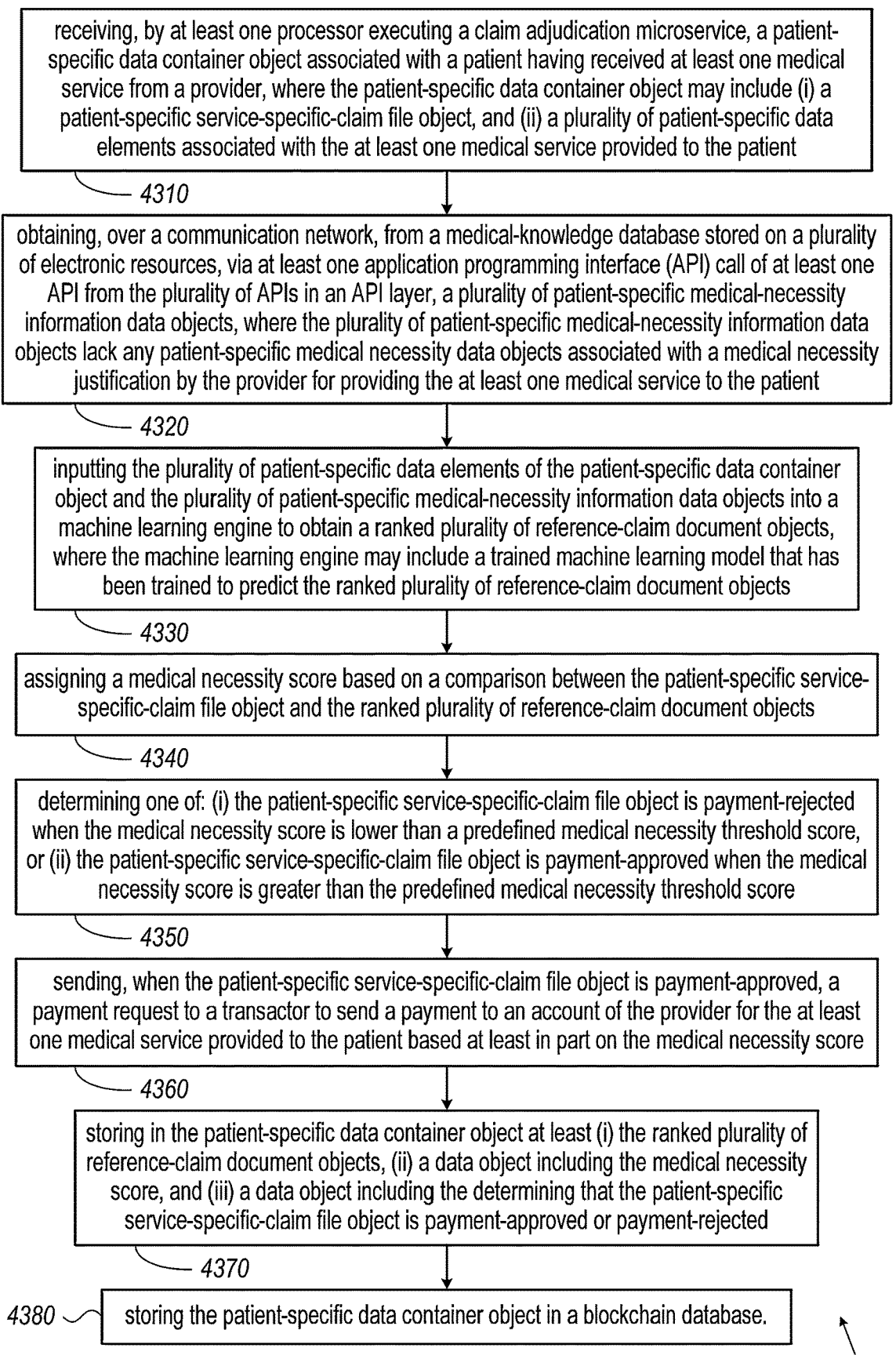
FIG. 62 is a flowchart of a method for determining when a patient-specific service-specific claim file object is payment-approved or payment-rejected in accordance with one or more embodiments of the present disclosure.

FIG. 62 is a flowchart of a method 4300 for determining when a patient-specific service-specific claim file object is payment-approved or payment-rejected in accordance with one or more embodiments of the present disclosure. The method 4300 may be performed by the claim adjudication microservice 60 and may be executed by at least one processor 50.

The method 4300 may include receiving 4310, by at least one processor executing a claim adjudication microservice 60, a patient-specific data container object (the EEC 300) associated with a patient having received at least one medical service from a provider, where the patient-specific data container object may include (i) a patient-specific service-specific-claim file object (e.g., the claim document 930), and (ii) a plurality of patient-specific data elements (e.g., the consult packages 610_0 . . . 610_n) associated with the at least one medical service provided to the patient.

The method 4300 may include obtaining 4320, over a communication network, from a medical-knowledge database (e.g., KB-MS 630) stored on a plurality of electronic resources 25A . . . 25B, via at least one application programming interface (API) call of at least one API 105 from the plurality of APIs in an API layer 100, a plurality of patient-specific medical-necessity information data objects, where the plurality of patient-specific medical-necessity information data objects lack any patient-specific medical necessity data objects (e.g., removing the data objects related to the physician actions of Table 800 in FIG. 11) associated with a medical necessity justification by the provider for providing the at least one medical service to the patient.

The method 4300 may include inputting 4330 the plurality of patient-specific data elements of the patient-specific data container object and the plurality of patient-specific medical-necessity information data objects into a machine learning engine to obtain a ranked plurality of reference-claim document objects 1040, where the machine learning engine may include a trained machine learning model 62 that has been trained to predict the ranked plurality of reference-claim document objects 1040 (e.g., in the ranked list 1035).

The method 4300 may include assigning 4340 (e.g., by the claim comparator 1115) a medical necessity score based on a comparison between the patient-specific service-specific-claim file object and the ranked plurality of reference-claim document objects. The medical necessity score may be an internal correlation coefficient or other correlation metric indicative of a medical necessity correlation between the submitted claim 930 and the ranked reference claim 1040.

The method 4300 may include determining 4350 one of: (i) the patient-specific service-specific-claim file object is payment-rejected when the medical necessity score is lower than a predefined medical necessity threshold score, or (ii) the patient-specific service-specific-claim file object is payment-approved when the medical necessity score is greater than the predefined medical necessity threshold score.

The method 4300 may include sending 4360, when the patient-specific service-specific-claim file object is payment-approved, a payment request to a transactor 1205 to send a payment to an account of the provider for the at least one medical service provided to the patient based at least in part on the medical necessity score.

The method 4300 may include storing 4370 in the patient-specific data container object at least (i) the ranked plurality of reference-claim document objects 1040, (ii) a data object including the medical necessity score, and (iii) a data object including the determining that the patient-specific service-specific-claim file object is payment-approved or payment-rejected.

The method 4300 may include storing 4380 the patient-specific data container object in a blockchain database (e.g., EEC blockchain database 140).

In some embodiments, exemplary inventive, specially programmed computing systems/platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiments, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of exemplary inventive computer-based systems/platforms, exemplary inventive computer-based devices, and/or exemplary inventive computer-based components of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of exemplary inventive computer-based systems/platforms, exemplary inventive computer-based devices, and/or exemplary inventive computer-based components of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a social media post, a map, an entire application (e.g., a calculator), etc. In some embodiments, as detailed herein, one or more of exemplary inventive computer-based systems/platforms, exemplary inventive computer-based devices, and/or exemplary inventive computer-based components of the present disclosure may be implemented across one or more of various computer platforms such as, but not limited to: (1) FreeBSD, NetBSD, OpenBSD; (2) Linux; (3) Microsoft Windows; (4) OS X (MacOS); (5) MacOS 11; (6) Solaris; (7) Android; (8) iOS; (9) Embedded Linux; (10) Tizen; (11) WebOS; (12) IBM i; (13) IBM AIX; (14) Binary Runtime Environment for Wireless (BREW); (15) Cocoa (API); (16) Cocoa Touch; (17) Java Platforms; (18) JavaFX; (19) JavaFX Mobile; (20) Microsoft DirectX; (21) .NET Framework; (22) Silverlight; (23) Open Web Platform; (24) Oracle Database; (25) Qt; (26) Eclipse Rich Client Platform; (27) SAP NetWeaver; (28) Smartface; and/or (29) Windows Runtime.

In some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, exemplary inventive computer-based systems/platforms, exemplary inventive computer-based devices, and/or exemplary inventive computer-based components of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, exemplary inventive computer-based systems/platforms, exemplary inventive computer-based devices, and/or exemplary inventive computer-based components of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, and/or objects. For example, such projections may be a visual overlay for a mobile augmented reality (MAR) application.

In some embodiments, exemplary inventive computer-based systems/platforms, exemplary inventive computer-based devices, and/or exemplary inventive computer-based components of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the exemplary inventive computer-based systems/platforms, the exemplary inventive computer-based devices, and/or the exemplary inventive computer-based components of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs). The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

In some embodiments, the exemplary inventive computer-based systems/platforms, the exemplary inventive computer-based devices, and/or the exemplary inventive computer-based components of the present disclosure may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:

i) Define Neural Network architecture/model,
ii) Transfer the input data to the exemplary neural network model,
iii) Train the exemplary model incrementally,
iv) determine the accuracy for a specific number of timesteps,
v) apply the exemplary trained model to process the newly-received input data,
vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments, a method may include:
receiving, by at least one claim management processor of at least one claim management microservices orchestration computer communicating over a communication network with a plurality of computing devices through a plurality of application programming interfaces (API), a new patient indication from at least one computing device from the plurality of computing devices associated with a provider;
  where the new patient indication may indicate that a patient requested at least one medical service from the provider;
generating, by the at least one claim management processor, a patient-specific data container in response to the new patient indication;
  where the patient-specific data container may include patient data for generating a claim;
iteratively storing, by the at least one claim management processor, a plurality of patient-specific data elements in a patient database;
  where the patient database may be stored in at least one storage device in the at least one claim management microservices orchestration computer;
  where each of the plurality of patient-specific data elements related to the patient received from a graphic user interface (GUI) of any computing device from the plurality of computing devices may include data records of at least one of:
    (i) a patient-physician interaction,
    (ii) a patient diagnostic test result,
    (iii) a patient treatment, and
    (iv) a patient evaluation;
receiving, by the at least one claim management processor, a patient discharge indication from at least one computing device from the plurality of computing devices;
  where the patient discharge indication may indicate that the patient was discharged by the provider after being provided the at least one medical service;
receiving, by the at least one claim management processor, a plurality of provider-support documentation files from a plurality of provider-controlled bots configured to scan a medical knowledge base stored in a plurality of electronic resources in communication with the at least one claim management microservices orchestration computer using keywords taken from the plurality of patient-specific data elements related to the patient;
  where the plurality of provider-support documentation files may provide information to support the provider in establishing a justified medical necessity for providing the at least one medical service to the patient until the patient discharge indication was received;
inputting, by the at least one claim management processor, the patient-specific data elements related to the patient and the plurality of provider-support documentation files into a provider expert system;
  where the provider expert system may include at least one inference engine, at least one machine learning model, or any combination thereof, for determining a level of the justified medical necessity for providing the at least one medical service to the patient based on the plurality of provider-support documentation files received from the medical knowledge base;
receiving, by the at least one claim management processor, output data elements from the provider expert system that are ranked according to the justified medical necessity;
displaying, by the at least one claim management processor, on the GUI of at least one computing device of the plurality of computing devices to at least one physician associated with the provider, a ranked list of the output data elements for the at least one physician to choose for establishing the justified medical necessity for providing the at least one medical service to the patient;
receiving, by the at least one claim management processor, a response message from the GUI of the at least one computing device with the output data elements from the ranked list of output data elements chosen by the at least one physician;
generating, by the at least one claim management processor, a claim document file based at least on:
  (i) the output data elements chosen by the at least one physician,
  (ii) the plurality of provider-support documentation files received from the medical knowledge base, and
  (iii) the plurality of patient-specific data elements related to the patient,
storing, by the at least one claim management processor, in the patient-specific data container at least:
  (i) the claim document file; and
  (ii) the plurality of patient-specific data elements related to the patient; and
storing, by the at least one claim management processor, the patient-specific data container of the patient in a patient-specific data container database.

A method may include:
receiving, by at least one claim management processor of at least one claim management microservices orchestration computer communicating over a communication network, from a patient-specific data container database, a patient-specific data container that may include patient data related to a patient having received at least one medical service from a provider;
  where the patient-specific data container may include at least:
    (i) a provider-generated claim document file; and
    (ii) a plurality of patient-specific data elements related to the patient;

receiving, by the at least one claim management processor, a plurality of payer-determination documentation files from a medical knowledge base stored in a plurality of electronic resources in communication with the at least one claim management microservices orchestration computer using keywords taken from the plurality of patient-specific data elements related to the patient;
  where the plurality of payer-determination documentation files may provide information to support the payer in determining whether the provider provided the at least one medical service to the patient based on a justified medical necessity;
inputting, by the at least one claim management processor, the patient-specific data elements related to the patient and the plurality of payer-determination documentation files into a payer expert system;
  where the payer expert system may include at least one inference engine, at least one machine learning model, or any combination thereof, for determining a level of the justified medical necessity for the provider having provided the at least one medical service to the patient based on the plurality of payer-determination documentation files received from the medical knowledge base;
receiving, by the at least one claim management processor, a plurality of reference claim document files outputted from the payer expert system with rankings according to the justified medical necessity;
assigning, by the at least one claim management processor, a justified medical necessity score based on the rankings to a comparison of the provider-generated claim document file and the plurality of reference claim document files;
determining, by the at least one claim management processor, that the provider-generated claim document file is to be paid when the justified medical necessity score exceeds a predefined threshold;
querying, by the at least one claim management processor, a first blockchain database for a smart contract data file to determine a value of a provider payment for the at least one medical service rendered to the patient based on the justified medical necessity score;
where the smart contract data file may include an agreement between the payer and the provider;
sending, by the at least one claim management processor, a payment request to a payment gateway associated with the provider, to send the provider payment to an account of the provider;
storing, by the at least one claim management processor, in the patient-specific data container at least:
  (i) the plurality of reference claim document files outputted from the payer expert system,
  (ii) the justified medical necessity score, and
  (iii) the value of a provider payment paid to the provider; and
recording, by the at least one claim management processor, the patient-specific data container in a second blockchain database.
In some embodiments, a method may include:
receiving, by at least one processor executing a first microservice, a first user indication from at least first one computing device from a plurality of computing devices associated with a second user;
  where the first user indication may indicate that a first user requested at least one service associated with the second user;
generating, by the at least one processor, a first user-specific data container object in response to the first user indication;
  where the first user-specific data container object may include a plurality of first user-specific data elements associated with the at least one service provided to the first user;
obtaining, by the at least one processor, over a communication network, from at least one database stored on a plurality of electronic resources, via at least one application programming interface (API) call of at least one API from the plurality of APIs in an API layer, a plurality of first user-specific service-necessity information data objects;
inputting, by the at least one processor, the plurality of first user-specific data elements of the first user-specific data container object and the plurality of first user-specific service-necessity information data objects into a machine learning engine to obtain a ranked plurality of reference-claim data objects;
  where the machine learning engine may include a trained machine learning model that has been trained to predict the ranked plurality of reference-claim data objects;
instructing, by the at least one processor, at least one second computing device from the plurality of computing devices to display on a graphic user interface (GUI), to the second user, the ranked plurality of reference-claim data objects;
receiving, by the at least one processor, at least one chosen reference-claim data object from the ranked plurality of reference-claim data objects chosen by the second user through the GUI to justify providing the at least one service to the first user;
building, by the at least one processor, a first user-specific service-specific-claim data object based at least in part on:
  (i) the at least one chosen reference-claim data object, and
  (ii) the plurality of first user-specific data elements of the first user-specific data container object;
storing, by the at least one processor, the first user-specific service-specific-claim data object in the first user-specific data container object; and
submitting, by the at least one processor, the first user-specific data container object to a second microservice.
In some embodiments, the first microservice may be a claim document generator microservice and the second microservice may be a claim adjudication microservice;
  where the first user may be a patient;
  where the second user may be a provider;
  where the first user indication may be a new patient indication;
  where the at least one service may be at least one medical service provided to the patient by the provider;
  where the first user-specific data container object may be a patient-specific data container object;
  where plurality of first user-specific data elements may be a plurality of patient-specific data elements, each patient-specific data element may include patient data associated with the at least one medical service provided to the patient;
  where the at least one database may be a medical knowledge database stored in the plurality of electronic resources;

where the plurality of first user-specific service-necessity information data objects may be a plurality of patient-specific medical-necessity information data objects;
where the ranked plurality of reference-claim data objects may be a ranked plurality of reference-claim document objects; and
where the first user-specific service-specific-claim data object may be a patient-specific service-specific-claim file object.

In some embodiments, the patient data in each patient-specific data element from the plurality of patient-specific data elements may include at least one of:
(i) a patient-physician interaction,
(ii) a patient diagnostic test result,
(iii) a patient treatment, and
(iv) a patient evaluation;

In some embodiments, the at least one processor executing the claim document generator microservice may be configured to communicate over the communication network with the plurality of computing devices and the plurality of electronic resources through the plurality of APIs in the API layer.

In some embodiments, the method may include receiving, by the at least one processor, a patient discharge indication from at least one third computing device from the plurality of computing devices;
where the patient discharge indication may indicate that the patient was discharged by the provider after receiving the at least one medical service.

In some embodiments, the obtaining of the plurality of patient-specific medical-necessity information data objects from the at least one database stored on the plurality of electronic resources via the at least one API call may include:
transmitting, by the at least one processor, at least one instruction to at least one controller of a plurality of controllers controlling the plurality of electronic resources to trigger the at least one API call;
where the at least one API call may program the at least one controller for:
(i) identifying the plurality of patient-specific medical-necessity information data objects from data objects stored in the medical knowledge database based on keywords associated with the patient data in each of the plurality of patient-specific data elements associated with the at least one medical service provided to the patient, and
(ii) transmitting the plurality of patient-specific medical-necessity information data objects that were identified in the medical knowledge database over the communication network to at least one computer executing the claim document generator microservice.

In some embodiments, the medical knowledge database may include a medical key-phrase dictionary (MKPD) in a medical knowledge database for medical coding; and may further include:
organizing, by the at least one processor, a plurality of medical codes in the patient data of the plurality of patient-specific data elements; and
applying, by the at least one processor, natural language processing, optical character recognition or both to the plurality of patient-specific data elements to determine keywords obtained from the MKPD based on the plurality of medical codes in each of the plurality of patient-specific data elements;
generating, by the at least one processor, a plurality of queries to query the medical knowledge database based on the keywords obtained from the MKPD;
where the at least one API call may program the at least one controller for identifying the plurality of patient-specific medical-necessity information data objects from data objects stored in the medical knowledge database based on the keywords obtained from the MKPD in the plurality of queries.

In some embodiments, the plurality of medical codes may include a plurality of ICD-10-PCS codes, a plurality of ICD-10-CM codes, or any combination thereof.

In some embodiments, the receiving of the at least one chosen reference-claim data object chosen by the second user may include receiving through the GUI, at least one chosen reference-claim document object from the ranked plurality of reference-claim document objects from a provider-representative, or a physician to providing the at least one medical service to the patient.

In some embodiments, the method may further include receiving, by the at least one processor, a patient discharge indication from at least one third computing device from the plurality of computing devices;
where the patient discharge indication may indicate that the patient was discharged by the provider after receiving the at least one medical service.

In some embodiments, the storing of the first user-specific service-specific-claim data object in the first user-specific data container object may include storing the plurality of patient-specific data elements in the patient-specific data container object during a time period between a time of the new patient indication and a time of the patient discharge indication.

In some embodiments, a system may include:
at least one non-transient computing memory;
a plurality of computing devices;
a plurality of electronic resources;
a plurality of application programming interfaces (API);
at least one processor of at least one computer may be configured to execute a first microservice and to execute computer code stored in the at least one non-transient computing memory that causes the at least one processor to:
receive a first user indication from at least first one computing device from a plurality of computing devices associated with a second user;
where the first user indication may indicate that a first user requested at least one service associated with the second user;
generate a first user-specific data container object in response to the first user indication;
where the first user-specific data container object may include a plurality of first user-specific data elements associated with the at least one service provided to the first user;
obtain over a communication network, from at least one database stored on a plurality of electronic resources, via at least one application programming interface (API) call of at least one API from the plurality of APIs in an API layer, a plurality of first user-specific service-necessity information data objects;
input the plurality of first user-specific data elements of the first user-specific data container object and the plurality of first user-specific service-necessity information data objects into a machine learning engine to obtain a ranked plurality of reference-claim data objects;
    where the machine learning engine may include a trained machine learning model that has been trained to predict the ranked plurality of reference-claim data objects;
instruct at least one second computing device from the plurality of computing devices to display on a graphic user interface (GUI), to the second user, the ranked plurality of reference-claim data objects;
receive at least one chosen reference-claim data object from the ranked plurality of reference-claim data objects chosen by the second user through the GUI to justify providing the at least one service to the first user;
build a first user-specific service-specific-claim data object based at least in part on:
    (i) the at least one chosen reference-claim data object, and
    (ii) the plurality of first user-specific data elements of the first user-specific data container object;
store the first user-specific service-specific-claim data object in the first user-specific data container object; and
submit the first user-specific data container object to a second microservice.

In some embodiments, the first microservice may be a claim document generator microservice and the second microservice may be a claim adjudication microservice;
    where the first user may be a patient;
    where the second user may be a provider;
    where the first user indication is a new patient indication;
    where the at least one service may be at least one medical service provided to the patient by the provider;
    where the first user-specific data container object may be a patient-specific data container object;
    where plurality of first user-specific data elements may be a plurality of patient-specific data elements, each patient-specific data element may include patient data associated with the at least one medical service provided to the patient;
    where the at least one database may be a medical knowledge database stored in the plurality of electronic resources;
    where the plurality of first user-specific service-necessity information data objects may be a plurality of patient-specific medical-necessity information data objects;
    where the ranked plurality of reference-claim data objects may be a ranked plurality of reference-claim document objects; and
    where the first user-specific service-specific-claim data object may be a patient-specific service-specific-claim file object.

In some embodiments, the patient data in each patient-specific data element from the plurality of patient-specific data elements may include at least one of:
    (i) a patient-physician interaction,
    (ii) a patient diagnostic test result,
    (iii) a patient treatment, and
    (iv) a patient evaluation;

In some embodiments, the at least one processor executing the claim document generator microservice may be configured to communicate over the communication network with the plurality of computing devices and the plurality of electronic resources through the plurality of APIs in the API layer.

In some embodiments, the at least one processor may be further configured to receive a patient discharge indication from at least one third computing device from the plurality of computing devices;
    where the patient discharge indication may indicate that the patient was discharged by the provider after receiving the at least one medical service.

In some embodiments, the at least one processor may be configured to obtain the plurality of patient-specific medical-necessity information data objects from the at least one database stored on the plurality of electronic resources via the at least one API call by transmitting at least one instruction to at least one controller of a plurality of controllers controlling the plurality of electronic resources to trigger the at least one API call;
    where the at least one API call may program the at least one controller to:
        (i) identify the plurality of patient-specific medical-necessity information data objects from data objects stored in the medical knowledge database based on keywords associated with the patient data in each of the plurality of patient-specific data elements associated with the at least one medical service provided to the patient, and
        (ii) transmit the plurality of patient-specific medical-necessity information data objects that were identified in the medical knowledge database over the communication network to the at least one computer executing the claim document generator microservice.

In some embodiments, the medical knowledge database may include a medical key-phrase dictionary (MKPD) in a medical knowledge database for medical coding; and where the at least one processor may be configured to:
    organize a plurality of medical codes in the patient data of the plurality of patient-specific data elements; and
    apply natural language processing, optical character recognition or both to the plurality of patient-specific data elements to determine keywords obtained from the MKPD based on the plurality of medical codes in each of the plurality of patient-specific data elements;
    generate a plurality of queries to query the medical knowledge database based on the keywords obtained from the MKPD;
    where the at least one API call may program the at least one controller for identifying the plurality of patient-specific medical-necessity information data objects from data objects stored in the medical knowledge database based on the keywords obtained from the MKPD in the plurality of queries.

In some embodiments, the plurality of medical codes may include a plurality of ICD-10-PCS codes, a plurality of ICD-10-CM codes, or any combination thereof.

In some embodiments, the at least one processor may be configured to receive the at least one chosen reference-claim data object chosen by the second user by receiving through the GUI, at least one chosen reference-claim document object from the ranked plurality of reference-claim document objects from a provider-representative, or a physician to providing the at least one medical service to the patient.

In some embodiments, the at least one processor may be configured to receive a patient discharge indication from at least one third computing device from the plurality of computing devices;
    where the patient discharge indication may indicate that the patient was discharged by the provider after receiving the at least one medical service.

In some embodiments, the at least one processor may be configured to store the first user-specific service-specific-claim data object in the first user-specific data container object by storing the plurality of patient-specific data elements in the patient-specific data container object during a time period between a time of the new patient indication and a time of the patient discharge indication.

In some embodiments, a method may include:
receiving, by at least one processor executing a microservice, a first user-specific data container object associated with a first user having received at least one service from a second user;
where the first user-specific data container object may include:
  (i) a first user-specific service-specific-claim data object, and
  (ii) a plurality of first user-specific data elements associated with the at least one service provided to the first user;
obtaining, by the at least one processor, over a communication network, from at least one database stored on a plurality of electronic resources, via at least one application programming interface (API) call of at least one API from the plurality of APIs in an API layer, a plurality of first user-specific service-necessity information data objects;
  where the plurality of first user-specific service-necessity information data objects may lack any first user-specific necessity information associated with a necessity justification by the second user for providing the at least one service to the first user; inputting, by the at least one processor, the plurality of first user-specific data elements of the first user-specific data container object and the plurality of first user-specific service-necessity information data objects into a machine learning engine to obtain a ranked plurality of reference-claim data objects;
  where the machine learning engine may include a trained machine learning model that has been trained to predict the ranked plurality of reference-claim data objects;
assigning, by the at least one processor, a service-necessity score based on a comparison between the first user-specific service-specific-claim data object and the ranked plurality of reference-claim data objects;
determining, by the at least one processor, one of:
  i) the first user-specific service-specific-claim data object may fail an authorization when the service-necessity score is lower than a predefined necessity threshold score or
  ii) the first user-specific service-specific-claim data object may meet the authorization when the service-necessity score is greater than the predefined necessity threshold score;
sending, by the at least one processor, when the first user-specific service-specific-claim data object meets the authorization, an authorization request to a transactor to execute a predetermined action associated with the second user so that the second user is recognized for the at least one service based at least in part on the service-necessity score;
storing, by the at least one processor, in the first user-specific data container object at least:
  (i) the ranked plurality of reference-claim data objects,
  (ii) a data object that may include the service-necessity score, and
  (iii) a data object that may include the determining that the first user-specific service-specific-claim data object fails or meets the authorization; and
storing, by the at least one processor, the first user-specific data container object in a blockchain database.

In some embodiments, the microservice may be a claim adjudication microservice;
where the first user may be a patient;
where the second user may be a provider;
where the at least one service may be at least one medical service provided to the patient by the provider;
where the first user-specific data container object may be a patient-specific data container object;
where the first user-specific service-specific-claim data object may be a patient-specific service-specific-claim file object;
where plurality of first user-specific data elements may be a plurality of patient-specific data elements, each patient-specific data element that may include patient data associated with the at least one medical service provided to the patient;
where the at least one database may be a medical knowledge database stored in the plurality of electronic resources;
where the plurality of first user-specific service-necessity information data objects may be a plurality of patient-specific medical-necessity information data objects;
where the ranked plurality of reference-claim data objects may be a ranked plurality of reference-claim document objects;
where the service-necessity score may be a medical service necessity score;
where the authorization may be a payment approval;
where the authorization request may be a payment request to the transactor;
where the predetermined action may be sending a payment to an account of the provider for the at least one medical service provided to the patient; and
where the blockchain database may be a blockchain database for storing the patient-specific data container object.

In some embodiments, the patient data in each patient-specific data element from the plurality of patient-specific data elements may include at least one of:
(i) a patient-physician interaction,
(ii) a patient diagnostic test result,
(iii) a patient treatment, and
(iv) a patient evaluation;

In some embodiments, the at least one processor executing the claim adjudication microservice may be configured to communicate over the communication network with the plurality of electronic resources through the plurality of APIs in the API layer.

In some embodiments, the obtaining of the plurality of patient-specific medical-necessity information data objects from the at least one database stored on the plurality of electronic resources via the at least one API call may include:
transmitting, by the at least one processor, at least one instruction to at least one controller of a plurality of controllers controlling the plurality of electronic resources to trigger the at least one API call;
  where the at least one API call may program the at least one controller for:
  (i) identifying the plurality of patient-specific medical-necessity information data objects from data objects stored in the medical knowledge database based on keywords associated with the patient data in each of the plurality of patient-specific data elements associated with the at least one medical service provided to the patient, and (ii) transmitting the plurality of patient-specific medical-necessity information data objects that were identified in the medical knowledge database over the communication network to at least one computer executing the claim adjudication microservice;

where the plurality of patient-specific medical-necessity information data objects may lack any patient-specific necessity information associated with a necessity justification by the provider for providing the at least one medical service to the patient.

In some embodiments, the medical knowledge database may include a medical key-phrase dictionary (MKPD) in a medical knowledge database for medical coding; and the method may further include:

organizing, by the at least one processor, a plurality of medical codes in the patient data of the plurality of patient-specific data elements; and applying, by the at least one processor, natural language processing, optical character recognition or both to the plurality of patient-specific data elements to determine keywords obtained from the MKPD based on the plurality of medical codes in each of the plurality of patient-specific data elements;

generating, by the at least one processor, a plurality of queries to query the medical knowledge database based on the keywords obtained from the MKPD;

where the at least one API call may program the at least one controller for identifying the plurality of patient-specific medical-necessity information data objects from data objects stored in the medical knowledge database based on the keywords obtained from the MKPD in the plurality of queries.

In some embodiments, the plurality of medical codes may include a plurality of ICD-10-PCS codes, a plurality of ICD-10-CM codes, or any combination thereof.

In some embodiments, the machine learning engine may include a trained machine learning model that has been trained to predict the ranked plurality of reference-claim data objects, the service-necessity score, the determining when the first user-specific service-specific-claim data object meets or fails an authorization, or any combination thereof.

In some embodiments, the inputting may include inputting the plurality of patient-specific data elements of the patient-specific data container object and the plurality of patient-specific service-necessity information data objects into the machine learning engine to obtain the ranked plurality of reference-claim data objects, the medical service necessity score, the determining when patient-specific service-specific-claim file object meets or fails a payment approval, or any combination thereof.

In some embodiments, the method may include receiving, by the at least one processor, from a smart contract blockchain database, a smart contract between the provider and a payer; and where the sending may include sending the payment request to the transactor for sending the payment to the account of the provider for the at least one medical service provided to the patient with a payment value based on the smart contract, the medical service necessity score, or both.

In some embodiments, a system may include:
at least one non-transient computing memory;
a plurality of electronic resources;
a plurality of application programming interfaces (API);
at least one processor of at least one computer may be configured to execute a microservice and to execute computer code stored in the at least one non-transient computing memory that may cause the at least one processor to:

receive a first user-specific data container object associated with a first user having received at least one service from a second user;

where the first user-specific data container object may include:
(i) a first user-specific service-specific-claim data object, and
(ii) a plurality of first user-specific data elements associated with the at least one service provided to the first user;

obtain over a communication network, from at least one database stored on a plurality of electronic resources, via at least one application programming interface (API) call of at least one API from the plurality of APIs in an API layer, a plurality of first user-specific service-necessity information data objects;

where the plurality of first user-specific service-necessity information data objects may lack any first user-specific necessity information associated with a necessity justification by the second user for providing the at least one service to the first user; input the plurality of first user-specific data elements of the first user-specific data container object and the plurality of first user-specific service-necessity information data objects into a machine learning engine to obtain a ranked plurality of reference-claim data objects;

where the machine learning engine may include a trained machine learning model that has been trained to predict the ranked plurality of reference-claim data objects;

assign a service-necessity score based on a comparison between the first user-specific service-specific-claim data object and the ranked plurality of reference-claim data objects;

determine one of:
i) the first user-specific service-specific-claim data object fails an authorization when the service-necessity score is lower than a predefined necessity threshold score or
ii) the first user-specific service-specific-claim data object meets the authorization when the service-necessity score is greater than the predefined necessity threshold score;

send, when the first user-specific service-specific-claim data object meets the authorization, an authorization request to a transactor to execute a predetermined action associated with the second user so that the second user is recognized for the at least one service based at least in part on the service-necessity score;

store in the first user-specific data container object at least:
(i) the ranked plurality of reference-claim data objects,
(ii) a data object that may include the service-necessity score, and
(iii) a data object that may include the determining that the first user-specific service-specific-claim data object fails or meets the authorization; and store the first user-specific data container object in a blockchain database.

In some embodiments, the microservice may be a claim adjudication microservice;
  where the first user may be a patient;
  where the second user may be a provider;
  where the at least one service may be at least one medical service provided to the patient by the provider;
  where the first user-specific data container object may be a patient-specific data container object;
  where the first user-specific service-specific-claim data object may be a patient-specific service-specific-claim file object;
  where plurality of first user-specific data elements may be a plurality of patient-specific data elements, each patient-specific data element may include patient data associated with the at least one medical service provided to the patient;
  where the at least one database may be a medical knowledge database stored in the plurality of electronic resources;
  where the plurality of first user-specific service-necessity information data objects may be a plurality of patient-specific medical-necessity information data objects;
  where the ranked plurality of reference-claim data objects may be a ranked plurality of reference-claim document objects;
  where the service-necessity score may be a medical service necessity score;
  where the authorization may be a payment approval;
  where the authorization request may be a payment request to the transactor;
  where the predetermined action may be sending a payment to an account of the provider for the at least one medical service provided to the patient; and
  where the blockchain database may be a blockchain database for storing the patient-specific data container object.

In some embodiments, the patient data in each patient-specific data element from the plurality of patient-specific data elements may include at least one of:
  (i) a patient-physician interaction,
  (ii) a patient diagnostic test result,
  (iii) a patient treatment, and
  (iv) a patient evaluation;

In some embodiments, the at least one processor executing the claim adjudication microservice may be configured to communicate over the communication network with the plurality of electronic resources through the plurality of APIs in the API layer.

In some embodiments, the at least one processor may be configured to obtain the plurality of patient-specific medical-necessity information data objects from the at least one database stored on the plurality of electronic resources via the at least one API call by transmitting at least one instruction to at least one controller of a plurality of controllers controlling the plurality of electronic resources to trigger the at least one API call;
  where the at least one API call may program the at least one controller to:
    (i) identify the plurality of patient-specific medical-necessity information data objects from data objects stored in the medical knowledge database based on keywords associated with the patient data in each of the plurality of patient-specific data elements associated with the at least one medical service provided to the patient, and
    (ii) transmit the plurality of patient-specific medical-necessity information data objects that were identified in the medical knowledge database over the communication network to at least one computer executing the claim adjudication microservice;
  where the plurality of patient-specific medical-necessity information data objects may lack any patient-specific necessity information associated with a necessity justification by the provider for providing the at least one medical service to the patient.

In some embodiments, the medical knowledge database may include a medical key-phrase dictionary (MKPD) in a medical knowledge database for medical coding; and where the at least one processor may be further configured to:
  organize a plurality of medical codes in the patient data of the plurality of patient-specific data elements; and
  apply natural language processing, optical character recognition or both to the plurality of patient-specific data elements to determine keywords obtained from the MKPD based on the plurality of medical codes in each of the plurality of patient-specific data elements; and
  generate a plurality of queries to query the medical knowledge database based on the keywords obtained from the MKPD;
  where the at least one API call may program the at least one controller to identify the plurality of patient-specific medical-necessity information data objects from data objects stored in the medical knowledge database based on the keywords obtained from the MKPD in the plurality of queries.

In some embodiments, the plurality of medical codes may include a plurality of ICD-10-PCS codes, a plurality of ICD-10-CM codes, or any combination thereof.

In some embodiments, the machine learning engine may include a trained machine learning model that has been trained to predict the ranked plurality of reference-claim data objects, the service-necessity score, the determining when the first user-specific service-specific-claim data object meets or fails an authorization, or any combination thereof.

In some embodiments, the at least one processor may be configured to input the plurality of patient-specific data elements of the patient-specific data container object and the plurality of patient-specific service-necessity information data objects into the machine learning engine to obtain the ranked plurality of reference-claim data objects, the medical service necessity score, the determining when patient-specific service-specific-claim file object meets or fails a payment approval, or any combination thereof.

In some embodiments, the at least one processor may be further configured to receive from a smart contract blockchain database, a smart contract between the provider and a payer; and
  where the at least one processor may be configured to send the payment request to the transactor for sending the payment to the account of the provider for the at least one medical service provided to the patient with a payment value based on the smart contract, the medical service necessity score, or both.

In some embodiments, a platform may include:
  a platform frontend that may include:
    a plurality of frontend computing devices that may be programmed to interface with:
      a plurality of provider computing devices;
      a plurality of payer computing devices; and
      a plurality of electronic resources; and
  a platform backend that may include:
    a plurality of backend computing devices that may include a plurality of processors and a plurality of non-transient computer memories storing a plurality of computing instructions;

where, when executing plurality of computing instructions, at least one processor of the plurality of processors may be programmed to execute:

an access portal that may include a plurality of application programming interfaces (API);

a blockchain as a service suite module; and an emergent utilization suite that may include a claim document generator microservice and a claim adjudication microservice module;

where the claim document generator microservice may be programmed to:

receive a new patient indication from at least one provider computing device from the plurality of frontend computing devices associated with a provider;

where the new patient indication may indicate that a patient requested at least one medical service associated with the provider;

generate a patient-specific data container object in response to the new patient indication;

where the patient-specific data container object may include a plurality of patient-specific data elements associated with the at least one medical service provided to the patient;

obtain over a communication network, from a medical-knowledge database stored on the plurality of electronic resources, via at least one first application programming interface (API) call of at least one first API from the plurality of APIs, a first plurality of patient-specific medical-necessity information data objects;

input the plurality of patient-specific data elements of the patient-specific data container object and the first plurality of patient-specific medical-necessity information data objects into a first machine learning engine to obtain a first ranked plurality of reference-claim document objects;

where the first machine learning engine may include a first trained machine learning model that has been trained to predict the first ranked plurality of reference-claim document objects;

instruct the at least one provider computing device from the plurality of frontend computing devices to display on a graphic user interface (GUI), to at least one physician associated with the provider, the first ranked plurality of reference-claim document objects;

receive at least one chosen reference-claim document object from the first ranked plurality of reference-claim document objects chosen by the at least one physician through the GUI to justify providing the at least one medical service to the patient;

build a patient-specific service-specific-claim file object based at least in part on:
(i) the at least one chosen reference-claim document object, and
(ii) the plurality of patient-specific data elements of the patient-specific data container object;

store the patient-specific service-specific-claim file object in the patient-specific data container object; and submit the patient-specific data container object to an adjudication microservice;

where the adjudication microservice may be programmed to:

receive, from the claim document generator microservice, the patient-specific data container object associated with the patient having received the at least one medical service from the provider;

where the patient-specific data container object may include:
(i) the patient-specific service-specific-claim file object, and
(ii) the plurality of patient-specific data elements associated with the at least one medical service provided to the patient;

obtain over the communication network, from the medical-knowledge database, via at least one second API call of at least one second API from the plurality of APIs in an API layer, a second plurality of patient-specific medical-necessity information data objects;

where the second plurality of patient-specific medical-necessity information data objects may lack any patient-specific medical necessity data objects associated with a medical necessity justification by the provider for providing the at least one medical service to the patient;

input the plurality of patient-specific data elements of the patient-specific data container object and the second plurality of patient-specific medical-necessity information data objects into a second machine learning engine to obtain a second ranked plurality of reference-claim document objects;

where the second machine learning engine may include a second trained machine learning model that has been trained to predict the second ranked plurality of reference-claim document objects;

assign a medical necessity score based on a comparison between the patient-specific service-specific-claim file object and the second ranked plurality of reference-claim document objects;

determine one of:
(i) the patient-specific service-specific-claim file object is payment-rejected when the medical necessity score is lower than a predefined medical necessity threshold score or
(ii) the patient-specific service-specific-claim file object is payment-approved when the medical necessity score is greater than the predefined medical necessity threshold score;

send, when the patient-specific service-specific-claim file object is payment-approved, a payment request to a transactor to send a payment to an account of the provider for the at least one medical service provided to the patient based at least in part on the medical necessity score;

store in the patient-specific data container object at least:
(i) the second ranked plurality of reference-claim document objects,
(ii) a first data object that may include the medical necessity score, and
(iii) a second data object that may include the determining that the patient-specific service-specific-claim file object is payment-approved or payment-rejected; and store the patient-specific data container object in a blockchain database.

In some embodiments, a method may include:
executing, by at least one processor, a claim document generator microservice that may be programmed to:
receive a new patient indication from at least one provider computing device from a plurality of frontend computing devices associated with a provider;
where the new patient indication may indicate that a patient requested at least one medical service associated with the provider;
generate a patient-specific data container object in response to the new patient indication;
where the patient-specific data container object may include a plurality of patient-specific data elements associated with the at least one medical service provided to the patient;
obtain over a communication network, from a medical-knowledge database stored on a plurality of electronic resources, via at least one first application programming interface (API) call of at least one first API from the plurality of APIs, a first plurality of patient-specific medical-necessity information data objects;
input the plurality of patient-specific data elements of the patient-specific data container object and the first plurality of patient-specific medical-necessity information data objects into a first machine learning engine to obtain a first ranked plurality of reference-claim document objects;
where the first machine learning engine may include a first trained machine learning model that has been trained to predict the first ranked plurality of reference-claim document objects;
instruct the at least one provider computing device from the plurality of frontend computing devices to display on a graphic user interface (GUI), to at least one physician associated with the provider, the first ranked plurality of reference-claim document objects;
receive at least one chosen reference-claim document object from the first ranked plurality of reference-claim document objects chosen by the at least one physician through the GUI to justify providing the at least one medical service to the patient;
build a patient-specific service-specific-claim file object based at least in part on:
(i) the at least one chosen reference-claim document object, and
(ii) the plurality of patient-specific data elements of the patient-specific data container object;
store the patient-specific service-specific-claim file object in the patient-specific data container object; and
submit the patient-specific data container object to an adjudication microservice; executing, by at least one processor, a adjudication microservice is programmed to:
receive, from the claim document generator microservice, the patient-specific data container object associated with the patient having received the at least one medical service from the provider;
where the patient-specific data container object may include:
(i) the patient-specific service-specific-claim file object, and
(ii) the plurality of patient-specific data elements associated with the at least one medical service provided to the patient;
obtain over the communication network, from the medical-knowledge database, via at least one second API call of at least one second API from the plurality of APIs in an API layer, a second plurality of patient-specific medical-necessity information data objects;
where the second plurality of patient-specific medical-necessity information data objects may lack any patient-specific medical necessity data objects associated with a medical necessity justification by the provider for providing the at least one medical service to the patient;
input the plurality of patient-specific data elements of the patient-specific data container object and the second plurality of patient-specific medical-necessity information data objects into a second machine learning engine to obtain a second ranked plurality of reference-claim document objects;
where the second machine learning engine may include a second trained machine learning model that has been trained to predict the second ranked plurality of reference-claim document objects;
assign a medical necessity score based on a comparison between the patient-specific service-specific-claim file object and the second ranked plurality of reference-claim document objects;
determine one of:
(i) the patient-specific service-specific-claim file object is payment-rejected when the medical necessity score is lower than a predefined medical necessity threshold score or
(ii) the patient-specific service-specific-claim file object is payment-approved when the medical necessity score is greater than the predefined medical necessity threshold score;
send, when the patient-specific service-specific-claim file object is payment-approved, a payment request to a transactor to send a payment to an account of the provider for the at least one medical service provided to the patient based at least in part on the medical necessity score;
store in the patient-specific data container object at least:
(i) the second ranked plurality of reference-claim document objects,
(ii) a first data object that may include the medical necessity score, and
(iii) a second data object that may include the determining that the patient-specific service-specific-claim file object is payment-approved or payment-rejected; and
store the patient-specific data container object in a blockchain database.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the inventive systems/platforms, and the inventive devices described herein can be utilized in any combination with each other. Further still, the various steps may be carried out in any desired order (and any desired steps may be added and/or any desired steps may be eliminated).

The invention claimed is:
1. A method, comprising:
executing, by at least one processor of a plurality of backend computing devices, a claim document generator microservice and an adjudication microservice collocated in a scalable claim management platform;

wherein the scalable claim management platform, comprises at least one load balancer, and is configured to:
dynamically scale a number of backend computing devices based on data traffic assessed by the at least one load balancer so as to maximize computational and load efficiencies in the plurality of backend computing devices,
interact with a plurality of frontend computing devices comprising a plurality of provider computing devices associated with a plurality of providers and a plurality of payer computing devices associated with a plurality of payers through an application programming interface (API) layer comprising a plurality of APIs,
relay data associated with a plurality of patients between any of the plurality of provider computing devices and the claim document generator microservice, and
provide, for any of the plurality of provider computing devices and any of the plurality of payer computing devices via the API layer, a same access to a trusted medical knowledge database stored in a plurality of electronic resources that is trusted by the plurality of providers and the plurality of payers,
wherein the claim document generator microservice is programmed to:
receive a new patient indication from at least one first provider computing device from the plurality of provider computing devices associated with at least one first provider from the plurality of providers;
wherein the new patient indication indicates that at least one first patient from the plurality of patients requested at least one medical service associated with the at least one first provider;
generate a patient-specific data container object in response to the new patient indication;
wherein the patient-specific data container object comprises a plurality of patient-specific data elements associated with the at least one medical service provided to at least one first patient;
transmit over a communication network, at least one first API call to the trusted medical knowledge database stored on the plurality of electronic resources;
wherein the at least one first API call programs the trusted medical knowledge database to:
identify a first plurality of patient-specific medical-necessity information data objects associated with the at least one medical service provided to the at least one first patient, and
transmit the first plurality of patient-specific medical-necessity information data objects to the claim document generator microservice;
receive over the communication network, from the trusted medical knowledge database, the first plurality of patient-specific medical-necessity information data objects;
input the plurality of patient-specific data elements of the patient-specific data container object and the first plurality of patient-specific medical-necessity information data objects into a first machine learning engine that has been trained to predict:
a first plurality of reference claim document objects, and
a first medical-necessity score for each of the first plurality of reference claim document objects;
rank each of the first plurality of reference claim document objects using the first medical-necessity score to obtain a first ranked plurality of reference-claim document objects;
instruct the at least one first provider computing device to display on a graphic user interface (GUI), to at least one physician associated with the at least one first provider, the first ranked plurality of reference-claim document objects;
receive at least one chosen reference-claim document object from the first ranked plurality of reference-claim document objects chosen by the at least one physician through the GUI to justify providing the at least one medical service to the at least one first patient;
build a patient-specific service-specific-claim file object based at least in part on:
(i) the at least one chosen reference-claim document object, and
(ii) the plurality of patient-specific data elements of the patient-specific data container object;
store the patient-specific service-specific-claim file object in the patient-specific data container object; and
submit the patient-specific data container object to the adjudication microservice;
wherein the adjudication microservice is programmed to:
receive, from the claim document generator microservice, the patient-specific data container object associated with the at least one first patient having received the at least one medical service from the at least one first provider from the plurality of providers;
wherein the patient-specific data container object comprises:
(i) the patient-specific service-specific-claim file object, and
(ii) the plurality of patient-specific data elements associated with the at least one medical service provided to the at least one first patient;
transmit over the communication network, at least one second API call to the trusted medical knowledge database stored on the plurality of electronic resources;
wherein the at least one second API call programs the trusted medical knowledge database to:
identify a second plurality of patient-specific medical-necessity information data objects associated with the at least one medical service provided to the at least one first patient that exclude any patient-specific medical-necessity data objects associated with a medical-necessity justification by the at least one first provider for providing the at least one medical service to the at least one first patient, and
transmit the second plurality of patient-specific medical-necessity information data objects to the adjudication microservice;
receive over the communication network, from the trusted medical knowledge database, the second plurality of patient-specific medical-necessity information data objects;
input the plurality of patient-specific data elements of the patient-specific data container object and the second plurality of patient-specific medical-necessity information data objects into a second machine learning engine that has been trained to predict:

a second plurality of reference claim document objects, and
a second medical-necessity score, for each of the second plurality of reference claim document objects, that excludes any association with the medical-necessity justification by the at least one first provider;
rank each of the second plurality of reference claim document objects using the second medical-necessity score to obtain a second ranked plurality of reference-claim document objects;
assign a third medical-necessity score to the patient-specific service-specific-claim file object based on a comparison between the patient-specific service-specific-claim file object and the second ranked plurality of reference-claim document objects;
determine a payment determination based on one of:
(i) the patient-specific service-specific-claim file object is payment-rejected when the third medical-necessity score is lower than a predefined medical-necessity threshold score or
(ii) the patient-specific service-specific-claim file object is payment-approved when the third medical-necessity score is greater than the predefined medical-necessity threshold score;
send, when the patient-specific service-specific-claim file object is payment-approved, a payment request to a transactor to send a payment to an account of the at least one first provider for the at least one medical service provided to the at least one first patient based at least in part on the third medical-necessity score;
store in the patient-specific data container object at least:
(i) the second ranked plurality of reference-claim document objects,
(ii) a first data object comprising the third medical-necessity score, and
(iii) a second data object comprising the payment determination that the patient-specific service-specific-claim file object is payment-approved or payment-rejected; and
store the patient-specific data container object in a blockchain database.

2. The method according to claim 1, wherein patient data in each patient-specific data element from the plurality of patient-specific data elements comprises at least one of:
a patient-physician interaction,
(ii) a patient diagnostic test result,
(iii) a patient treatment, and
(iv) a patient evaluation.

3. The method according to claim 1, wherein the claim document generator microservice is further programmed to obtain the first plurality of patient-specific medical-necessity information data objects from the trusted medical knowledge database stored on the plurality of electronic resources via the at least one first API call by transmitting at least one instruction to at least one controller of a plurality of controllers controlling the plurality of electronic resources to trigger the at least one first API call;
wherein the at least one first API call programs the at least one controller to:
(i) identify the first plurality of patient-specific medical-necessity information data objects from data objects stored in the trusted medical knowledge database based on keywords associated with patient data in each of the plurality of patient-specific data elements associated with the at least one medical service provided to the at least one first patient, and
(ii) transmit the first plurality of patient-specific medical-necessity information data objects that were identified in the trusted medical knowledge database over the communication network to the at least one first provider computing device executing the claim document generator microservice.

4. The method according to claim 3, wherein the trusted medical knowledge database comprises a medical key-phrase dictionary (MKPD) in a medical knowledge database for medical coding; and wherein the claim document generator microservice is further programmed to:
organize a plurality of medical codes in the patient data of the plurality of patient-specific data elements; and
apply natural language processing, optical character recognition or both to the plurality of patient-specific data elements to determine keywords obtained from the MKPD based on the plurality of medical codes in each of the plurality of patient-specific data elements;
generate a plurality of first queries to query the trusted medical knowledge database based on the keywords obtained from the MKPD;
wherein the at least one first API call programs the at least one controller for identifying the first plurality of patient-specific medical-necessity information data objects from data objects stored in the trusted medical knowledge database based on the keywords obtained from the MKPD in the plurality of first queries.

5. The method according to claim 4, wherein the plurality of medical codes comprises a plurality of ICD-10-PCS codes, a plurality of ICD-10-CM codes, or any combination thereof.

6. The method according to claim 1, wherein the claim document generator microservice is further programmed to receive the at least one chosen reference-claim document object chosen by the at least one first provider by receiving through the GUI, the at least one chosen reference-claim document object from the first ranked plurality of reference-claim document objects from a provider-representative, or a physician to providing the at least one medical service to the at least one first patient.

7. The method according to claim 1, wherein the claim document generator microservice is further programmed to receive a patient discharge indication from at least one second provider computing device from the plurality of frontend computing devices;
wherein the patient discharge indication indicates that the at least one first patient was discharged by the at least one first provider after receiving the at least one medical service.

8. The method according to claim 7, wherein the claim document generator microservice is further programmed to store the patient-specific service-specific-claim file object in the patient-specific data container object by storing the plurality of patient-specific data elements in the patient-specific data container object during a time period between a time of the new patient indication and a time of the patient discharge indication.

9. The method according to claim 1, wherein the adjudication microservice is further programmed to obtain the second plurality of patient-specific medical-necessity information data objects from the trusted medical knowledge database stored on the plurality of electronic resources via the at least one second API call by transmitting at least one instruction to at least one controller of a plurality of controllers controlling the plurality of electronic resources to trigger the at least one second API call;
  wherein the at least one second API call programs the at least one controller to:
    (i) identify the second plurality of patient-specific medical-necessity information data objects from data objects stored in the trusted medical knowledge database based on keywords associated with patient data in each of the plurality of patient-specific data elements associated with the at least one medical service provided to the at least one first patient, and
    (ii) transmit the second plurality of patient-specific medical-necessity information data objects that were identified in the trusted medical knowledge database over the communication network to the at least one processor of at least one backend computing device from a plurality of backend computing devices executing the adjudication microservice;
      wherein the second plurality of patient-specific medical-necessity information data objects lack any patient-specific necessity information associated with a necessity justification by the at least one first provider for providing the at least one medical service to the at least one first patient.

10. The method according to claim 9, wherein the trusted medical knowledge database comprises a medical key-phrase dictionary (MKPD) in a medical knowledge database for medical coding; and wherein the adjudication microservice is further programmed to:
  organize a plurality of medical codes in the patient data of the plurality of patient-specific data elements; and
  apply natural language processing, optical character recognition or both to the plurality of patient-specific data elements to determine keywords obtained from the MKPD based on the plurality of medical codes in each of the plurality of patient-specific data elements; and
  generate a plurality of second queries to query the trusted medical knowledge database based on the keywords obtained from the MKPD;
    wherein the at least one second API call programs the at least one controller to identify the second plurality of patient-specific medical-necessity information data objects from data objects stored in the trusted medical knowledge database based on the keywords obtained from the MKPD in the plurality of second queries.

11. The method according to claim 10, wherein the plurality of medical codes comprises a plurality of ICD-10-PCS codes, a plurality of ICD-10-CM codes, or any combination thereof.

12. The method according to claim 1, wherein the adjudication microservice is further programmed to receive from a smart contract blockchain database, a smart contract between the at least one first provider and a payer; and
  wherein the adjudication microservice is further programmed to send the payment request to the transactor for sending the payment to the account of the at least one first provider for the at least one medical service provided to the at least one first patient with a payment value based on the smart contract, the second medical-necessity score, or both.

13. A platform, comprising:
a platform frontend, comprising:
  a plurality of frontend computing devices that are programmed to interface with:
    a plurality of provider computing devices;
    a plurality of payer computing devices; and
  a plurality of electronic resources; and
a platform backend comprising:
  a plurality of backend computing devices comprising a plurality of processors and a plurality of non-transient computer memories storing a plurality of computing instructions;
    wherein the plurality of backend computing devices is configured to execute a claim document generator microservice and an adjudication microservice collocated in a scalable claim management platform;
    wherein the scalable claim management platform, comprises at least one load balancer, and is configured to:
      dynamically scale a number of backend computing devices based on data traffic assessed by the at least one load balancer so as to maximize computational and load efficiencies in the plurality of backend computing devices,
      interact with the plurality of frontend computing devices comprising the plurality of provider computing devices associated with a plurality of providers and the plurality of payer computing devices associated with a plurality of payers through an application programming interface (API) layer comprising a plurality of APIs,
      relay data associated with a plurality of patients between any of the plurality of provider computing devices and a claim document generator microservice, and
      provide, for any of the plurality of provider computing devices and any of the plurality of payer computing devices via the API layer, a same access to a trusted medical knowledge database stored in a plurality of electronic resources that is trusted by the plurality of providers and the plurality of payers,
    wherein, when executing the plurality of computing instructions, at least one processor of the plurality of processors is programmed to execute:
      an access portal, comprising the plurality of APIs;
      a blockchain as a service suite module; and
      an emergent utilization suite comprising the claim document generator microservice and the adjudication microservice;
        wherein the claim document generator microservice is programmed to:
        receive a new patient indication from at least one first provider computing device from the plurality of provider computing devices associated with at least one first provider from the plurality of providers;
          wherein the new patient indication indicates that a at least one first patient from the plurality of patients requested at least one medical service associated with the at least one first provider;
        generate a patient-specific data container object in response to the new patient indication;
          wherein the patient-specific data container object comprises a plurality of patient-specific data elements associated with the at least one medical service provided to at least one first patient;

transmit over a communication network, at least one first API call to the trusted medical knowledge database stored on the plurality of electronic resources;
  wherein the at least one first API call programs the trusted medical knowledge database to:
    identify a first plurality of patient-specific medical-necessity information data objects associated with the at least one medical service provided to the at least one first patient, and
    transmit the first plurality of patient-specific medical-necessity information data objects to the claim document generator microservice;
  receive over the communication network, from the trusted medical knowledge database, the first plurality of patient-specific medical-necessity information data objects;
input the plurality of patient-specific data elements of the patient-specific data container object and the first plurality of patient-specific medical-necessity information data objects into a first machine learning engine that has been trained to predict:
a first plurality of reference claim document objects, and
a first medical-necessity score for each of the first plurality of reference claim document objects;
rank each of the first plurality of reference claim document objects using the first medical-necessity score to obtain a first ranked plurality of reference-claim document objects;
  instruct the at least one first provider computing device to display on a graphic user interface (GUI), to at least one physician associated with the at least one first provider, the first ranked plurality of reference-claim document objects;
  receive at least one chosen reference-claim document object from the first ranked plurality of reference-claim document objects chosen by the at least one physician through the GUI to justify providing the at least one medical service to the at least one first patient;
  build a patient-specific service-specific-claim file object based at least in part on:
    (i) the at least one chosen reference-claim document object, and
    (ii) the plurality of patient-specific data elements of the patient-specific data container object;
  store the patient-specific service-specific-claim file object in the patient-specific data container object; and
  submit the patient-specific data container object to the adjudication microservice;
wherein the adjudication microservice is programmed to:
  receive, from the claim document generator microservice, the patient-specific data container object associated with the at least one first patient having received the at least one medical service from the at least one first provider from the plurality of providers;
    wherein the patient-specific data container object comprises:
      (i) the patient-specific service-specific-claim file object, and
      (ii) the plurality of patient-specific data elements associated with the at least one medical service provided to the at least one first patient;
    transmit over the communication network, at least one second API call to the trusted medical knowledge database stored on the plurality of electronic resources;
    wherein the at least one second API call programs the trusted medical knowledge database to:
      identify a second plurality of patient-specific medical-necessity information data objects associated with the at least one medical service provided to the at least one first patient that exclude any patient-specific medical-necessity data objects associated with a medical-necessity justification by the at least one first provider for providing the at least one medical service to the at least one first patient, and
      transmit the second plurality of patient-specific medical-necessity information data objects to the adjudication microservice;
    receive over the communication network, from the trusted medical knowledge database, the second plurality of patient-specific medical-necessity information data objects;
  input the plurality of patient-specific data elements of the patient-specific data container object and the second plurality of patient-specific medical-necessity information data objects into a second machine learning engine that has been trained to predict:
    a second plurality of reference claim document objects, and
    a second medical-necessity score, for each of the second plurality of reference claim document objects, that excludes any association with the medical-necessity justification by the at least one first provider,
  rank each of the second plurality of reference claim document objects using the second medical-necessity score to obtain a second ranked plurality of reference-claim document objects;
  assign a third medical-necessity score to the patient-specific service-specific-claim file object based on a comparison between the patient-specific service-specific-claim file object and the second ranked plurality of reference-claim document objects;
  determine a payment determination based on one of:
  (i) the patient-specific service-specific-claim file object is payment-rejected when the third medical-necessity score is lower than a predefined medical-necessity threshold score or
  (ii) the patient-specific service-specific-claim file object is payment-approved when the third medical-necessity score is greater than the predefined medical-necessity threshold score;
  send, when the patient-specific service-specific-claim file object is payment-approved, a payment request to a transactor to send a payment to an account of the at least one first provider for the at least one medical service provided to the at least one first patient based at least in part on the third medical-necessity score;

store in the patient-specific data container object at least:
  (i) the second ranked plurality of reference-claim document objects,
  (ii) a first data object comprising the third medical-necessity score, and
  (iii) a second data object comprising the payment determination that the patient-specific service-specific-claim file object is payment-approved or payment-rejected; and
store the patient-specific data container object in a blockchain database.

14. The platform according to claim 13, wherein patient data in each patient-specific data element from the plurality of patient-specific data elements comprises at least one of:
  (i) a patient-physician interaction,
  (ii) a patient diagnostic test result,
  (iii) a patient treatment, and
  (iv) a patient evaluation.

15. The platform according to claim 13, wherein the claim document generator microservice is further programmed to obtain the first plurality of patient-specific medical-necessity information data objects from the trusted medical knowledge database stored on the plurality of electronic resources via the at least one first API call by transmitting at least one instruction to at least one controller of a plurality of controllers controlling the plurality of electronic resources to trigger the at least one first API call;
  wherein the at least one first API call programs the at least one controller to:
    (i) identify the first plurality of patient-specific medical-necessity information data objects from data objects stored in the trusted medical knowledge database based on keywords associated with patient data in each of the plurality of patient-specific data elements associated with the at least one medical service provided to the at least one first patient, and
    (ii) transmit the first plurality of patient-specific medical-necessity information data objects that were identified in the trusted medical knowledge database over the communication network to the at least one first provider computing device executing the claim document generator microservice.

16. The platform according to claim 15, wherein the trusted medical knowledge database comprises a medical key-phrase dictionary (MKPD) in a medical knowledge database for medical coding; and wherein the claim document generator microservice is further programmed to:
  organize a plurality of medical codes in the patient data of the plurality of patient-specific data elements; and
  apply natural language processing, optical character recognition or both to the plurality of patient-specific data elements to determine keywords obtained from the MKPD based on the plurality of medical codes in each of the plurality of patient-specific data elements;
  generate a plurality of first queries to query the trusted medical knowledge database based on the keywords obtained from the MKPD;
    wherein the at least one first API call programs the at least one controller for identifying the first plurality of patient-specific medical-necessity information data objects from data objects stored in the trusted medical knowledge database based on the keywords obtained from the MKPD in the plurality of first queries.

17. The platform according to claim 16, wherein the plurality of medical codes comprises a plurality of ICD-10-PCS codes, a plurality of ICD-10-CM codes, or any combination thereof.

18. The platform according to claim 13, wherein the claim document generator microservice is further programmed to receive the at least one chosen reference-claim document object chosen by the at least one first provider by receiving through the GUI, the at least one chosen reference-claim document object from the first ranked plurality of reference-claim document objects from a provider-representative, or a physician to providing the at least one medical service to the at least one first patient.

19. The platform according to claim 13, wherein the claim document generator microservice is further programmed to receive a patient discharge indication from at least one second provider computing device from the plurality of frontend computing devices;
  wherein the patient discharge indication indicates that the at least one first patient was discharged by the at least one first provider after receiving the at least one medical service.

20. The platform according to claim 19, wherein the claim document generator microservice is further programmed to store the patient-specific service-specific-claim file object in the patient-specific data container object by storing the plurality of patient-specific data elements in the patient-specific data container object during a time period between a time of the new patient indication and a time of the patient discharge indication.

21. The platform according to claim 13, wherein the adjudication microservice is further programmed to obtain the second plurality of patient-specific medical-necessity information data objects from the trusted medical knowledge database stored on the plurality of electronic resources via the at least one second API call by transmitting at least one instruction to at least one controller of a plurality of controllers controlling the plurality of electronic resources to trigger the at least one second API call;
  wherein the at least one second API call programs the at least one controller to:
    (i) identify the second plurality of patient-specific medical-necessity information data objects from data objects stored in the trusted medical knowledge database based on keywords associated with patient data in each of the plurality of patient-specific data elements associated with the at least one medical service provided to the at least one first patient, and
    (ii) transmit the second plurality of patient-specific medical-necessity information data objects that were identified in the trusted medical knowledge database over the communication network to the at least one processor of at least one backend computing device from the plurality of backend computing devices executing the adjudication microservice;
      wherein the second plurality of patient-specific medical-necessity information data objects lack any patient-specific necessity information associated with a necessity justification by the at least one first provider for providing the at least one medical service to the at least one first patient.

22. The platform according to claim 21, wherein the trusted medical knowledge database comprises a medical key-phrase dictionary (MKPD) in a medical knowledge database for medical coding; and wherein the adjudication microservice is further programmed to:

organize a plurality of medical codes in the patient data of the plurality of patient-specific data elements; and apply natural language processing, optical character recognition or both to the plurality of patient-specific data elements to determine keywords obtained from the MKPD based on the plurality of medical codes in each of the plurality of patient-specific data elements; and generate a plurality of second queries to query the trusted medical knowledge database based on the keywords obtained from the MKPD;

wherein the at least one second API call programs the at least one controller to identify the second plurality of patient-specific medical-necessity information data objects from data objects stored in the trusted medical knowledge database based on the keywords obtained from the MKPD in the plurality of second queries.

23. The platform according to claim 22, wherein the plurality of medical codes comprises a plurality of ICD-10-PCS codes, a plurality of ICD-10-CM codes, or any combination thereof.

24. The platform according to claim 13, wherein the adjudication microservice is further programmed to receive from a smart contract blockchain database, a smart contract between the at least one first provider and a payer; and wherein the adjudication microservice is further programmed to send the payment request to the transactor for sending the payment to the account of the at least one first provider for the at least one medical service provided to the at least one first patient with a payment value based on the smart contract, the second medical-necessity score, or both.

* * * * *

UNITED STATES PATENT AND TRADEMARK OFFICE
CERTIFICATE OF CORRECTION

| | | |
|---|---|---|
| PATENT NO. | : 11,880,888 B1 | |
| APPLICATION NO. | : 18/063179 | |
| DATED | : January 23, 2024 | |
| INVENTOR(S) | : Howard B. Gold et al. | |

It is certified that error appears in the above-identified patent and that said Letters Patent is hereby corrected as shown below:

On the Title Page

Item (72) Inventors: Line 2, delete "Konstanine Costalas" and insert --Konstantine Costalas--

Signed and Sealed this
Nineteenth Day of March, 2024

Katherine Kelly Vidal
*Director of the United States Patent and Trademark Office*